(12) United States Patent
Sakai et al.

(10) Patent No.: US 10,018,556 B2
(45) Date of Patent: Jul. 10, 2018

(54) GAS DETECTING DEVICE INCLUDING LIGHT EMITTER, LIGHT RECEIVER, AND AN OPTICAL MEMBER

(71) Applicant: Panasonic Intellectual Property Management Co., Ltd., Osaka (JP)

(72) Inventors: Koji Sakai, Hyogo (JP); Naoya Matsuo, Hyogo (JP); Narutoshi Hoshino, Osaka (JP); Tsutomu Shimomura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/844,955

(22) Filed: Sep. 3, 2015

(65) Prior Publication Data

US 2015/0377775 A1    Dec. 31, 2015

Related U.S. Application Data

(63) Continuation of application No. PCT/JP2014/001085, filed on Feb. 28, 2014.

(30) Foreign Application Priority Data

Mar. 4, 2013 (JP) ................. 2013-042059
Mar. 26, 2013 (JP) ................. 2013-064884
Mar. 26, 2013 (JP) ................. 2013-064885

(51) Int. Cl.
*G01J 5/00* (2006.01)
*G01N 21/3504* (2014.01)

(52) U.S. Cl.
CPC ................. *G01N 21/3504* (2013.01)

(58) Field of Classification Search
CPC ......... G01N 21/3504; G01N 2201/062; G01N 21/94; G01N 15/1434; G01N 2021/3181;
(Continued)

(56) References Cited

U.S. PATENT DOCUMENTS 5,320,733 A * 6/1994 Bohm ................. G01N 27/417
204/408
5,340,986 A    8/1994 Wong
(Continued)

FOREIGN PATENT DOCUMENTS

JP    56-164939 A    12/1981
JP    60-31043 A    2/1985
(Continued)

OTHER PUBLICATIONS

International Search Report issued in International Application No. PCT/JP2014/001085 dated May 20, 2014, with English Translation.
(Continued)

*Primary Examiner* — Taeho Jo
(74) *Attorney, Agent, or Firm* — McDermott Will & Emery LLP

(57) ABSTRACT

A device includes a light emitting element, a light receiving element, an electronic part capable of processing a signal output from the light receiving element, an optical member covering the light emitting element and the light receiving element, and a board on which the light emitting element, the light receiving element, the electronic part, and the optical member are mounted. The board includes conductor wiring electrically connected to the light receiving element.

7 Claims, 33 Drawing Sheets

(58) Field of Classification Search
CPC .......... G01N 2021/8514; G01N 21/35; G01N 21/783; G01N 2021/1704
USPC ...................................................... 250/338.1
See application file for complete search history.

(56) References Cited

U.S. PATENT DOCUMENTS

| | | | | |
|---|---|---|---|---|
| 5,864,468 | A * | 1/1999 | Poplawski | G02B 6/4201 361/752 |
| 7,339,657 | B2 * | 3/2008 | Coates | G01N 21/31 250/339.12 |
| 8,957,381 | B2 | 2/2015 | Lin et al. | |
| 2002/0168152 | A1 * | 11/2002 | Abe | G02B 6/4201 385/88 |
| 2004/0188622 | A1 | 9/2004 | Yokura et al. | |
| 2004/0201835 | A1 * | 10/2004 | Coates | G01N 21/31 356/73 |
| 2005/0017206 | A1 * | 1/2005 | Tice | G01N 15/06 250/573 |
| 2005/0093146 | A1 * | 5/2005 | Sakano | H01L 33/62 257/730 |
| 2005/0259262 | A1 | 11/2005 | Fischer et al. | |
| 2006/0149143 | A1 | 7/2006 | Colvin | |
| 2006/0261967 | A1 | 11/2006 | Marman et al. | |
| 2007/0114421 | A1 | 5/2007 | Maehlich et al. | |
| 2007/0192041 | A1 | 8/2007 | Goldstein et al. | |
| 2008/0136331 | A1 * | 6/2008 | Schmeikal | H05B 33/0821 315/32 |
| 2008/0187272 | A1 * | 8/2008 | Sato | G02B 6/4246 385/93 |
| 2008/0277586 | A1 * | 11/2008 | Cardinale | G01M 3/002 250/339.13 |
| 2008/0285910 | A1 * | 11/2008 | Yamada | G02B 6/12002 385/14 |
| 2008/0308733 | A1 | 12/2008 | Doncaster | |
| 2008/0309922 | A1 * | 12/2008 | Anders | G01N 21/552 356/73 |
| 2008/0316489 | A1 * | 12/2008 | Ludwig | G01N 21/0303 356/437 |
| 2009/0023570 | A1 | 1/2009 | Kung et al. | |
| 2009/0234720 | A1 | 9/2009 | George et al. | |
| 2010/0317939 | A1 * | 12/2010 | Kuhn | A61B 5/0084 600/323 |
| 2011/0057104 | A1 * | 3/2011 | Yao | G01J 1/32 250/338.1 |
| 2011/0057129 | A1 * | 3/2011 | Yao | G01S 7/4813 250/552 |
| 2011/0133941 | A1 * | 6/2011 | Yao | G01J 1/02 340/600 |
| 2011/0317965 | A1 * | 12/2011 | Fujimura | G02B 6/4204 385/93 |
| 2012/0155854 | A1 * | 6/2012 | Huang | G03B 17/02 396/535 |
| 2012/0290208 | A1 * | 11/2012 | Jiang | G01N 21/3504 702/8 |
| 2013/0015356 | A1 * | 1/2013 | Shih | G01S 17/026 250/353 |
| 2013/0026369 | A1 * | 1/2013 | Gibson | G01N 21/3504 250/343 |
| 2013/0031957 | A1 * | 2/2013 | Shaw | G08B 17/00 73/28.01 |
| 2013/0086977 | A1 | 4/2013 | Wong | |
| 2013/0289368 | A1 * | 10/2013 | Covington | A61B 1/041 600/302 |
| 2014/0070101 | A1 * | 3/2014 | Matsushima | G01N 21/3504 250/338.5 |
| 2014/0110564 | A1 | 4/2014 | Campbell et al. | |
| 2014/0226149 | A1 * | 8/2014 | Coates | G01F 23/292 356/51 |

FOREIGN PATENT DOCUMENTS

| | | |
|---|---|---|
| JP | 61-155757 U | 9/1986 |
| JP | 3-44795 U | 4/1991 |
| JP | 4-250344 A | 9/1992 |
| JP | 4-259848 A | 9/1992 |
| JP | 6-66724 A | 3/1994 |
| JP | 2002-350341 A | 12/2002 |
| JP | 2006135057 * | 5/2006 |
| JP | 2006-208254 A | 8/2006 |
| JP | 2007-147613 A | 6/2007 |
| JP | 2012-220353 A | 11/2012 |
| WO | 2005/012869 A2 | 2/2005 |

OTHER PUBLICATIONS

U.S. Non-Final Office Action dated May 5, 2017 issued in U.S. Appl. No. 15/477,689.
U.S. Final Office Action dated Aug. 29, 2017 issued in U.S. Appl. No. 15/477,689.
Notice of Allowance cited in U.S. Appl. No. 15/477,689 dated Jan. 23, 2018.

* cited by examiner

US 10,018,556 B2

GAS DETECTING DEVICE INCLUDING LIGHT EMITTER, LIGHT RECEIVER, AND AN OPTICAL MEMBER

RELATED APPLICATIONS

This application is a continuation of International Application No. PCT/JP2014/001085, filed on Feb. 28, 2014, which in turn claims the benefit of Japanese Application No. 2013-042059, filed on Mar. 4, 2013, Japanese Application No. 2013-064884, filed on Mar. 26, 2013, and Japanese Application No. 2013-064885, filed on Mar. 26, 2013 the disclosures of which Applications are incorporated by reference herein.

BACKGROUND

1. Technical Field

The present disclosure relates to a device capable of detecting a particular substance.

2. Background Art

There is an apparatus such as an air conditioner which includes a gas detecting device. The gas detecting device can detect a presence or an absence of a particular gas, a concentration of a gas, and others by utilizing characteristics of a variety of gases which absorb infrared light in different wavelengths for each gas. The air conditioner including the gas detecting device is capable of switching between an external air circulation mode and an internal air circulation mode based on a concentration of a gas such as carbon dioxide output from the gas detecting device.

FIGS. 44 and 45 are a cross-sectional view and an exploded perspective view, respectively, illustrating a conventional gas component detecting device described in Unexamined Japanese Patent Publication No. 2012-220353 (hereinafter referred as PTL). The gas component detecting device of the PTL includes circuit block 1001 and optical block 1002.

In circuit block 1001, body 1010 accommodates light emitting unit 1003, light receiving unit 1004, wavelength filter 1005, and wiring board 1011 within recess 1100. Light emitting unit 1003 emits infrared light easily absorbable by a detection target gas. Light receiving unit 1004 receives infrared light and converts the received light into an electric signal. Wavelength filter 1005 constitutes a band pass filter which has a wavelength band as a transmission band containing a wavelength of infrared light emitted from light emitting unit 1003. Signal processing circuit unit 1006 is mounted on wiring board 1011. Signal processing circuit unit 1006 drives light emitting unit 1003 to allow emission of infrared light from light emitting unit 1003. In addition, signal processing circuit unit 1006 processes the signal output from light receiving unit 1004. Body 1010 is provided with a plurality of insert-molded terminals 1012 (see FIG. 45). Terminals 1012 are electrically connected with wiring board 1011.

In optical block 1002, cover 1020 accommodates light guide 1008 therein. Light guide 1008 is composed of first reflection mirror 1080, second reflection mirror 1081, third reflection mirror 1082, and fourth reflection mirror 1083. According to the gas detecting device, fourth reflection mirror 1083 closes an opening of recess 1100 of body 1010. Cover 1020 in a state accommodating light guide 1008 within recess 1200 is joined with body 1010. Cover 1020 is provided with air hole 1201 formed at a center thereof and penetrating cover 1020. According to the gas detecting device, dust filter 1007 covers air hole 1201.

According to the gas detecting device of the PTL, outside air containing the detection target gas is introduced into light guide 1008 via air hole 1201. According to the gas detecting device, an amount of infrared light received by light receiving unit 1004 decreases by absorption of the infrared light, emitted from light emitting unit 1003, by the detection target gas. The gas detecting device detects a concentration of a gas component based on a processing result of the signal output from light receiving unit 1004 by processing circuit unit 1006. The gas detecting device is capable of outputting a detection signal indicating the concentration of the gas component to the outside via terminals 1012.

FIG. 46 is a perspective view illustrating conventional gas detector 1310 described in WO 2005/012869. Gas detector 1310 includes emitter 1332 capable of emitting emission energy, sensors 1334A and 1334B, and housing 1318.

Housing 1318 includes side walls 1318A, 1318B, 1318C, and 1318D, and opening 1318E. In gas detector 1310, a detection gas flows in a direction of an arrow G with respect to opening 1318E of housing 1318. Sensor 1334A includes optical filter 1336A. Optical filter 1336A transmits light having a wavelength to be absorbed by the detection gas. Sensor 1334B includes optical filter 1336B. Optical filter 1336B does not transmit the light having the wavelength to be absorbed by the detection gas. Housing 1318 includes concave mirrors 1338A and 1338B. According to gas detector 1310, the emission energy emitted from emitter 1332 reflects on a surface of concave mirror 1338A, and enters sensor 1334A via filter 1336A (see fine solid line arrows in FIG. 46). Similarly, according to gas detector 1310, the emission energy emitted from emitter 1332 reflects on a surface of concave mirror 1338B, and enters sensor 1334B via filter 1336B. Each of sensors 1334A and 1334B outputs a signal corresponding to the entering emission energy. These signals are input to control circuit 1316. Control circuit 1316 displays a concentration of the detection gas on display 1320 based on the input signals.

SUMMARY

A device according to the present disclosure includes a light emitting element, a light receiving element, an electronic part capable of processing a signal output from the light receiving element, an optical member covering the light emitting element and the light receiving element, and a board on which the light emitting element, the light receiving element, the electronic part, and the optical member are mounted. The board includes conductor wiring electrically connected to the light receiving element.

DETAILED DESCRIPTION OF PREFERRED EMBODIMENTS

First Exemplary Embodiment

Figure 1:
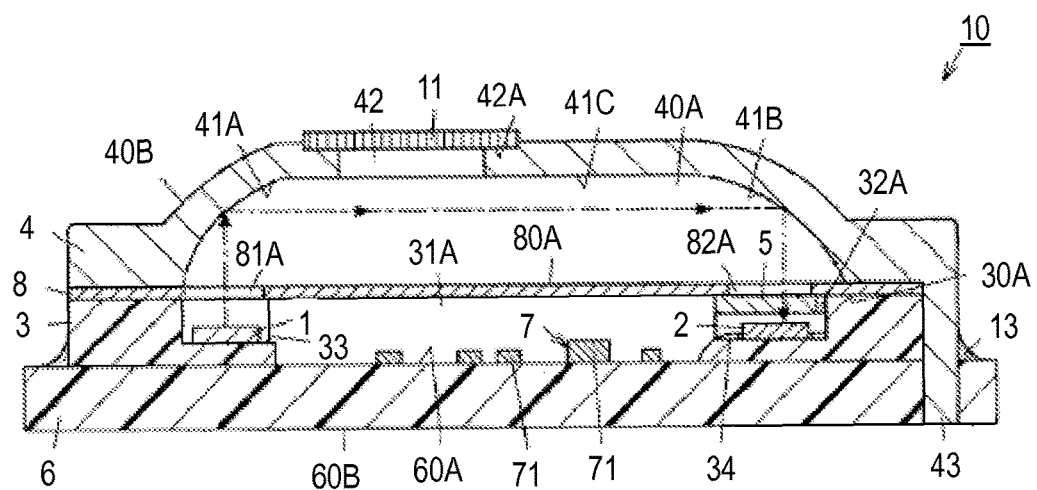
FIG. 1 is a cross-sectional view schematically illustrating a device according to a first exemplary embodiment.
Figure 2:
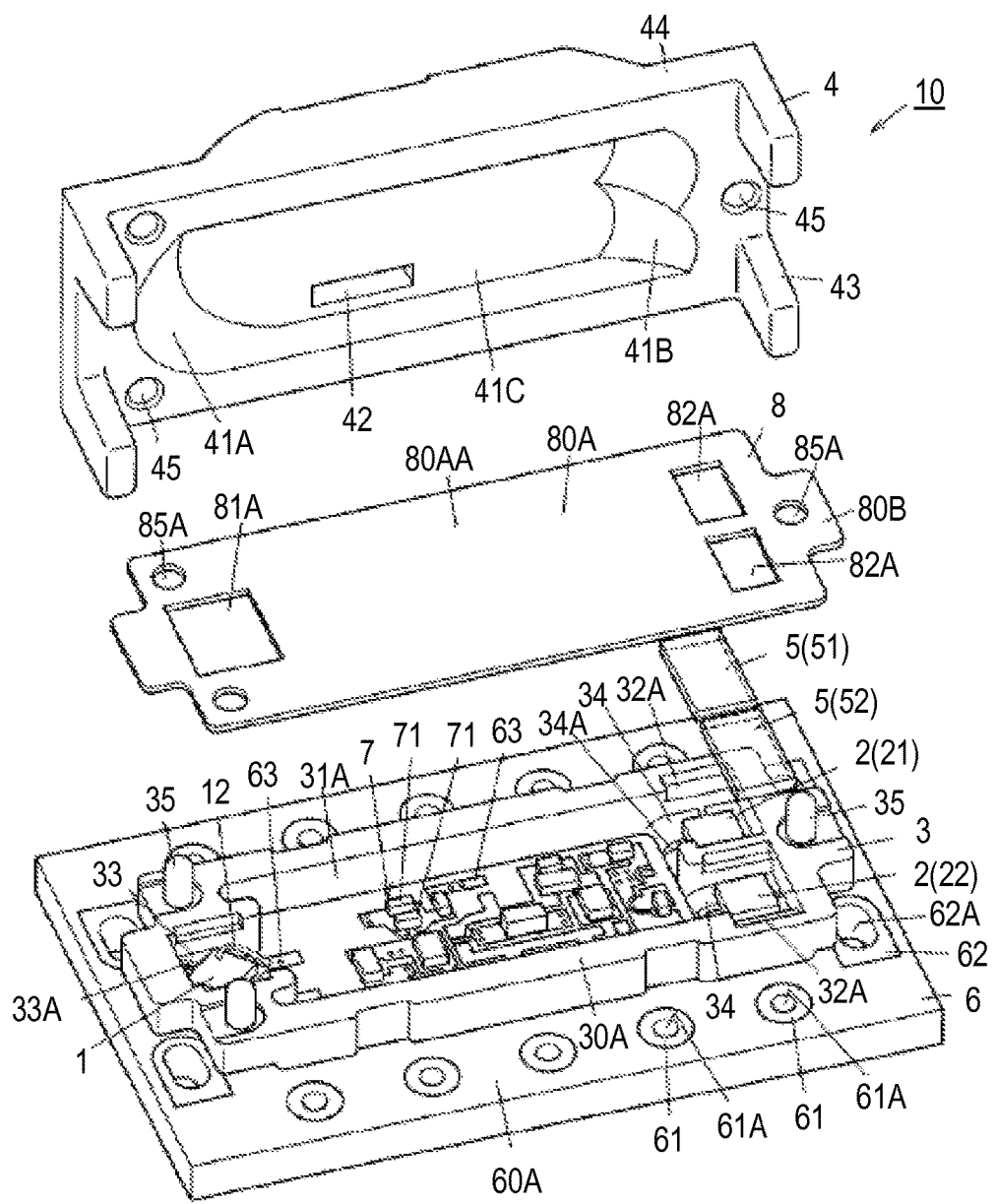
FIG. 2 is an explanatory exploded view illustrating the device according to the first exemplary embodiment.

FIG. 1 and FIG. 2 are a schematic cross-sectional view and an explanatory exploded view, respectively, illustrating device 10 according to a first exemplary embodiment. Device 10 according to this exemplary embodiment is a gas detecting device. Device 10 includes light emitting element 1, light receiving elements 2, signal processing circuit unit 7, optical member 4, and board 6. Signal processing circuit unit 7 processes signals output from light receiving elements 2. Optical member 4 covers light emitting element 1 and light receiving elements 2. Board 6 is a component on which light emitting element 1, light receiving elements 2, signal processing circuit unit 7, and optical member 4 are mounted. Board 6 includes conductor wiring 61 electrically connected to light receiving elements 2.

The structure of device 10 according to this exemplary embodiment can increase a degree of freedom for electric connection with an outside.

A more specific configuration of device 10 according to this exemplary embodiment is hereinafter described.

Device 10 includes light emitting element 1 which emits infrared light, light receiving elements 2 which photoelectrically convert infrared light, and support body 3 which supports light emitting element 1 and light receiving elements 2 on the one surface 30A side of support body 3 with a predetermined distance between light emitting element 1 and light receiving elements 2. Device 10 includes optical member 4 which covers the one surface 30A side of support body 3 via space 40A into which a detection target gas is introducible. Optical member 4 guides infrared light emitted from light emitting element 1 toward light receiving elements 2. Device 10 includes optical filters 5 each disposed on a corresponding optical path along which infrared light emitted from light emitting element 1 is guided toward the corresponding the light receiving element 2 side (see chain line arrows in FIG. 1). Each of optical filters 5 transmits infrared light contained in a predetermined wavelength band. According to device 10, optical member 4 is fixed to board 6 via support body 3, while board 6 includes conductor wiring 61 electrically connected to light receiving elements 2 and outputting signals received from the light receiving elements 2 side to the outside (see FIG. 2).

According to device 10 in this exemplary embodiment, support body 3 is disposed on board 6. An external shape of support body 3 is a rectangular frame shape. Support body 3 is constituted by a resin molded component formed by a synthetic resin molded body. Board 6 has a rectangular plate shape larger than the shape of support body 3. Board 6 is constituted by a glass epoxy resin substrate. Board 6 includes conductor pattern wiring 63 (see FIG. 2) on front surface 60A of board 6. Board 6 includes rear surface 60B opposite to front surface 60A. According to device 10, a plurality of electronic parts 71 are mounted on front surface 60A of board 6. Electronic parts 71 are electrically connected to wiring 63 via soldering (not shown). The plurality of electronic parts 71 are electrically connected to each other via wiring 63 formed on board 6. The plurality of electronic parts 71 constitute signal processing circuit unit 7. Signal processing circuit unit 7 is configured to allow emission of infrared light from light emitting element 1 by controlling light emitting element 1. Signal processing circuit unit 7 is configured to process signals output from light receiving elements 2 after receiving infrared light. Signal processing circuit unit 7 performs signal processing such as amplification, waveform shaping, signal sampling, and signal A/D conversion of signals output from light receiving elements 2. Signal processing circuit unit 7 further performs signal processing such as signal calculation, signal correction, and determination that the detection target gas has an abnormal concentration, for example. In device 10, signal processing circuit unit 7 is disposed within opening 31A of frame-shaped support body 3. In other words, electronic parts 71 capable of processing signals output from light receiving elements 2 are mounted on board 6. According to device 10 structured such that electronic parts 71 constituting signal processing circuit unit 7 are disposed in opening 31A of frame-shaped support body 3, reduction of an entire size of device 10 is achievable.

In device 10, front surface 60A of board 6 is exposed to an inside of opening 31A of frame-shaped support body 3. Support body 3 is provided with first recess 33 at an end of support body 3 on the one surface 30A side. Light emitting element 1 is mounted on an inner bottom surface of first recess 33 of support body 3. According to device 10, light emitting element 1 is mounted on the inner bottom surface of first recess 33 via a die bond material (not shown). In device 10, wiring 63 formed on front surface 60A of board 6 and light emitting element 1 are electrically connected to light emitting element 1 by wire bonding using metal wire 12 as illustrated in FIG. 2. Light emitting element 1 is constituted by a light emitting diode capable of emitting infrared light. This light emitting diode is constituted by a semiconductor bare chip. Light emitting element 1 emits infrared light having a wavelength easily absorbable by the detection target gas. Examples of the detection target gas include carbon monoxide, carbon dioxide, methane, and nitrogen oxide. The structure of light emitting element 1 mounted on first recess 33 of support body 3 is capable of reducing mutual thermal effect with respect to the signal processing circuit unit 7 side provided on board 6. Support body 3 is provided with second recesses 34 at the other end of the one surface 30A side of support body 3 on the side opposite to the one end of support body 3. Light receiving elements 2 are mounted on inner bottom surfaces of second recesses 34 of support body 3, respectively. According to device 10, light receiving elements 2 are mounted on the inner bottom surfaces of second recesses 34 via a die bond material (not shown). In device 10, wire bonding using metal wire (not shown) electrically connects wiring 63 formed on front surface 60A of board 6 to light receiving elements 2. Each of light receiving elements 2 includes an infrared sensor capable of receiving infrared light. Each of the infrared sensors is constituted by a pyroelectric element. Each of the infrared sensors is provided as a semiconductor bare chip. Support body 3 supports light emitting element 1 and light receiving elements 2 on the one surface 30A side with a predetermined distance between light emitting element 1 and each of light receiving elements 2.

Support body 3 is provided with steps 32A formed in opposed inner walls of each of second recesses 34. Optical filters 5 are disposed on the pair of steps 32A of support body 3, respectively, in such a state as to cover corresponding light receiving elements 2. Each of steps 32A has a depth in a direction of a thickness of support body 3 substantially equal to the thickness of each of optical filters 5. Each of optical filters 5 constitutes a band pass filter which has a transmission band containing a predetermined wavelength band in wavelengths of infrared light emitted from light emitting element 1.

Device 10 according to this exemplary embodiment is provided with the pair of second recesses 34 at the other end of support body 3 on the one surface 30A side. Light receiving elements 2 are separately mounted on the corresponding inner bottom surfaces of respective second recesses 34 of support body 3. In device 10, optical filters 5 are separately equipped for corresponding light receiving elements 2 (hereinafter referred to as first light receiving element 21 and second light receiving element 22 as well) in such a state as to cover the pair of light receiving elements 2, respectively.

According to device 10 in this exemplary embodiment, one of optical filters 5 equipped for corresponding light receiving element 2 constitutes first optical filter 51 which has a transmission band containing a wavelength band of infrared light to be absorbed by the detection target gas. According to device 10, the other of optical filters 5 equipped for corresponding light receiving element 2 constitutes second optical filter 52 which does not have a transmission band containing the wavelength band of the infrared light to be absorbed by the detection target gas, but has a transmission band containing wavelengths around the wavelength band of the infrared light to be absorbed by the detection target gas.

Flat-plate-shaped reflection body 8 is mounted on the one surface 30A side of support body 3. Reflection body 8 may be formed of a rectangular flat-plate-shaped plate material. Reflection body 8 has surface 80AA as a smooth surface capable of reflecting infrared light. As illustrated in FIG. 2, reflection body 8 includes rectangular main portion 80A, and projecting portions 80B each having a rectangular shape smaller than the shape of main portion 80A, and projecting from both ends of main portion 80A to the outside. Main portion 80A and projecting portions 80B are formed integrally with each other. Reflection body 8 is provided with first opening 81A through which infrared light emitted from light emitting element 1 can pass at one end of main portion 80A. Reflection body 8 is provided with a pair of through holes 85A at the one end of main portion 80A with first opening 81A interposed between the pair of through holes 85A. In addition, reflection body 8 is provided with second openings 82A through which infrared light receivable by light receiving elements 2 passes at other end of main portion 80A. Reflection body 8 is provided with through hole 85A in projection portion 80B at the other end. Reflection body 8 closes opening 31A of frame-shaped support body 3. In other words, support body 3 has a frame-shaped external appearance. Support body 3 supports reflection body 8 which reflects infrared light toward space 40A. Reflection body 8 covers opening 31A of frame-shaped support body 3.

Device 10 according to this exemplary embodiment includes optical member 4 which covers one surface 30A of support body 3 where reflection body 8 is disposed. Optical member 4 is a resin molded component constituted by a synthetic resin molded body. Optical member 4 includes metal portion 44 (see FIG. 2) as gold-plated area throughout outside surface 40B of optical member 4. Optical member 4 constitutes a cover which covers the one surface 30A side of support body 3 where light emitting element 1 and light receiving elements 2 are supported. Optical member 4 has a rectangular parallelepiped shape which has an external size substantially equal to an external size of support body 3 in a plan view. Optical member 4 is provided with a recess opened to the support body 3 side. According to device 10, the recess of optical member 4 forms space 40A into which the detection target gas is introducible.

As illustrated in FIG. 1, optical member 4 includes first optical path changing portion 41A which contains a first reflection mirror capable of reflecting infrared light emitted from light emitting element 1 in a predetermined direction. Optical member 4 includes second optical path changing portion 41B which contains a second reflection mirror capable of reflecting the infrared light coming from the first optical path changing portion 41A side in a predetermined direction. Optical member 4 further includes third optical path changing portion 41C which contains a third reflection mirror capable of guiding infrared light coming from the first optical path changing portion 41A side toward the second optical path changing portion 41B side. First optical path changing portion 41A includes a reflection surface having a parabolic shape. First optical path changing portion 41A changes a direction of an optical path of infrared light emitted from light emitting element 1 into the predetermined direction perpendicular to the direction of the thickness of the support body 3. Second optical path changing portion 41B includes a reflection surface having a parabolic shape and facing the reflection surface of first optical path changing portion 41A. After a change of the optical path of the infrared light by first optical path changing portion 41A, second optical path changing portion 41B changes the direction of the infrared light into a direction crossing light receiving surfaces of light receiving elements 2. According to device 10, optical member 4 changes the optical path of the infrared light extending from light emitting element 1 toward light receiving elements 2 into a C shape, as illustrated in FIG. 1. The structure of optical member 4 including first optical path changing portion 41A, second optical path changing portion 41B, and third optical path changing portion 41C allows infrared light emitted from light emitting element 1 to travel toward the light receiving elements 2 side.

Optical member 4 is provided with rectangular air holes 42 each of which penetrates optical member 4 in a direction of a thickness of optical member 4. Optical member 4 can introduce the detection target gas into space 40A through air holes 42. Optical member 4 is provided with dust filter 11 on accommodation recess 42A so as to cover air holes 42 of optical member 4. Dust filter 11 prevents dust or other foreign material from entering into air holes 42. Dust filter 11 is fixed to accommodation recess 42A via not-shown adhesives. Optical member 4 has rectangular parallelepiped projections 43 (see FIG. 2) projecting toward the board 6 side at four corners of the rectangular shape of optical member 4, respectively. Support body 3 has engaging projections 35 (see FIG. 2) projecting toward the optical member 4 side on one surface 30A. Each of engaging projections 35 includes a semispherical tip, and has a cylindrical shape as the whole. Support body 3 has a pair of engaging projections 35 projecting toward the optical member 4 side at the one end of one surface 30A. The pair of engaging projections 35 are disposed with light emitting element 1 interposed therebetween in the plan view. Support body 3 has one engaging projection 35 projecting toward the optical member 4 side at a center of the other end of one surface 30A. Optical member 4 has engaging holes 45 (see FIG. 2) for engaging with engaging projections 35 of support body 3.

According to device 10, support body 3 and optical member 4 are capable of positioning with each other by engagement of engaging projections 35 and engaging holes 45. In Device 10, engaging projections 35 and engaging holes 45 facilitate alignment between light emitting element 1 and first optical path changing portion 41A, and alignment between light receiving elements 2 and second optical path changing portion 41B. According to device 10, engagement between support body 3 and optical member 4 is capable of positioning light emitting element 1 at a focus of the parabolic reflection surface of first optical path changing portion 41A. In device 10 according to this exemplary embodiment, it is possible to position light receiving elements 2 at a focus of the parabolic reflection surface of second optical path changing portion 41B by engagement between support body 3 and optical member 4.

According to device 10, optical member 4 is overlaid on board 6, with support body 3 interposed between optical member 4 and board 6, by insertion of projections 43 of optical member 4 into insertion holes 62A of board 6. In device 10, optical member 4 is fixed to board 6 via support body 3 in a state of insertion of projections 43 of optical member 4 into insertion holes 62A of board 6. According to device 10, support body 3 can be positioned with respect to reflection body 8 by insertion of engaging projections 35 of support body 3 into through holes 85A of reflection body 8.

In device 10, engaging projections 35 and through holes 85A facilitate alignment between light emitting element 1 and first opening 81A. In device 10, engaging projections 35 and through holes 85A facilitate alignment between light receiving elements 2 and second openings 82A. Device 10 allows infrared light emitted from light emitting element 1 to pass through first opening 81A by positioning reflection body 8 on support body 3. Device 10 according to this exemplary embodiment allows light receiving elements 2 to receive infrared light passing through second openings 82A by positioning reflection body 8 on support body 3.

Device 10 introduces the outside air into space 40A surrounded by optical member 4 and reflection body 8 via air holes 42. According to device 10, an amount of infrared light transmitted through first optical filter 51 and received by first light receiving element 21 decreases with respect to that of infrared light emitted from light emitting element 1 in accordance with a concentration of the detection target gas. According to device 10, when the concentration of the detection target gas is low, an amount of infrared light received by first light receiving element 21 becomes close to the amount of infrared light emitted from light emitting element 1. When the concentration of the detection target gas is high, the amount of infrared light received by first light receiving element 21 decreases. According to device 10, an amount of infrared light transmitted through second optical filter 52 and received by second light receiving element 22 does not vary in accordance with the concentration of the detection target gas.

In device 10, signal processing circuit unit 7 processes a signal indicating an amount of received infrared light and output from light receiving elements 2. Device 10 is capable of detecting a concentration of a gas component of the detection target gas contained in space 40A surrounded by optical member 4 and reflection body 8.

According to device 10 in this exemplary embodiment, signal processing circuit unit 7 calculates a concentration of the detection target gas based on a difference between output signal levels output from the pair of light receiving elements 2. Signal processing circuit unit 7 obtains the difference between the output signal levels output from first light receiving element 21 and second light receiving element 22, and calculates the concentration of the detection target gas based on this difference.

According to device 10, signal processing circuit unit 7 calculates the concentration of the detection target gas based on the difference between the output signal levels output from first light receiving element 21 and second light receiving element 22. Device 10 is capable of canceling variations of respective output signal levels output from light receiving elements 2 based on the difference between the output signal levels from first light receiving element 21 and second light receiving element 22, so as to prevent lowering of detection accuracy at the time of detection of a concentration of a gas.

When signal processing circuit unit 7 of device 10 calculates a concentration of a gas based only on an output signal level output from one of light receiving elements 2, detection accuracy at the time of detection of the concentration of the gas may lower due to a variation of the output signal level from light receiving element 2 caused by some disturbance factor. However, when signal processing circuit unit 7 of device 10 according to this exemplary embodiment calculates the concentration of the detection target gas based on a difference between output signal levels output from the pair of light receiving elements 2, it is possible to suppress lowering of detection accuracy at the time of detection of the concentration of the gas by canceling variations of the output signal levels from respective light receiving elements 2.

Figure 3:
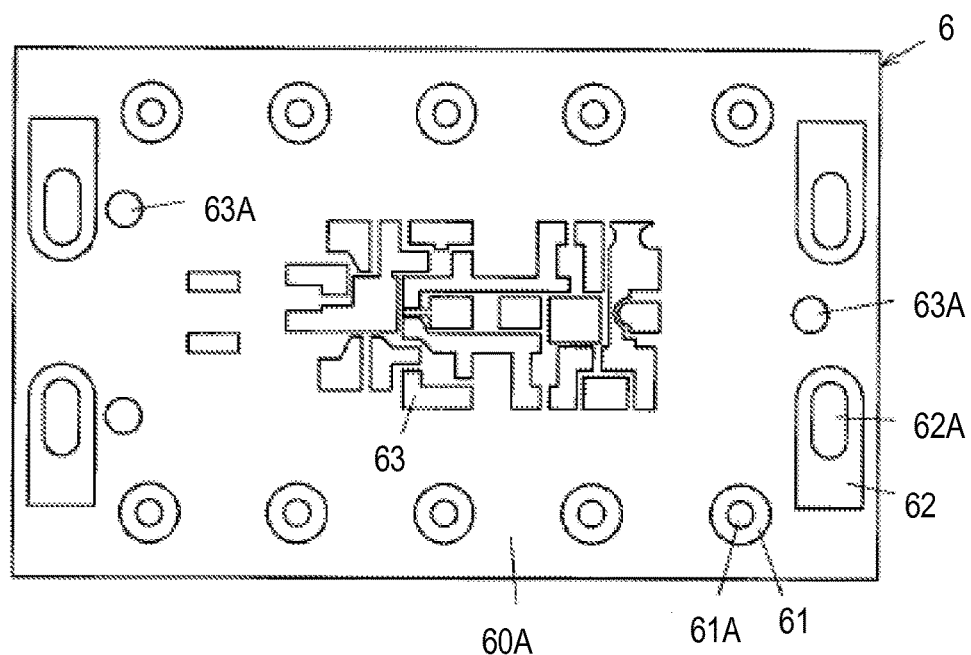
FIG. 3 is a plan view illustrating an essential part of the device according to the first exemplary embodiment.
Figure 4:
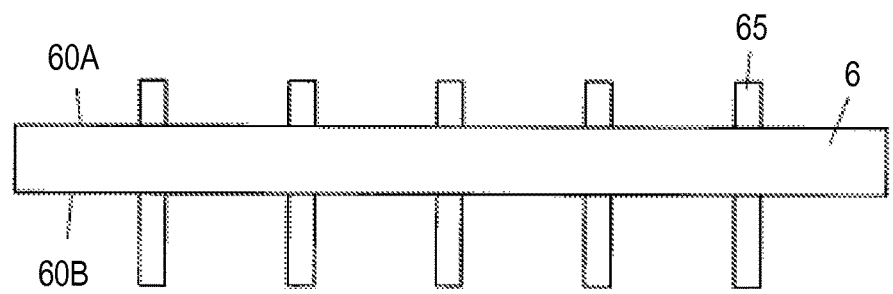
FIG. 4 is an explanatory side view illustrating the essential part of the device according to the first exemplary embodiment.
Figure 5:
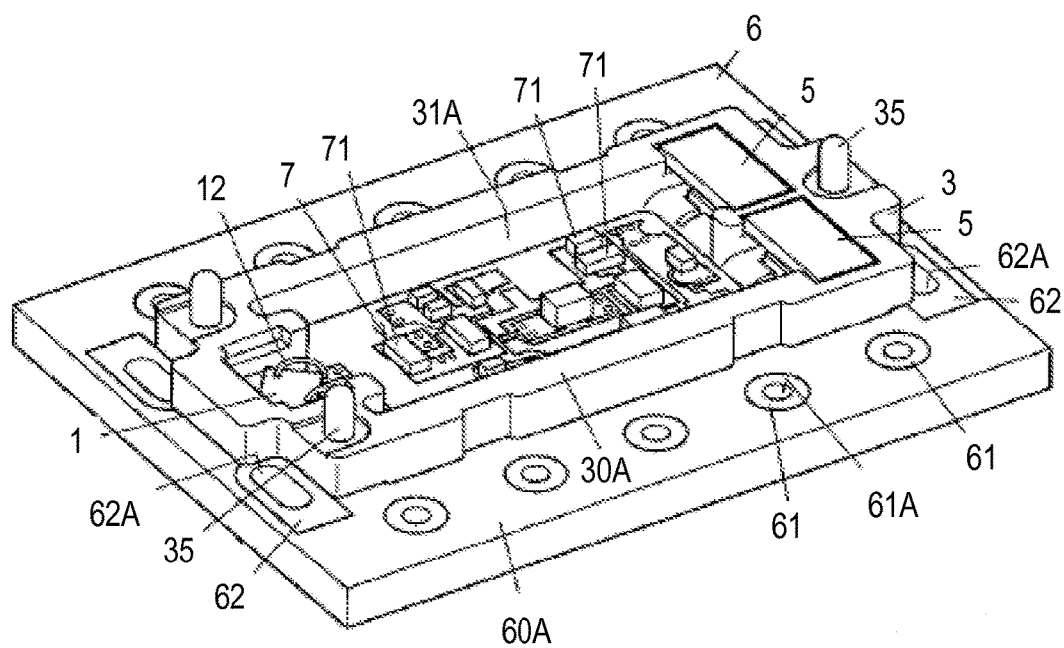
FIG. 5 is an explanatory perspective view illustrating the essential part of the device according to the first exemplary embodiment.

According to device 10 in this exemplary embodiment, board 6 has conductor wiring 61 for outputting signals from light receiving elements 2 to the outside and wiring 63 electrically connected to conductor wiring 61. Conductor wiring 61 is electrically connected to wiring 63 formed on front surface 60A of board 6. Board 6 is provided with through holes 61A (see FIG. 2) into which metal terminals 65 (see FIGS. 3 and 4) can be inserted. Terminals 65 are provided for outputting signals received from light receiving elements 2. In board 6, metal terminals 65 inserted into through holes 61A are electrically connected to conductor wiring 61 via not-shown soldering or the like.

According to device 10 of this exemplary embodiment, device 10 of different mount configuration can be manufactured only by replacing board 6 containing conductor wiring 61 with board 6 having a different configuration.

This structure allows standardization of components constituting device 10, and increases a degree of freedom for electric connection between device 10 and an external apparatus provided outside device 10 for each type of apparatuses on which device 10 of this exemplary embodiment is mounted.

A method for manufacturing device 10 according to this exemplary embodiment is hereinafter described with reference to FIGS. 1 through 9.

According to the method for manufacturing device 10, electronic parts 71 are mounted on board 6. According to the method for manufacturing device 10, electronic parts 71 constituting signal processing circuit unit 7 are soldered to wiring 63 of board 6 by flow soldering or other methods. Frame-shaped support body 3 is positioned on board 6 so as to surround an area where electronic parts 71 are mounted. Light emitting element 1 and light receiving elements 2 may be mounted on the one surface 30A side of support body 3 in advance. According to the method for manufacturing device 10, support body 3 and board 6 are aligned by insertion of projections (not shown) projecting from support body 3 toward the board 6 side into holes 63A (see FIG. 3) of board 6.

When an automatic assembling device (not shown) is used in the method for manufacturing device 10, mounting positions of light emission element 1 and light receiving elements 2 are determined by performing an imaging process (such as edge detection) for an image of support body 3 imaged by an imaging device of the automatic assembling device. In device 10, cross-shaped groove 33A (see FIG. 2) is formed in an inner bottom surface of first recess 33 of support body 3. According to the method for manufacturing device 10, the mounting position of light emitting element 1 may be determined with reference to an edge of groove 33A. According to device 10, cross-shaped groove 34A is formed in each inner bottom surface of second recesses 34 of support body 3. According to device 10, each of the mounting positions of light receiving elements 2 may be determined with reference to an edge of corresponding groove 34A. According to the method for manufacturing device 10, light emitting element 1 is mounted on the inner bottom surface of first recess 33 of support body 3 via a die bond material such as epoxy resin. Similarly, according to the method for manufacturing device 10, light receiving elements 2 are mounted on the inner bottom surfaces of second recesses 34 of support body 3 via die bond materials such as epoxy resin, respectively. According to the method for manufacturing device 10, metal wire 12 electrically connect the wiring 63 side formed on front surface 60A of board 6 to light emitting element 1. According to the method for manufacturing device 10, wiring 63 formed on front surface 60A of board 6 is electrically connected to light receiving elements 2 by wire bonding using metal wire. According to the method for manufacturing device 10, optical filters 5 are disposed on the pair of steps 32A formed in the inner walls of each of second recesses 34 of support body 3 in such a condition that optical filters 5 cover corresponding light receiving elements 2 (see FIG. 5).

Figure 6:
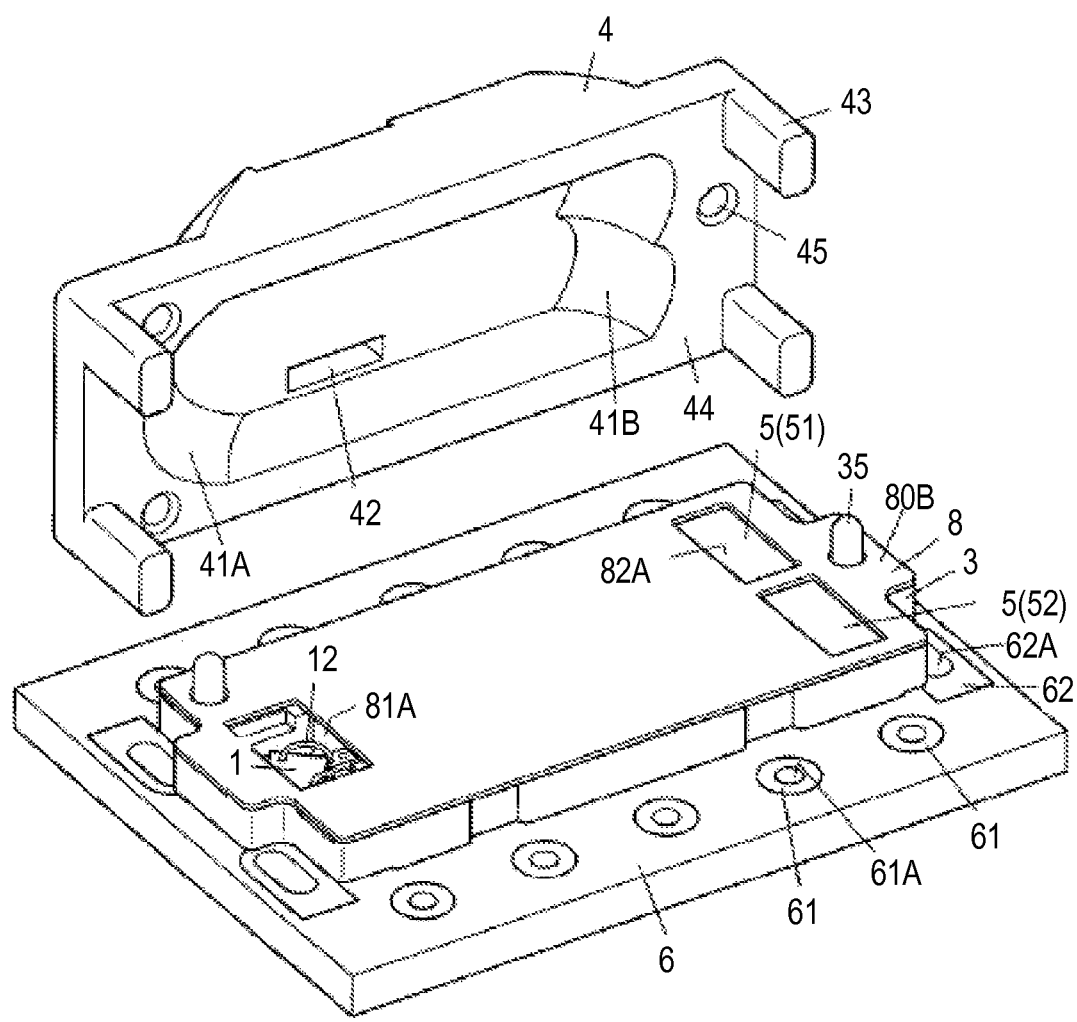
FIG. 6 is an exploded perspective view illustrating the essential part of the device according to the first exemplary embodiment.
Figure 7:
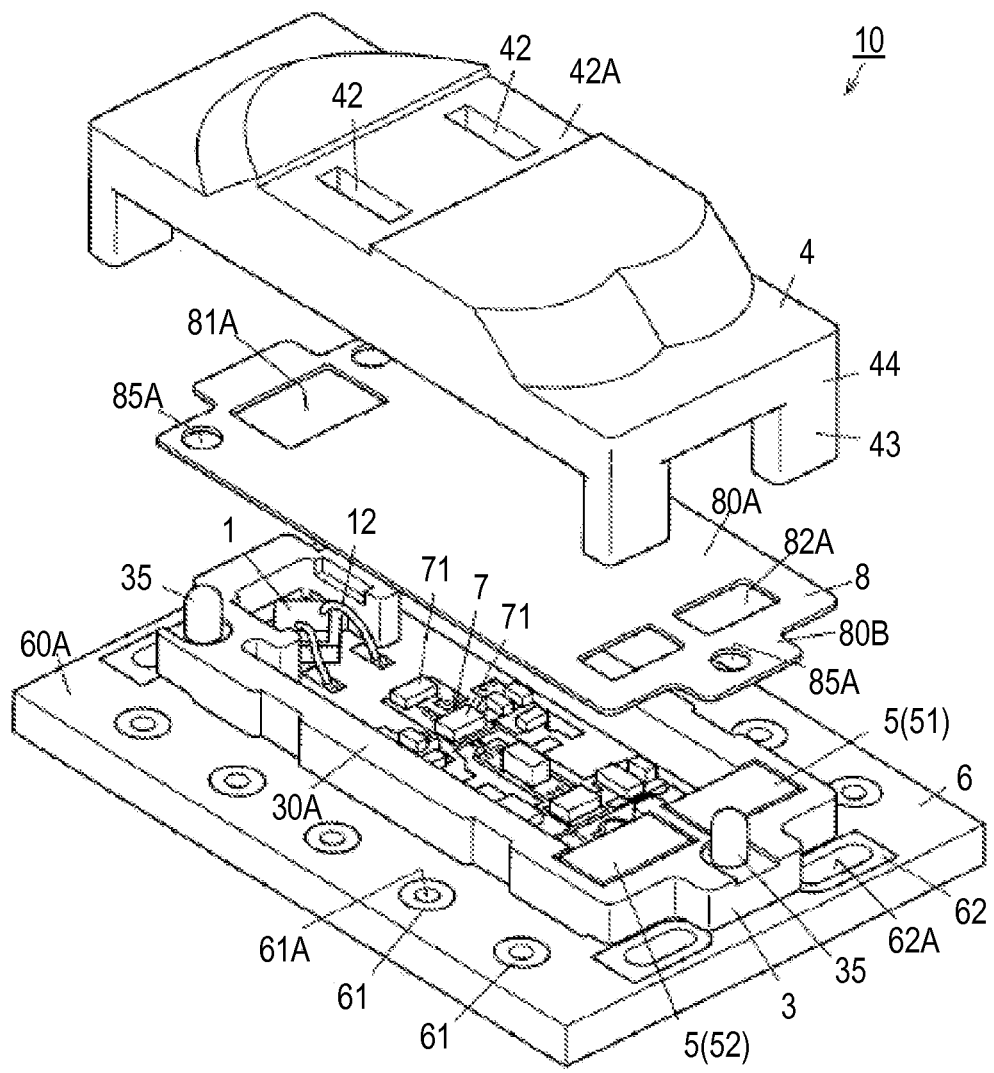
FIG. 7 is an exploded perspective view illustrating the essential part of the device according to the first exemplary embodiment.
Figure 8:
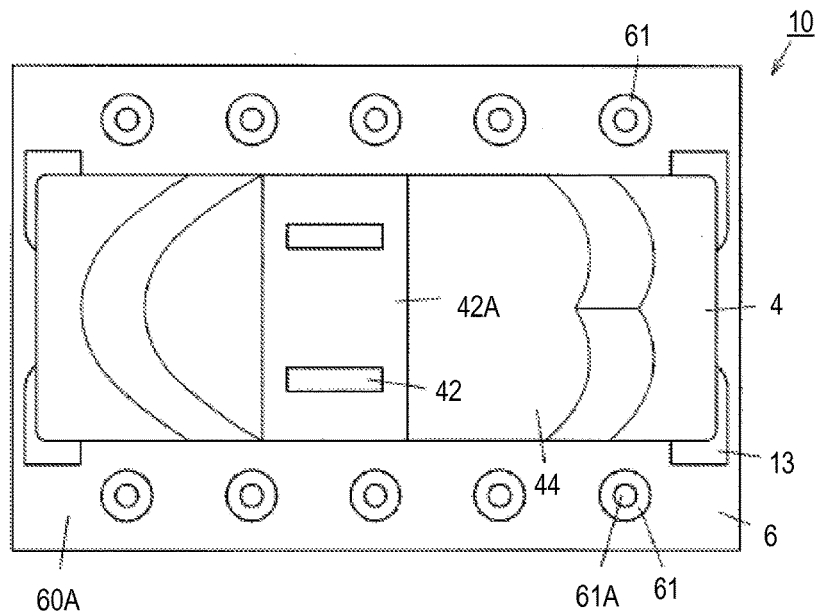
FIG. 8 is a plan view illustrating the essential part of the device according to the first exemplary embodiment.
Figure 9:
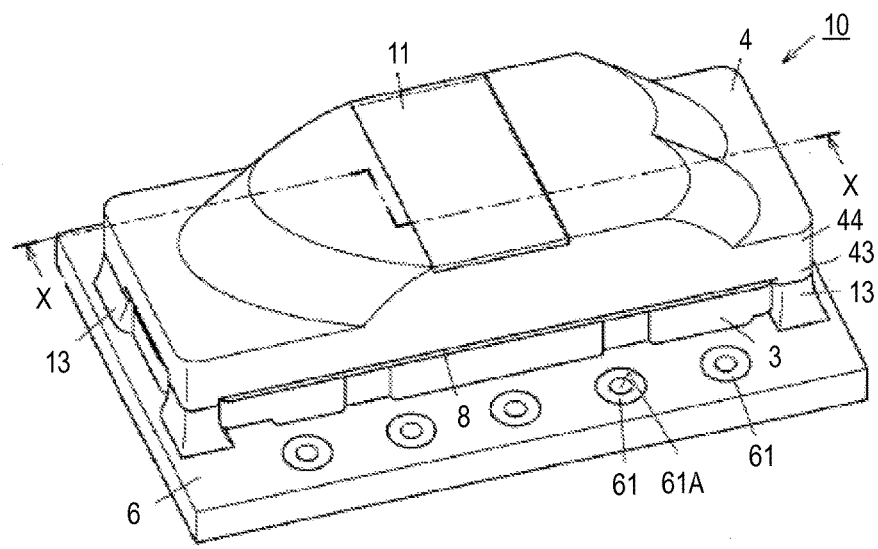
FIG. 9 is a perspective view illustrating an external appearance of the device according to the first exemplary embodiment.

According to the method for manufacturing device 10, next, reflection body 8 is positioned on support body 3 on which optical filters 5 are disposed (see FIG. 6). According to the method for manufacturing device 10, support body 3 and reflection body 8 are aligned by insertion of engagement projections 35 projecting from support body 3 toward the optical member 4 side into through holes 85A of reflection body 8. According to the method for manufacturing device 10, first opening 81A and light emitting element 1 can be aligned by alignment between support body 3 and reflection body 8. In addition, according to the method for manufacturing device 10, second openings 82A and light receiving elements 2 can be aligned by alignment between support body 3 and reflection body 8.

Subsequently, according to the method for manufacturing device 10, projections 43 projecting from optical member 4 toward the board 6 side are inserted into insertion holes 62A of board 6 (see FIGS. 7 and 8), so that optical member 4 is overlaid on board 6 with support body 3 interposed therebetween. According to the method for manufacturing device 10, projections 43 of optical member 4 are joined to lands 62 formed around insertion holes 62A by soldering. In device 10, projections 43 of optical member 4 are joined to lands 62 around insertion holes 62A by soldering 13 (see FIG. 9). FIG. 1 is a view illustrating a cross section taken along a 1-1 plane in FIG. 9.

In device 10, optical member 4 having outside surface 40B coated with metal material is electrically connected with lands 62 around insertion holes 62A of board 6. In device 10, lands 62 around insertion holes 62A of board 6 are grounded. In other words, optical member 4 is a resin molded component whose outside surface 40B is coated with metal portion 44 made of metal material which is electrically connected to the ground of board 6.

According to device 10, a potential of optical member 4 coated with metal portion 44 of metal material may be set to a reference potential. In this case, device 10 can prevent generation of noise in electronic parts 71 or the like provided on board 6 covered by optical member 4. The noise may result from entrance of electromagnetic waves from the outside of device 10. Similarly, according to device 10, a potential of reflection body 8 contacting optical member 4 is allowed to be set to the reference potential in accordance with setting of the potential of optical member 4 coated with metal portion 44 of metal to the reference potential. By setting the potential of reflection body 8 to the reference potential, in device 10, it can be further suppress to generate noise in electronic parts 71 or the like provided on board 6 covered by reflection body 8. The noise may result from entrance of electromagnetic waves from the outside of device 10.

According to device 10 in this exemplary embodiment, metal terminals 65 are inserted into through holes 61A of board 6. According to device 10, conductor wiring 61 formed around through holes 61A of board 6 is electrically connectable to metal terminals 65 via soldering (not shown) or the like. Device 10 is electrically connectable with an external apparatus via metal terminals 65. According to device 10, patterns of conductor wiring 61 formed on board 6 are allowed to vary relatively easily in comparison with a device which has terminals formed by insert molding of resin material, for outputting signals received from light receiving elements 2 to the outside. Device 10 preferably includes screw holes 60C for receiving screws or the like fixing device 10 to a wiring board (not shown) of an external apparatus.

In device 10 according to this exemplary embodiment, optical member 4 is optically coupled with support body 3 on which light emitting element 1 and light receiving elements 2 are mounted as elements requiring relatively high alignment accuracy. In addition, in device 10, optical member 4 is fixed to board 6 which does not require relatively high alignment accuracy with support body 3 and optical member 4 in comparison with the optical coupling. According to device 10, conductor wiring 61 for outputting signals received from the light receiving elements 2 side to the outside is provided on board 6 which does not require relatively high alignment accuracy, and therefore a degree of freedom of electric connection to the outside further can increase. In other words, in device 10 according to this exemplary embodiment, support body 3 which holds light emitting element 1 and light receiving elements 2 with a predetermined distance therebetween is functionally separated from board 6 which includes conductor wiring 61 for outputting signals to the outside, in accordance with accuracy of alignment.

Device 10 according to this exemplary embodiment is applicable to a gas sensor equipped on an air conditioner, a gas detection alarm, a vehicle exhaust gas measuring device, alcohol detector or the like, for example.

The respective components included in device 10 according to this exemplary embodiment are hereinafter described in more detail.

Light emitting element 1 is capable of emitting infrared light. Light emitting element 1 may be constituted by a semiconductor bare chip. Light emitting element 1 is not limited to a semiconductor bare chip, but may be a chip size package. Light emitting element 1 may be constituted by a light emitting diode chip, or a resistance element or a laser diode provided on a semiconductor substrate, for example. Light emitting element 1 is capable of emitting infrared light having a wavelength easily absorbable by a detection target gas. Light emitting element 1 can be electrically connected to wiring 63 formed on board 6 by an appropriate method such as wire bonding. Reduction of the entire size of device 10 is achievable when light emitting element 1 is constituted by a semiconductor bare chip, in comparison with a device which uses a package type light emitting diode.

Light receiving elements 2 are capable of receiving infrared light and converting the infrared light into electric signals. Light receiving elements 2 may be constituted by semiconductor bare chips. Light receiving elements 2 are not limited to semiconductor bare chips, but may be chip size packages. Light receiving elements 2 may be constituted by pyroelectric elements or photodiode chips, for example. Light receiving elements 2 can be electrically connected to wiring 63 formed on board 6 by an appropriate method such as wire bonding. Reduction of the entire size of device 10 is achievable when light receiving elements 2 are constituted by semiconductor bare chips, in comparison with a device which uses package type photodiodes.

Support body 3 is capable of supporting light emitting element 1 and light receiving elements 2 with a predetermined distance therebetween. Support body 3 may have a frame-shaped external appearance. Support body 3 is capable of accommodating electronic parts 71 mounted on board 6 within opening 31A of frame-shaped support body 3. Support body 3 may be a resin molded component formed by a synthetic resin molded body. Support body 3 may be made of polyphthalamide resin, for example. Support body 3 has steps 32A on which optical filters 5 can be positioned so as to cover light receiving elements 2. To support body 3, reflection body 8 may be positioned in such a manner to cover opening 31A of frame-shaped support body 3. Reflection body 8 may be provided with a fourth optical path changing portion corresponding to a reflection mirror which reflects infrared light so as to guide the light from the first optical path changing portion 41A side to the second optical path changing portion 41B side. Reflection body 8 is capable of closing a part of opening 31A of frame-shaped support body 3. Support body 3 is capable of increasing light utilization efficiency by covering opening 31A of frame-shaped support body 3 and supporting reflection body 8 which reflects infrared light toward space 40A.

Optical member 4 is capable of guiding infrared light from light emitting element 1 toward light receiving elements 2. Optical member 4 is capable of covering one surface 30A side of support body 3 with interposed therebetween. The detection target gas is introducible into space 40A. Optical member 4 may be a resin molded component formed by a synthetic resin molded body. Optical member 4 may be made of polyphthalamide resin, for example. Optical member 4 is not limited to a resin molded component, but may be made of metal material. Optical member 4 constituted by a resin molded component has a more accurate external appearance than a component made of metal material. It is preferable that outside surface 40B of optical member 4 is coated with metal material when optical member 4 is formed as a resin molded component. Optical member 4 may have a rectangular parallelepiped shape having an external size equivalent to the external size of support body 3 in the plan view. Optical member 4 is allowed to be fixed to board 6 in such a manner that a recess of optical member 4 faces board 6 via support body 3. Optical member 4 may have air holes 42 penetrating optical member 4 in the direction of the thickness of optical member 4. Optical member 4 is capable of introducing and discharging the detection target gas into and out of space 40A through air holes 42. It is preferable that air holes 42 of optical member 4 are covered by dust filters 11 to prevent entrance of foreign material other than the outside air, such as dust, into air holes 42. Each of air holes 42 may have a rectangular shape in the plan view, for example. Each shape of air holes 42 is not limited to a rectangular shape, but may have other shapes such as a circular shape in the plan view. The number of air holes 42 is not required to be two. The number of air holes 42 may be one, three or a larger number.

Optical member 4 may include the first reflection mirror constituting first optical path changing portion 41A, the second reflection mirror constituting second optical path changing portion 41B, and the third reflection mirror constituting third optical path changing portion 41C. Optical member 4 may include metal material such as gold and aluminum formed by deposition or plating on the inner surface of the recess of optical member 4. Third optical path changing portion 41C may have a semi-cylindrical shape at both ends of which first optical path changing portion 41A and second optical path changing portion 41B are provided.

The reflection surface of first optical path changing portion 41A is not limited to a parabolic surface. First optical path changing portion 41A may have a reflection surface having a flat shape, a spherical shape, or a polygonal shape. The reflection surface of second optical path changing portion 41B is not limited to a parabolic surface. Second optical path changing portion 41B may have a reflection surface having a flat shape, a spherical shape, or a polygonal shape. When the reflection surface of second optical path changing portion 41B of device 10 is made to be a concave surface, light reflected on the reflection surface of second optical path changing portion 41B is allowed to be converged. In this case, light receiving elements 2 can efficiently receive infrared light.

Figure 10:
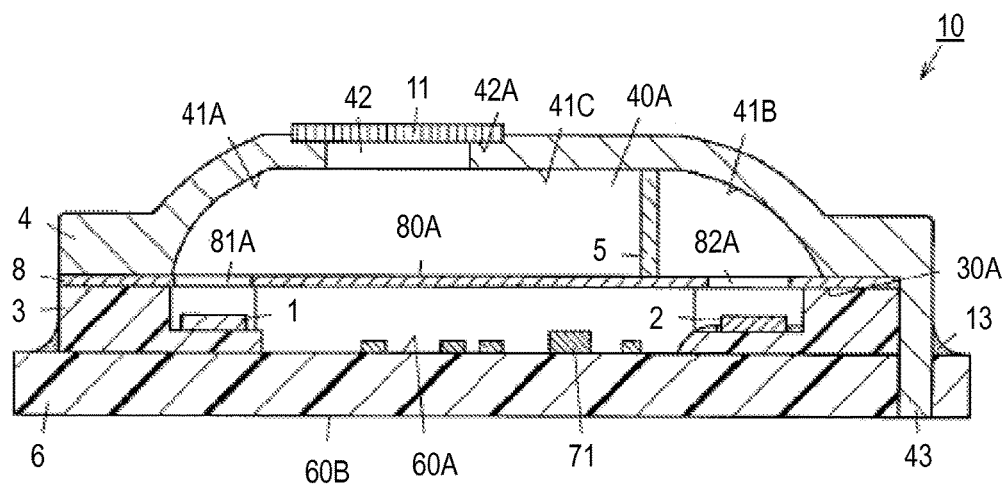
FIG. 10 is a cross-sectional view schematically illustrating another device according to the first exemplary embodiment.

Each of optical filters 5 is capable of transmitting infrared light having a predetermined wavelength band. Each of optical filters 5 constitutes a band pass filter which has a transmission band containing a wavelength band of a wavelength of infrared light emitted from light emitting element 1. Each of optical filters 5 may be formed of an interference filter having a multilayered structure of dielectric films, for example. Examples of a base material of each of optical filters 5 include Ge, Si and other semiconductor materials, and methacrylic resin. Optical filters 5 may be disposed on steps 32A of support body 3. Optical filters 5 may be fixed to steps 32A of support body 3 via bonding material (not shown). Optical filters 5 may be fixed to reflection body 8 via bonding material. Optical filters 5 may be fixed to light receiving elements 2 via bonding material. The bonding material employed herein may be made of glass having a low melting point, alloy having a low melting point, and resin material, for example. According to device 10 in this exemplary embodiment, optical filters 5 may be provided on optical member 4 between first optical path changing portion 41A and second optical path changing portion 41B as illustrated in FIG. 10. In other words, optical filters 5 are only required to be disposed on the optical path of infrared light from light emitting element 1 toward the light receiving elements 2 side.

Board 6 can be coupled with optical member 4 via support body 3. Board 6 may have a rectangular flat-plate external shape, for example. The shape of board 6 is not limited to a rectangular flat-plate shape, but may be various shapes such as a circular shape and a polygonal shape. Board 6 may be formed of a glass epoxy resin substrate, or a ceramic multi-layered substrate, for example. Electronic parts 71 constituting signal processing circuit unit 7 may be mounted on board 6, for example. Board 6 includes wiring 63. Board 6 includes conductor wiring 61 capable of being electrically connected to wiring 63. Conductor wiring 61 is capable of being electrically connected to light receiving elements 2 and electronic parts 71 constituting signal processing circuit unit 7 by using wiring 63, so as to output signals from light receiving elements 2.

Figure 11:
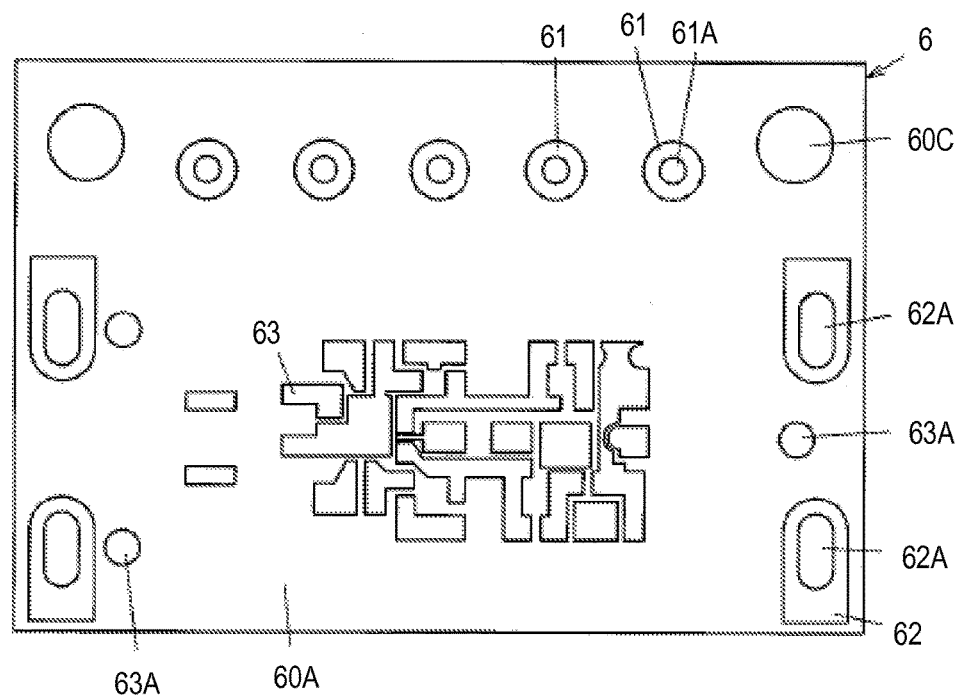
FIG. 11 is a plan view illustrating an essential part of a still other device according to the first exemplary embodiment.
Figure 12:
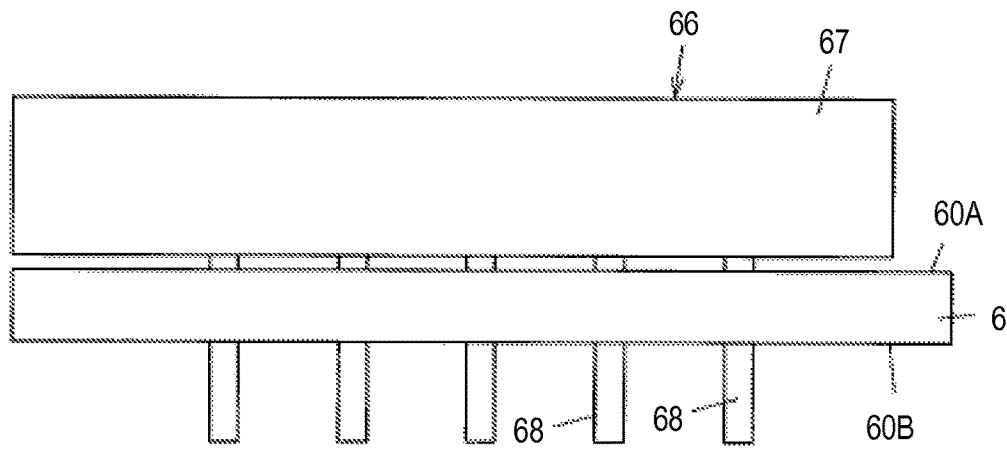
FIG. 12 is an explanatory side view illustrating the essential part of the still other device according to the first exemplary embodiment.

Board 6 is provided with through holes 61A penetrating board 6. In board 6, conductor wiring 61 around through holes 61A is capable of being electrically connected, via soldering (not shown) or the like, to metal terminals 65 by inserting metal terminals 65 into through holes 61A. Device 10 is allowed to be mounted on a wiring board (not shown) of an external apparatus by use of metal terminals 65. Similarly, device 10 including board 6 as illustrated in FIG. 11 is allowed to include receptacle 66 which contains contact pins 68 within connector body 67 formed by insulation material (see FIG. 12), instead of the use of metal terminals 65. In device 10, contact pins 68 of receptacle 66 are electrically connected to conductor wiring 61. According to device 10, conductor wiring 61 is capable of being electrically connected, via receptacle 66, to a plug electrically connected with a wiring board on the apparatus side.

Figure 13:
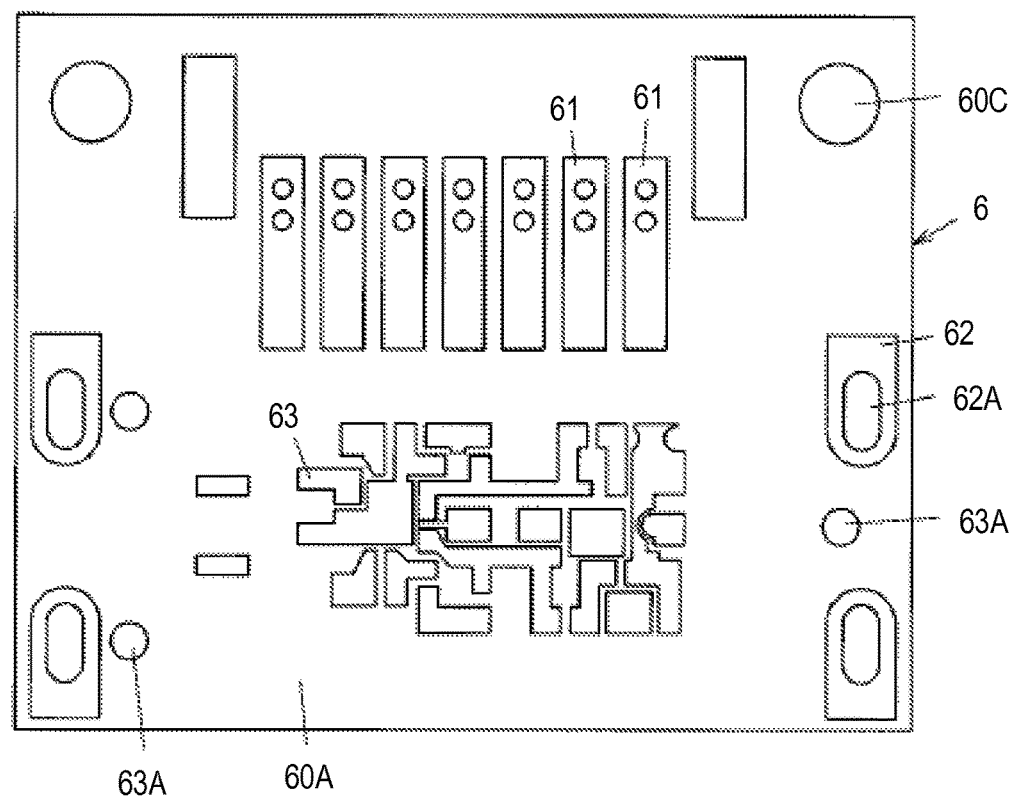
FIG. 13 is a plan view illustrating an essential part of a further other device according to the first exemplary embodiment.
Figure 14:
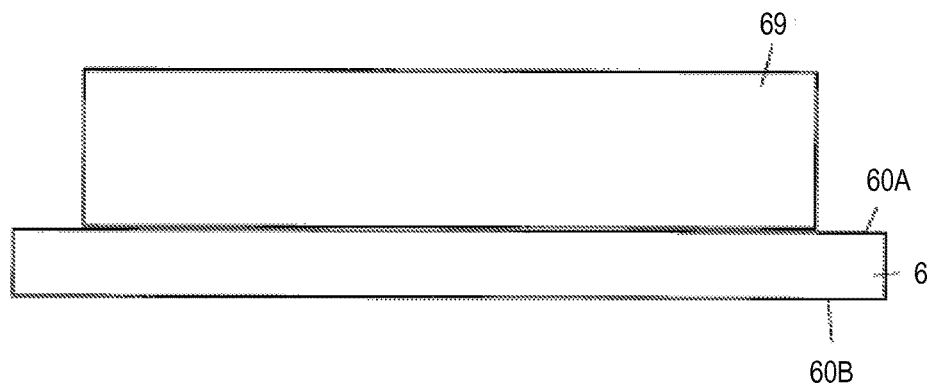
FIG. 14 is an explanatory side view illustrating the essential part of the further other device according to the first exemplary embodiment.

Alternatively, surface mounting type receptacle 69 may be surface-mounted on conductor wiring 61 via soldering or the like, instead of the use of metal terminals 65 as in device 10 including board 6 as illustrated in FIG. 13 (see FIG. 14). Device 10 is capable of being electrically connected to the wiring board on the apparatus side by using metal terminals 65, receptacle 66, or receptacle 69.

Signal processing circuit unit 7 is configured to allow emission of infrared light from light emitting element 1 by controlling light emitting element 1. Signal processing circuit unit 7 is configured to process signals output from light receiving elements 2 upon receiving infrared light. Signal processing circuit unit 7 may perform signal processing such as amplification, waveform shaping, signal sampling, and signal A/D conversion of signals output from light receiving elements 2. Signal processing circuit unit 7 may further perform signal processing such as signal calculation, signal correction, and determination that the detection target gas has an abnormal concentration, for example. Signal processing circuit unit 7 may be formed of electronic parts 71 such as integrated circuits.

Reflection body 8 is capable of reflecting infrared light toward space 40A. Reflection body 8 may be a flat-shaped plate component made of metal material. Examples of material of reflection body 8 include metal material such as aluminum. Reflection body 8 is made of metal, and electrically connectable with metal portion 44 made of metal as a portion of optical member 4. Reflection body 8 may include the fourth optical path changing portion capable of reflecting infrared light, and having a smooth surface on the side facing optical member 4. Reflection body 8 is not required to be made of metal material, but may be formed of a resin molded component. Reflection body 8 may be a flat-plate-shaped member formed of a resin molded component on which gold, aluminum or other metal material is deposited or plated.

Second Exemplary Embodiment

Figure 15:
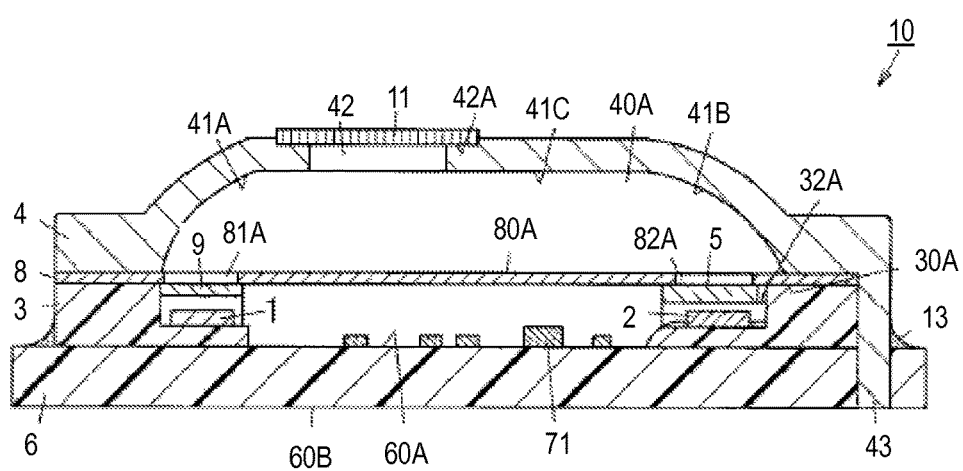
FIG. 15 is a cross-sectional view schematically illustrating a device according to a second exemplary embodiment.

Device 10 according to this exemplary embodiment illustrated in FIG. 15 is different from device 10 in the first exemplary embodiment chiefly in that cover member 9 closing first opening 81A is provided at first opening 81A of reflection body 8 in the first exemplary embodiment illustrated in FIG. 1. Constituent elements similar to corresponding constituent elements in the first exemplary embodiment are given similar reference numbers, and the same explanation is not repeated when omission of the explanation is appropriate.

Figure 16:
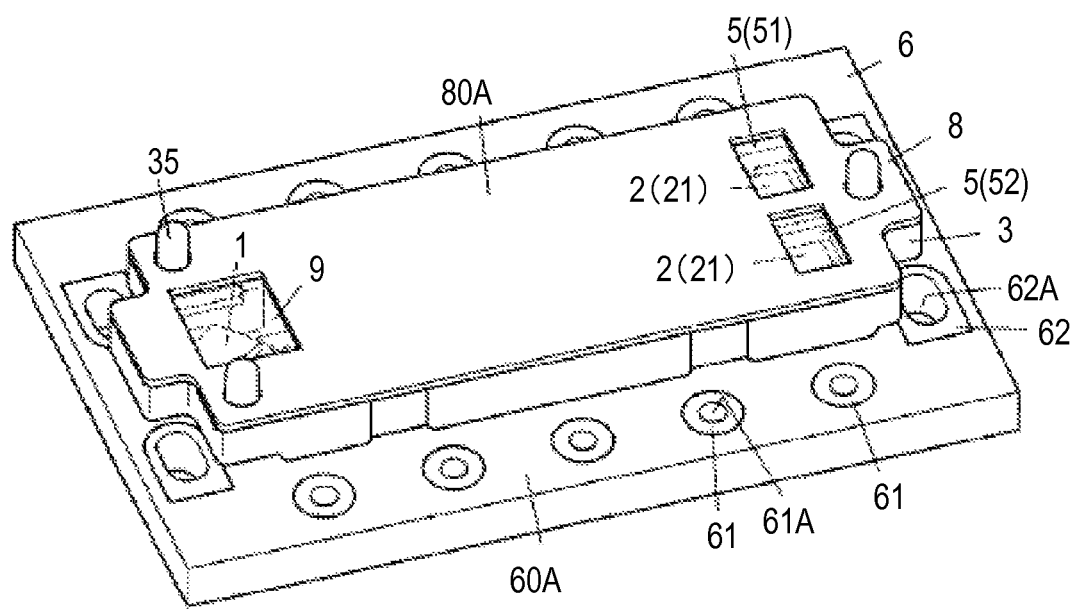
FIG. 16 is a perspective view illustrating an external appearance of an essential part of the device according to the second exemplary embodiment.

According to device 10 in this exemplary embodiment illustrated in FIGS. 15 and 16, reflection body 8 includes first opening 81A through which infrared light emitted from light emitting element 1 passes. Reflection body 8 includes second openings 82A through which infrared light to be received by light receiving elements 2 passes. In device 10, translucent cover member 9 closes first opening 81A. In device 10, optical filters 5 close second openings 82A, respectively. Translucent cover member 9 and optical filters 5 prevent air from flowing toward the light receiving elements 2 side from space 40A surrounded by reflection body 8, cover member 9, optical filters 5, and optical member 4. Optical filters 5 are considered to have translucency. Accordingly, cover member 9 is considered as a first translucent cover member, while optical filters 5 are considered as second translucent cover members.

While a configuration of each of light receiving elements 2 of device 10 is not shown in this exemplary embodiment, each of light receiving elements 2 may be constituted by a pyroelectric infrared sensor including a membrane formed of an insulation film on a cavity portion, and containing a pyroelectric element which includes a pyroelectric material sandwiched between electrodes on the insulation film, for example. This infrared sensor may be formed in an appropriate manner by using MEMS (Micro Electro Mechanical Systems) technology, for example.

According to device 10 in the first exemplary embodiment, there is a possibility that a detection target gas flows from the space 40A side toward the light receiving elements 2 side via first opening 81A. In addition, according to device 10, there is a possibility that a membrane of an infrared sensor is deformed by flow and pressure of the detection target gas from the space 40A side toward the light receiving elements 2 side. There is a possibility in device 10 that detection errors of the infrared sensor, or damage to the infrared sensor are caused when the membrane of the infrared sensor is deformed.

As device 10 in this exemplary embodiment includes optical filters 5, detection errors of the infrared sensor and damage to the infrared sensor caused by pressure of the detection target gas are suppressed even when each of light receiving elements 2 includes an infrared sensor containing a membrane.

Third Exemplary Embodiment

Device 10 according to this exemplary embodiment is different from device 10 according to the first exemplary embodiment in that three or more sets of optical filter 5 and light receiving element 2 are provided for one light emitting element 1, instead of two sets of optical filter 5 and light receiving element 2 for one light emitting element 1 as in the first exemplary embodiment illustrated in FIG. 1. Constituent elements similar to corresponding constituent elements in the first exemplary embodiment are given similar reference numbers, and the same explanation is not repeated when omission of the explanation is appropriate.

Figure 17:
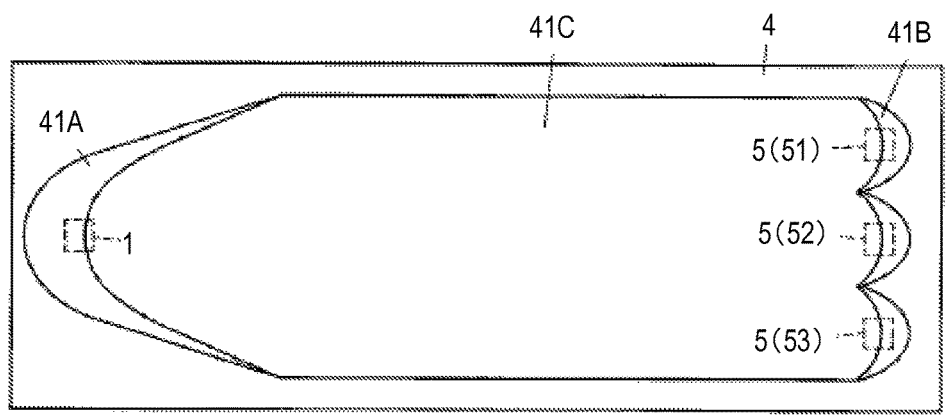
FIG. 17 is a bottom view illustrating an essential part of a device according to a third exemplary embodiment.
Figure 18:
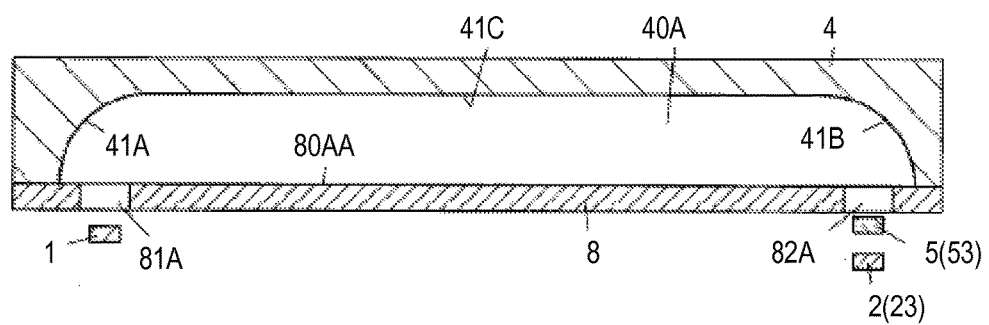
FIG. 18 is an explanatory cross-sectional view illustrating the device according to the third exemplary embodiment.

According to device 10 in this exemplary embodiment, optical filters 5 include first optical filter 51 which has a transmission band containing infrared light in a wavelength band absorbable by a detection target gas, and second optical filter 52 which has a transmission band different from that of first optical filter 51, as illustrated in FIGS. 17 and 18. Light receiving elements 2 include first light receiving element 21 which photoelectrically converts infrared light transmitted through first optical filter 51, and second light receiving element 22 which photoelectrically converts infrared light transmitted through second optical filter 52. Optical filters 5 further include third optical filter 53 which has a transmission band different from those of first optical filter 51 and second optical filter 52. Light receiving elements 2 further include third light receiving element 23 which photoelectrically converts infrared light transmitted through third optical filter 53.

This structure allows device 10 according to this exemplary embodiment to detect various types of gases. While device 10 according to the first exemplary embodiment is an example of a gas sensor for detecting a concentration of one type of gas contained in the outside air, device 10 including a plurality of sets of light receiving element 2 and optical filter 5 can detect concentrations of gases of different types for each set of light receiving element 2 and optical filter 5. Device 10 according to this exemplary embodiment includes three or more sets of light receiving element 2 and optical filter 5, and is thus capable of detecting concentrations of gases of different types based on outputs from respective light receiving elements 2.

Device 10 according to this exemplary embodiment includes first light receiving element 21 as light receiving element 2 for gas detection. Device 10 includes second light receiving element 22 as light receiving element 2 for gas detection. In device 10 in this exemplary embodiment, each of optical filters 5 constitutes a band pass filter which has a transmission band containing a wavelength corresponding to absorption characteristics of the detection target gas. Device 10 including a plurality of sets of light receiving element 2 for gas detection and optical filter 5 according to this embodiment is capable of detecting a plurality kind of gases. Device 10 according to this exemplary embodiment is capable of independently detecting concentrations of two different types of gases from a plurality of types of gases contained in the outside air. Device 10 according to this exemplary embodiment is capable of simultaneously detecting both of a first gas (such as carbon monoxide) and a second gas (such as nitrogen oxide) of two types of gases. Moreover, device 10 according to this exemplary embodiment includes third optical filter 53 which transmits a band not absorbed by either the first gas or the second gas. Third light receiving element 23 receives infrared light transmitted through third optical filter 53, and outputs a signal generated by photoelectric conversion to signal processing circuit unit 7. Signal processing circuit unit 7 measures a change ratio from initial output from light emitting element 1 based on the signal output from third light receiving element 23. According to device 10, signal processing circuit unit 7 having measured the change ratio from the initial output from light emitting element 1 corrects output from first light receiving element 21 and output from second light receiving element 22. Device 10 is capable of avoiding the effect by power deterioration of light emitting element 1 or the like, and improving measurement accuracy by correcting outputs from first light emitting element 21 and second light emitting element 22.

Fourth Exemplary Embodiment

Device 110 according to this exemplary embodiment is hereinafter described with reference to FIGS. 19A through 22.

Figure 19A:
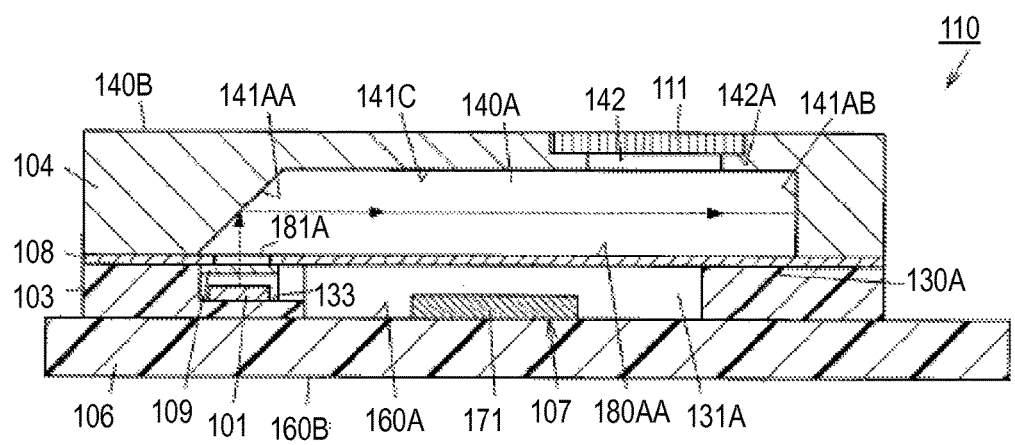
FIG. 19A is a cross-sectional view schematically illustrating a device according to a fourth exemplary embodiment.
Figure 19B:
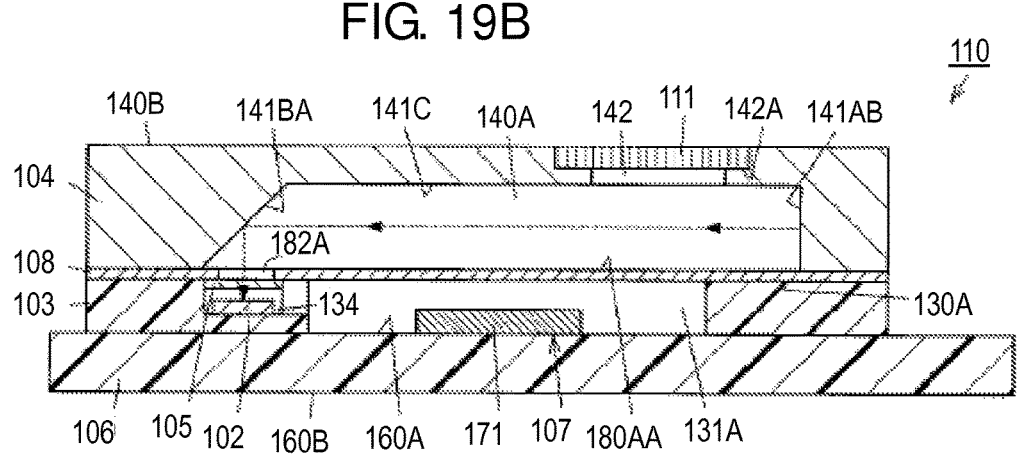
FIG. 19B is a cross-sectional view schematically illustrating the device taken along another cutting plane according to the fourth exemplary embodiment.
Figure 20:
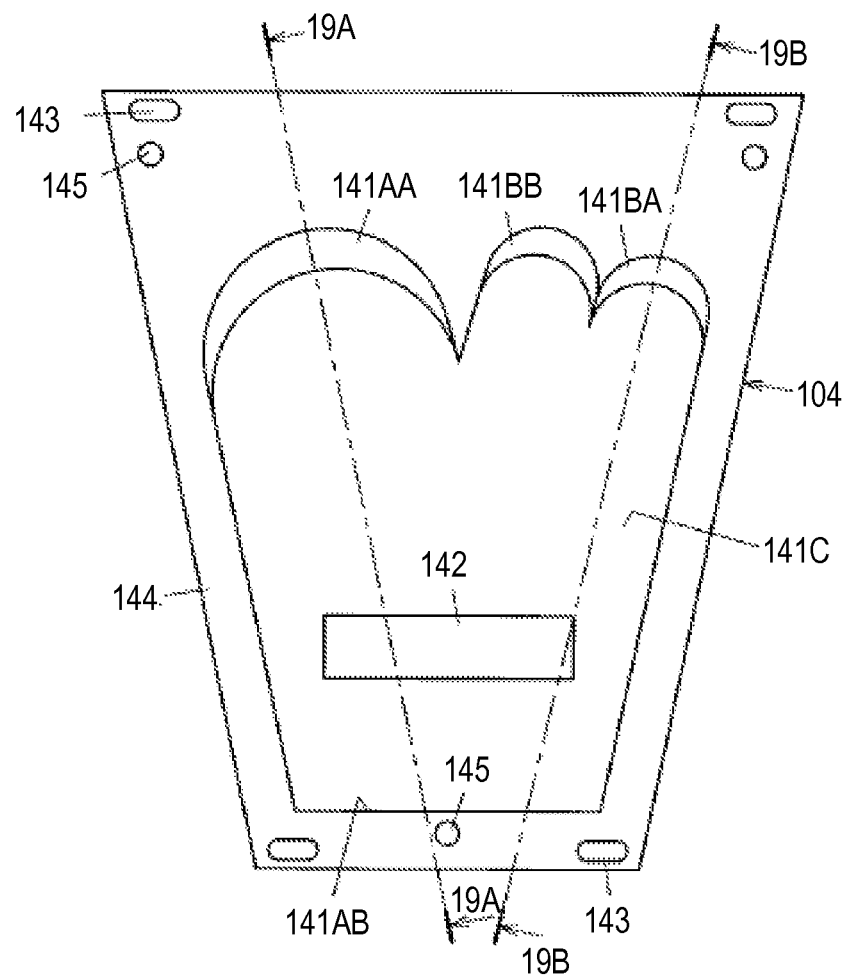
FIG. 20 is a bottom view illustrating an essential part of the device according to the fourth exemplary embodiment.

FIGS. 19A and 19B are cross-sectional views schematically illustrating device 10 according to a fourth exemplary embodiment, while FIG. 20 is a plan view illustrating an essential part of device 10 of the fourth exemplary embodiment. Device 110 according to this exemplary embodiment is a gas detecting device. Device 110 includes light emitting element 101, light receiving elements 102, signal processing circuit unit 107, optical member 104, and board 106. Signal processing circuit unit 107 processes signals output from light receiving elements 102. Optical member 104 covers light emitting element 101 and light receiving elements 102. Light emitting element 101, light receiving elements 102, signal processing circuit unit 107, and optical member 104 are mounted on board 106. Board 106 includes conductor wiring 161 electrically connected to light receiving elements 102 (see FIG. 21).

This structure increases a degree of freedom for electric connection between device 110 according to this exemplary embodiment and the outside.

Device 110 according to this exemplary embodiment includes light emitting element 101 for emitting infrared light (see FIG. 19A) and light receiving elements 102 for photoelectrically converting infrared light (see FIG. 19B). Device 110 includes support body 103 supporting light emitting element 101 and light receiving elements 102. Device 110 includes optical member 104 for guiding infrared light emitted from light emitting element 101 toward light receiving elements 102. Device 110 includes optical filters 105 disposed on optical paths (see arrows in FIG. 19A and FIG. 19B) for guiding infrared light from light emitting element 101 toward the light receiving elements 102 side. FIG. 19A is a cross-sectional view of device 110 illustrating a cross section taken along a line 19A-19A in FIG. 20. FIG. 19B is a cross-sectional view of device 110 illustrating a cross section taken along a line 19B-19B in FIG. 20.

In device 110, light emitting element 101 and light receiving elements 102 are disposed at one end of support body 103 on one surface 130A side of support body 103. Optical member 104 covers the one surface 130A side of support body 103 with space 140A interposed therebetween. A detection target gas is introducible into space 140A. Optical member 104 includes reflection mirror 141AB disposed at the other end of support body 103 on the side opposite to the one side of support body 103 to reflect infrared light emitted from light emitting element 101 disposed at the one side of support body 103 and guide the infrared light toward light receiving elements 102 disposed at the one end of support body 103.

This structure further reduces the size of device 110 in this exemplary embodiment.

A more specific configuration of device 110 according to this exemplary embodiment is hereinafter described.

In device 110 according to this exemplary embodiment, support body 103 is disposed on board 106. Support body 103 has a trapezoidal frame-like external shape in the plan view (see FIG. 21). Support body 103 is constituted by a resin molded component formed of a synthetic resin molded body. Board 106 has a rectangular flat-plate shape larger than the shape of support body 103. Board 106 is formed of a glass epoxy resin substrate. Board 106 has wiring of conductor patterns (not shown) on front surface 160A thereof. Board 106 includes rear surface 160B opposite to front surface 160A. According to device 110, electronic parts 171 are mounted on front surface 160A of board 106. Electronic part 171 is electrically connected with wiring via soldering (not shown). While only one electronic part 171 is shown in the figure according to device 110 in this exemplary embodiment, a plurality of electronic parts 171 may be mounted on board 106. Such a plurality of electronic parts 171 may be electrically connected with each other via wiring provided on board 106. Electronic part 171 constitutes signal processing circuit unit 107. According to device 110, signal processing circuit unit 107 may be constituted by a plurality of electronic parts 171. Signal processing circuit unit 107 is configured to allow emission of infrared light from light emitting element 101 by controlling light emitting element 101. Signal processing circuit unit 107 is configured to process signals output from light receiving elements 102 upon receiving infrared light. Signal processing circuit unit 107 performs signal processing such as amplification, waveform shaping, signal sampling, and signal analog/digital conversion of the signals output from light receiving elements 102. Signal processing circuit unit 107 further performs signal processing such as signal calculation, signal correction, and determination that the detection target gas has an abnormal concentration, for example. In device 110, signal processing circuit unit 107 is disposed within opening 131A of frame-shaped support body 103. In other words, electronic part 171 for processing signals output from light receiving elements 102 is mounted on board 106. According to device 110 structured such that electronic part 171 constituting signal processing circuit unit 107 is contained in opening 131A of frame-shaped support body 103, reduction of the entire size of device 110 is achievable.

In device 110, front surface 160A of board 106 is exposed to an inside of opening 131A of frame-shaped support body 103. Support body 103 is provided with first recess 133 at the one end of support body 103 on the one surface 130A side. Light emitting element 101 is mounted on an inner bottom surface of first recess 133 of support body 103. In device 110, light emitting element 101 is mounted on the inner bottom surface of first recess 133 via a die bond material (not shown). In device 110, the wiring formed on front surface 160A of board 106 and light emitting element 101 are electrically connected to each other by wire bonding using metal wire (not shown), for example. Light emitting element 101 is constituted by a light emitting diode capable of emitting infrared light. This light emitting diode is constituted by a semiconductor bare chip. Light emitting element 101 emits infrared light having a wavelength easily absorbed by a detection target gas. Examples of the detection target gas include carbon monoxide, carbon dioxide, methane, and nitrogen oxide. The structure of light emitting element 101 mounted on the inner bottom surface of first recess 133 of support body 103 is capable of reducing mutual thermal effect between light emitting element 101 and the signal processing circuit unit 107 side provided on board 106. Support body 103 is provided with second recesses 134 at the one end of support body 103 on the one surface 130A side. Light receiving elements 102 are mounted on inner bottom surfaces of second recesses 134 of support body 103, respectively. In device 110, light receiving elements 102 are mounted on the inner bottom surfaces of second recesses 134 via die bond materials (not shown). In Device 110, the wiring formed on front surface 160A of board 106 and light receiving elements 102 are electrically connected to each other by wire bonding using metal wire (not shown). Each of light receiving elements 102 includes an infrared sensor capable of receiving infrared light. Each of the infrared sensors is constituted by a pyroelectric element. Each of the infrared sensors is provided as a semiconductor bare chip. Support body 103 supports light emitting element 101 and light receiving elements 102 on the one surface 130A side.

Figure 21:
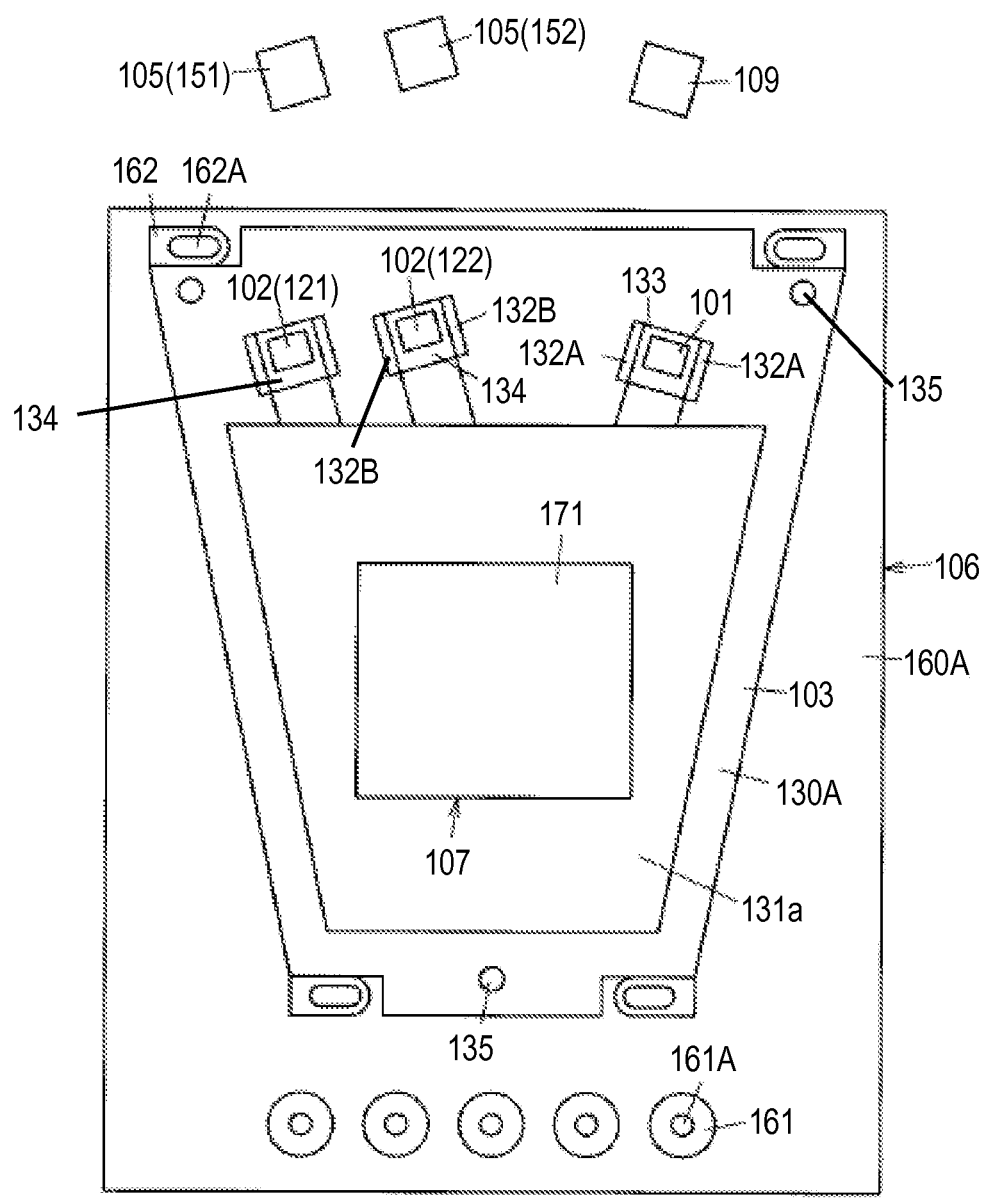
FIG. 21 is a plan view illustrating another essential part of the device according to the fourth exemplary embodiment.

Support body 103 has first steps 132A in opposed inner walls of first recess 133 (see FIG. 21). Cover member 109 is disposed on the pair of first steps 132A of support body 103 so as to cover light emitting element 101. First steps 132A are so sized that a depth of each thereof in a direction of a thickness of support body 103 is substantially equal to a thickness of cover member 109.

Support body 103 has second steps 132B in opposed inner walls of each of second recesses 134 (see FIG. 21). Optical filter 105 is disposed on each of the pair of second steps 132B of support body 103 so as to cover light receiving elements 102. Second steps 132B are so sized that each depth thereof in the direction of the thickness of support body 103 is substantially equal to the thickness of each of optical filters 105. Each of optical filters 105 is capable of constituting a band pass filter which has a transmission band containing a predetermined wavelength band in wavelengths of infrared light emitted from light emitting element 101.

In device 110 according to this exemplary embodiment, support body 103 is provided with the pair of second recesses 134 at the one end thereof on the one surface 130A side (see FIG. 21). Light receiving elements 102 are separately mounted on the inner bottom surfaces of second recesses 134 of support body 103, respectively. In device 110, optical filters 105 are separately disposed on corresponding light receiving elements 102 so as to cover the pair of light receiving elements 102. Hereinafter, the pair of light receiving elements 102 are referred to as first light receiving element 121 and second light receiving element 122 as well.

According to device 110 in this exemplary embodiment, one of optical filters 105 provided separately on corresponding light receiving elements 102 constitutes first optical filter 151 which has a transmission band containing a wavelength band of infrared light to be absorbed by the detection target gas. According to device 110, the other of optical filters 105 provided separately on corresponding light receiving elements 102 constitutes second optical filter 152 which does not have a transmission band containing the wavelength band of the infrared light to be absorbed by the detection target gas, but has a transmission band containing wavelengths around the wavelength band of the infrared light to be absorbed by the detection target gas.

In device 110 according to this exemplary embodiment, light emitting element 101, second light receiving element 122, and first light receiving element 121 are disposed on support body 103 in this order in the plan view.

Flat-plate-shaped reflection body 108 is mounted on the one surface 130A side of support body 103. Reflection body 108 may be formed of a trapezoidal flat-plate-shaped plate member in the plan view (see FIG. 22). Reflection body 108 includes surface 180AA formed into a smooth surface capable of reflecting infrared light. Reflection body 108 has first opening 181A through which infrared light emitted from light emitting element 101 can pass at one end thereof. Reflection body 108 is provided with through holes 185A at both ends of reflection body 108 on the one end side of reflection body 108. In addition, reflection body 108 has second openings 182A through which infrared light receivable by light receiving elements 102 passes at the one end of reflection body 108. Through hole 185A is formed at a center of the other end of reflection body 108. Reflection body 108 closes opening 131A of frame-shaped support body 103. In other words, support body 103 has a frame-shaped external appearance, and supports reflection body 108 which covers opening 131A of frame-shaped support body 103 and reflects infrared light toward space 140A.

Device 110 according to this exemplary embodiment includes optical member 104 covering one surface 130A of support body 103 on which reflection body 108 is mounted. Optical member 104 is a resin molded component formed of a synthetic resin molded body. Optical member 104 includes a metal portion (not shown) formed throughout outside surface 140B thereof by gold-plating. Optical member 104 constitutes a cover which covers the one surface 130A side of support body 103 supporting light emitting element 101 and light receiving elements 102. Optical member 104 has a trapezoidal shape which has an external size substantially equal to that of support body 103. Optical member 104 is provided with a recess opened to the support body 103 side. According to device 110, the recess of optical member 104 forms space 140A into which the detection target gas is introducible.

As illustrated in FIG. 19A, optical member 104 includes first reflection mirror 141AA disposed at the one end of support body 103 for reflecting infrared light emitted from light emitting element 101 in a predetermined direction. First reflection mirror 141AA constitutes a first optical path changing portion of optical member 104. Optical member 104 includes reflection mirror 141AB as a second reflection mirror disposed at the other end of support body 103 for reflecting again the infrared light coming from the first reflection mirror 141AA side toward the one end side of support body 103. Reflection mirror 141AB as the second reflection mirror constitutes a second optical path changing portion of optical member 104. Optical member 104 includes third reflection mirror 141BA disposed at the one end side of support body 103 for reflecting the infrared light coming from reflection mirror 141AB in a predetermined direction as illustrated in FIG. 19B. Third reflection mirror 141BA constitutes a third optical path changing portion of optical member 104. Optical member 104 includes fourth reflection mirror 141C disposed on a bottom surface of the recess of optical member 104 and capable of reflecting and guiding infrared light from the first reflection mirror 141AA side toward the third reflection mirror 141BA side via reflection mirror 141AB. Fourth reflection mirror 141C constitutes a fourth optical path changing portion of optical member 104.

Figure 23:
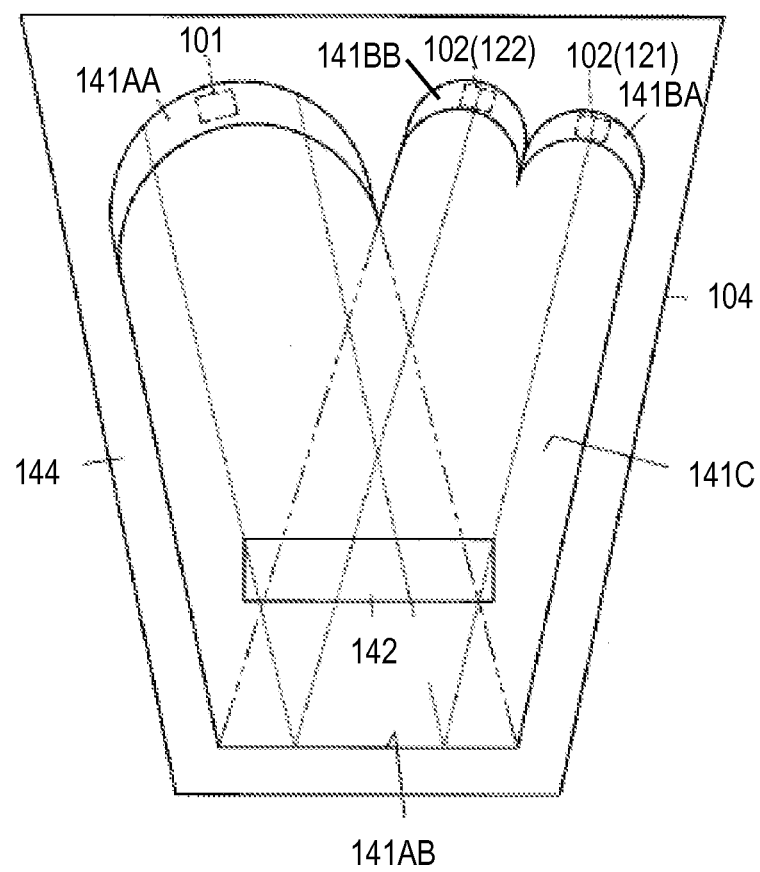
FIG. 23 is an explanatory operational view explaining operation of the device according to the fourth exemplary embodiment.

First reflection mirror 141AA may include a reflection surface having a parabolic shape. First reflection mirror 141AA changes the direction of the optical path of infrared light emitted from light emitting element 101 into the predetermined direction perpendicular to the direction of the thickness of support body 103. Reflection mirror 141AB as the second reflection mirror faces first reflection mirror 141AA, and may include a reflection surface having a smooth and flat shape. Third reflection mirror 141BA changes the direction of the optical path of the infrared light of which optical path is changed by first reflection mirror 141AA and reflection mirror 141AB into a direction crossing light receiving surfaces of light receiving elements 102. Optical member 104 includes third reflection mirror 141BB in correspondence with second light receiving element 122 similarly to third reflection mirror 141BA provided in correspondence with first light receiving element 121 (see FIG. 20). According to device 110, optical member 104 changes the optical path of the infrared light extending from light emitting element 101 to light receiving elements 102 (see broken lines in FIG. 23) into a V shape as illustrated in FIG. 23.

Device 110 in this exemplary embodiment can be smaller in comparison with a device in an example which does not include optical member 104 containing reflection mirror 141AB, but includes an optical member forming an optical path for linear emission of infrared light from light emitting element 101 toward the light receiving elements 102 side facing light emitting element 101. According to device 110 in this exemplary embodiment, optical member 104 includes reflection mirror 141AB, and therefore an area of the optical path of the infrared light indicated by two-dot chain lines in FIG. 23 decreases in correspondence with a portion of the optical path of the infrared light folded by reflection mirror 141AB, in comparison with the foregoing device which includes the optical member having the optical path for linear emission.

The structure of optical member 104 including first reflection mirror 141AA, reflection mirror 141AB, third reflection mirrors 141BA and 141BB, and fourth reflection mirror 141C allows infrared light emitted from light emitting element 101 to be guided toward the light receiving elements 102 side. Optical member 104 is provided with air hole 142 which penetrates optical member 104 in the direction of the thickness thereof. Air hole 142 has a rectangular shape in the plan view. Optical member 104 is capable of introducing the detection target gas into space 140A through air hole 142. Dust filter 111 is provided on accommodation recess 142A of optical member 104 so as to cover air hole 142 of optical member 104. Dust filter 111 prevents dust or other foreign material from entering into air hole 142. Dust filter 111 is fixed to accommodation recess 142A via a not-shown adhesive. Optical member 104 has rectangular parallelepiped projections 143 (see FIG. 20) projecting toward the board 106 side on surface 144 of optical member 104 at four corners of the trapezoidal shape of optical member 104, respectively. Support body 103 has engaging projections 135 (see FIG. 21) projecting toward the optical member 104 side on one surface 130A thereof. Each of engaging projections 135 may include a semispherical tip, and have a cylindrical shape on the whole, for example. Support body 103 has a pair of engaging projections 135 projecting toward the optical member 104 side at the one end of support body 103 on one surface 130A. Support body 103 has one engaging projection 135 projecting toward the optical member 104 side at a center of the other end of support body 103 on one surface 130A. Optical member 104 is provided with engaging holes 145 (see FIG. 20) for engaging with engaging projections 135 of support body 103.

According to device 110, support body 103 can be positioned with respect to optical member 104 by engagement between engaging projections 135 and engaging holes 145. According to device 110, alignment between light emitting element 101 and first reflection mirror 141AA is facilitated by use of engaging projections 135 and engaging holes 145. According to device 110, alignment between first light receiving element 121 and third reflection mirror 141BA is facilitated by use of engaging projections 135 and engaging holes 145. According to device 110, alignment between second light receiving element 122 and third reflection mirror 141BB is facilitated by use of engaging projections 135 and engaging holes 145. Device 110 is allowed to position light emitting element 101 at a focus of the parabolic reflection surface of first reflection mirror 141AA by engagement between support body 103 and optical member 104. Device 110 according to this exemplary embodiment is allowed to position first light receiving element 121 at a focus of the parabolic reflection surface of third reflection mirror 141BA by engagement between support body 103 and optical member 104. Device 110 according to this exemplary embodiment is allowed to position second light receiving element 122 at a focus of the parabolic reflection surface of third reflection mirror 141BB by engagement between support body 103 and optical member 104.

In device 110, optical member 104 is overlaid on board 106 with support body 103 interposed therebetween by insertion of projections 143 of optical member 104 into insertion holes 162A of board 106. According to device 110, optical member 104 is fixed to board 106 via support body 103 in a state of insertion of projections 143 of optical member 104 into insertion holes 162A of board 106. Device 110 is allowed to position support body 103 and reflection body 108 by insertion of engaging projections 135 of support body 103 into through holes 185A of reflection body 108. According to device 110, alignment between light emitting element 101 and first opening 181A is facilitated by use of engaging projections 135 and through holes 185A. According to device 110, alignment between light receiving elements 102 and second openings 182A is facilitated by use of engaging projections 135 and through holes 185A. Device 110 allows transmission of infrared light emitted from light emitting element 101 via first opening 181A by mounting reflection body 108 on support body 103. According to device 110 in this exemplary embodiment allows light receiving elements 102 to receive infrared light passing through second opening 182A by mounting reflection body 108 on support body 103.

Device 110 is capable of introducing the outside air into space 140A surrounded by optical member 104 and reflection body 108 via air hole 142. According to device 110, an amount of infrared light transmitted through first optical filter 151 and received by first light receiving element 121 decreases with respect to that of infrared light emitted from light emitting element 101 in accordance with a concentration of the detection target gas. When the concentration of the detection target gas is low, an amount of infrared light received by first light receiving element 121 becomes close to the amount of infrared light emitted from light emitting element 101 according to device 110. When the concentration of the detection target gas is high, the amount of infrared light received by first light receiving element 121 decreases. According to device 110, an amount of infrared light transmitted through second optical filter 152 and received by second light receiving element 122 does not vary in accordance with the concentration of the detection target gas.

In device 110, signal processing circuit unit 107 processes signals indicating an amount of received infrared light and output from light receiving elements 102. Device 110 is capable of detecting a concentration of the detection target gas contained in space 140A surrounded by optical member 104 and reflection body 108.

According to device 110 in this exemplary embodiment, signal processing circuit unit 107 calculates the concentration of the detection target gas based on a difference between output signal levels output from the pair of light receiving elements 102. Signal processing circuit unit 107 obtains the difference between the output signal levels output from first light receiving element 121 and second light receiving element 122, and calculates the concentration of the detection target gas based on this difference.

According to device 110, signal processing circuit unit 107 calculates the concentration of the detection target gas based on the difference between the signal levels output from first light receiving element 121 and second light receiving element 122. According to device 110, it is possible to cancel variations of respective signal levels output from light receiving elements 102 based on the difference between the output signal levels from first light receiving element 121 and second light receiving element 122 so as to prevent detection accuracy from lowering at the time of detection of a concentration of a gas.

When signal processing circuit unit 107 of device 110 calculates a concentration of a gas based on only the signal level output from one of light receiving elements 102, detection accuracy at the time of detection of the concentration of the gas may lower due to a variation of the output signal level from light receiving element 102 caused by some disturbance factor. However, when signal processing circuit unit 107 of device 110 according to this exemplary embodiment calculates a concentration of the detection target gas based on a difference between signal levels output from the pair of light receiving elements 102, lowering of detection accuracy at the time of detection of the concentration of the gas is suppressed by canceling variations of the output signal levels from respective light receiving elements 102.

Figure 24:
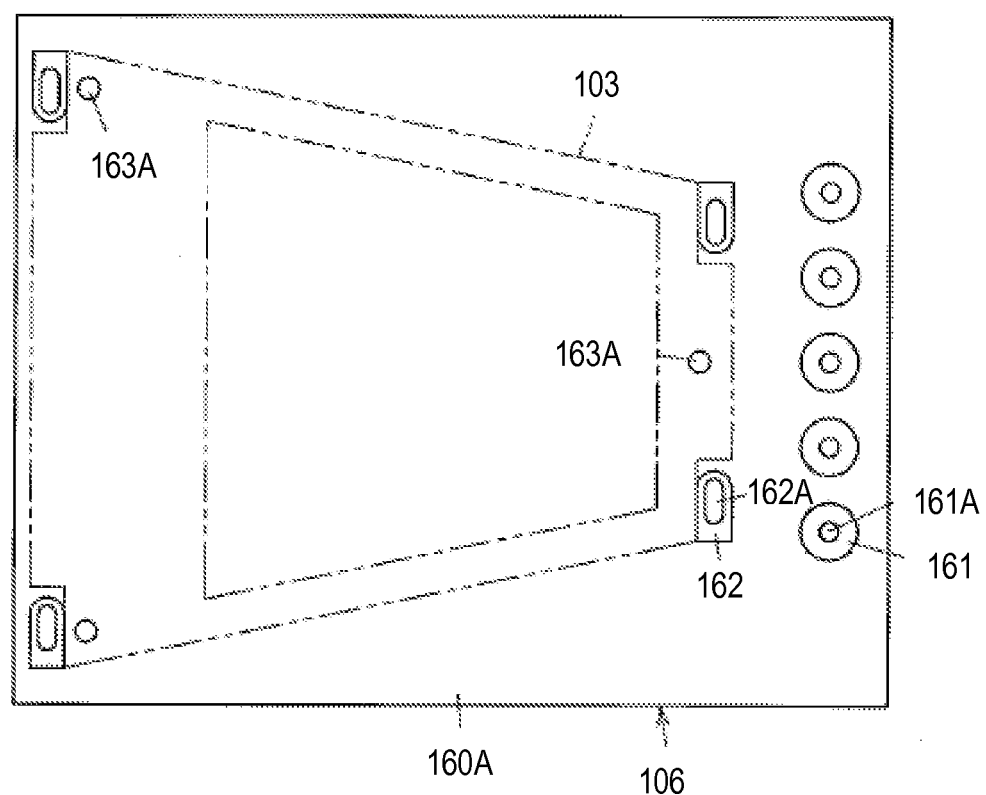
FIG. 24 is a plan view illustrating a further other essential part of the device according to the fourth exemplary embodiment.
Figure 25:
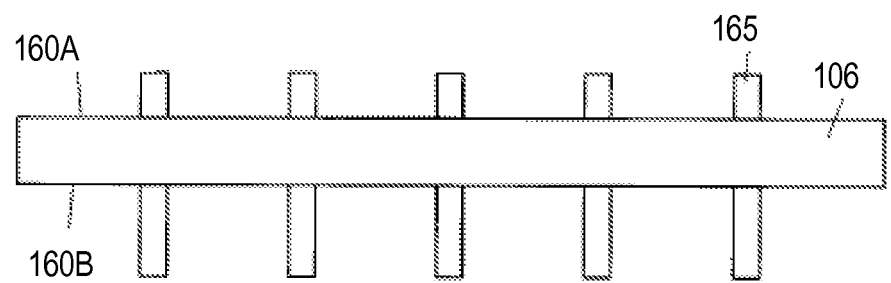
FIG. 25 is an explanatory side view illustrating the further other essential part of the device according to the fourth exemplary embodiment.
Figure 26:
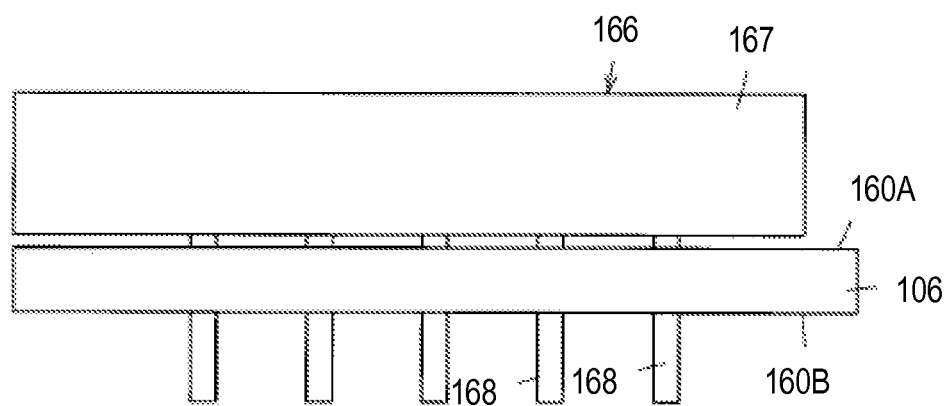
FIG. 26 is an explanatory side view illustrating an essential part of another device according to the fourth exemplary embodiment.
Figure 27:
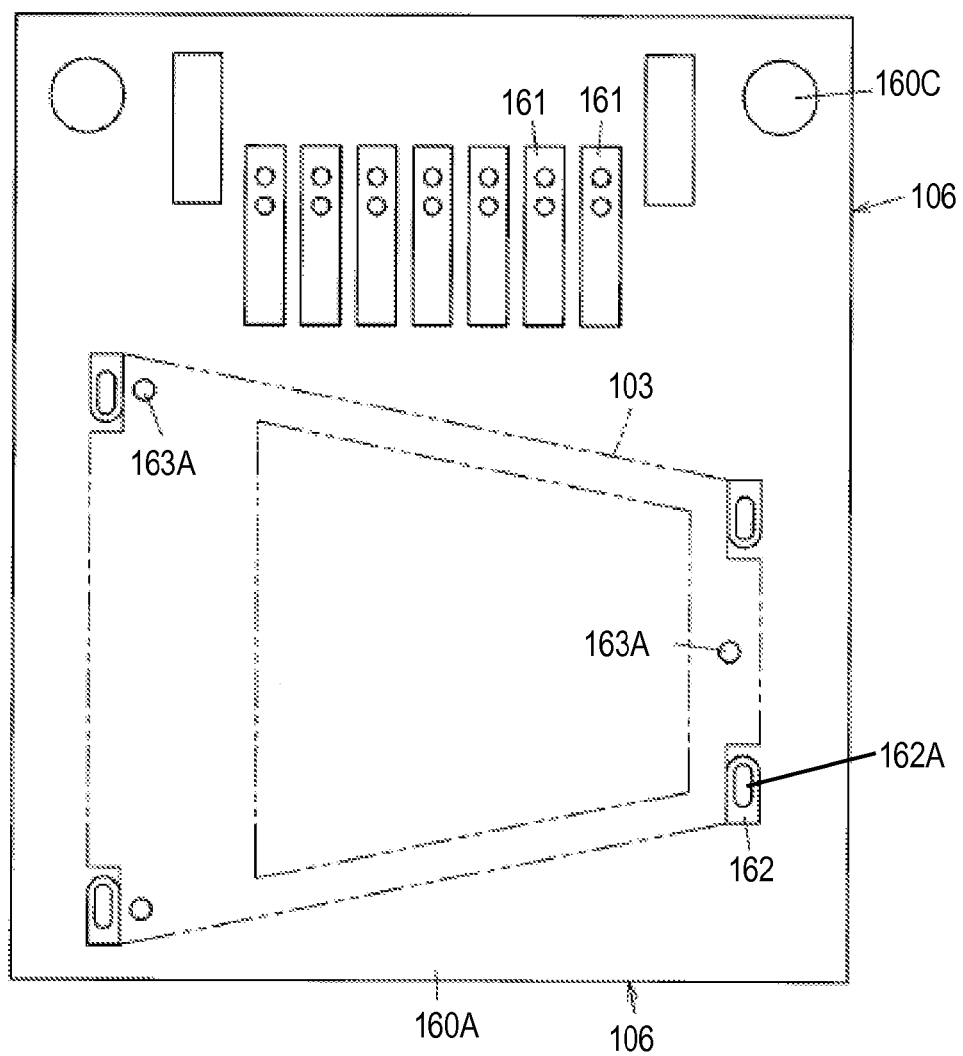
FIG. 27 is a plan view illustrating an essential part of a still other device according to the fourth exemplary embodiment.
Figure 28:
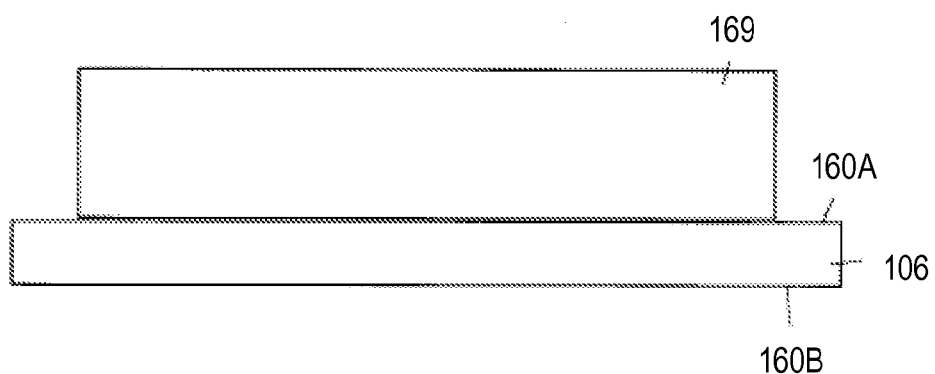
FIG. 28 is an explanatory side view illustrating the essential part of the still other device according to the fourth exemplary embodiment.

In device 110 in this exemplary embodiment, wiring of board 106 is electrically connected to conductor wiring 161 configured to outputting signals received from light receiving elements 102 to the outside. Conductor wiring 161 is electrically connected with the wiring formed on front surface 160A of board 106. Board 106 is provided with through holes 161A each formed at a center of conductor wiring 161 and penetrating board 106 (see FIG. 24). Metal terminals 165 (see FIG. 25) for outputting signals received from light receiving elements 102 can be inserted into through holes 161A. On board 106, metal terminals 165 inserted into through holes 161A are electrically connected with conductor wiring 161 via not-shown soldering, for example.

In device 110 in this exemplar embodiment, light emitting element 101, second light receiving element 122, and first light receiving element 121 are disposed in this order on support body 103 in the plan view. In other words, according to device 110, first light receiving element 121 and second light receiving element 122 are disposed adjacent to each other. Accordingly, device 110 in this exemplary embodiment reduces a detection time difference produced in detecting a gas by use of first light receiving element 121 and second light receiving element 122 in accordance with an entrance speed of the detection target gas into space 140A, and therefore device 110 is capable of detecting a gas more accurately than gas detector 1310 disclosed in the PTL.

A method for manufacturing device 110 according to this exemplary embodiment is hereinafter described with reference to FIGS. 19A through 28.

According to the method for manufacturing device 110, electronic part 171 is mounted on board 106 at the beginning. According to the method for manufacturing device 110, electronic part 171 constituting signal processing circuit unit 107 is soldered to the wiring of board 106 by reflow soldering, for example. Frame-shaped support body 103 is positioned on board 106 so as to surround an area where electronic part 171 is mounted (see FIG. 21). Light emitting element 101 and light receiving elements 102 may be mounted on the one surface 130A side of support body 103 in advance. According to the method for manufacturing device 110, support body 103 and board 106 are aligned by insertion of projections (not shown) projecting from support body 103 toward the board 106 side into holes 163A (see FIG. 24) of board 106.

When an automatic assembling device (not shown) is used in the method for manufacturing device 110, mounting positions of light emission element 101 and light receiving elements 102 are determined by performing an imaging process (such as edge detection) for an image of support body 103 imaged by an imaging device of the automatic assembling device. According to the method for manufacturing device 110, the mounting position of light emitting element 101 may be determined with reference to an edge of a shape of first recess 133. The mounting positions of light receiving elements 102 may be determined with reference to edges of shapes of second recesses 134. According to the method for manufacturing device 110, light emitting element 101 is mounted on an inner bottom surface of first recess 133 of support body 103 via a die bond material such as epoxy resin. Similarly, according to the method for manufacturing device 110, light receiving elements 102 are mounted on inner bottom surfaces of second recesses 134 of support body 103 via die bond materials such as epoxy resin. According to the method for manufacturing device 110, the wiring side formed on front surface 160A of board 106 is electrically connected to light emitting element 101 by wire bonding using metal wire. According to the method for manufacturing device 110, the wiring side formed on front surface 160A of board 106 is electrically connected to light receiving elements 102 by wire bonding using metal wire. According to the method for manufacturing device 110, optical filters 105 are disposed on the pair of second steps 132B formed in the inner walls of each of second recesses 134 of support body 103 in such a manner that optical filters 105 cover corresponding light receiving elements 102. Similarly, according to the method for manufacturing device 110, cover member 109 is disposed on the pair of first steps 132A formed in the inner walls of first recess 133 of support body 103 in such a manner that cover member 109 covers light emitting element 101.

Figure 22:
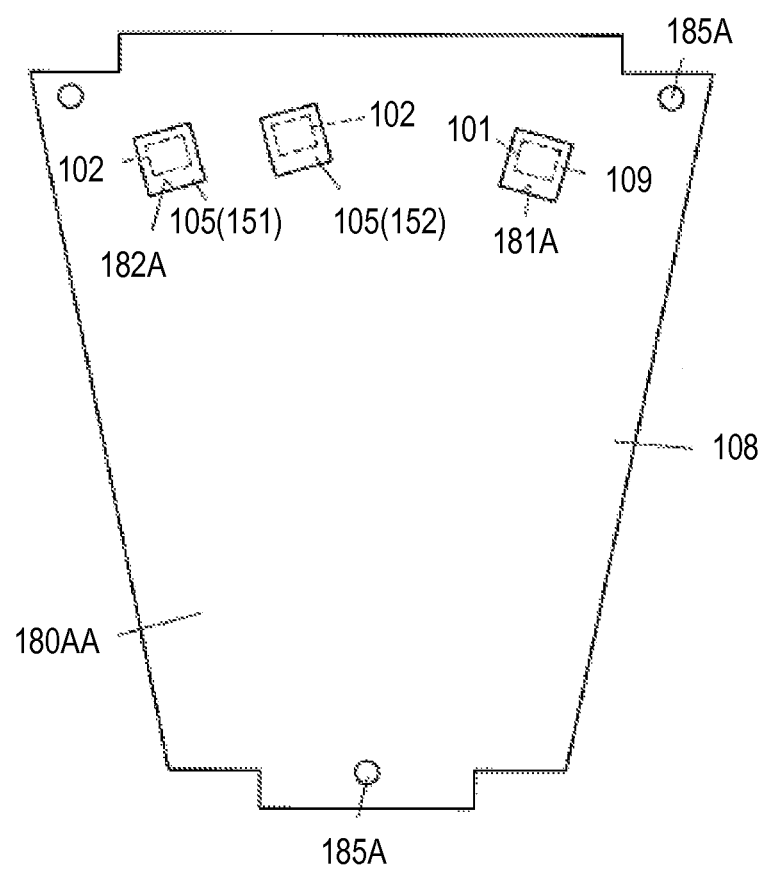
FIG. 22 is a plan view illustrating a still other essential part of the device according to the fourth exemplary embodiment.

Subsequently, according to the method for manufacturing device 110, reflection body 108 is positioned on support body 103 on which optical filters 105 and cover member 109 are disposed (see FIG. 22). According to the method for manufacturing device 110, support body 103 and reflection body 108 are aligned by insertion of engagement projections 135 projecting from support body 103 toward the optical member 104 side into through holes 185A of reflection body 108. According to the method for manufacturing device 110, first opening 181A and light emitting element 101 are aligned by alignment between support body 103 and reflection body 108. In addition, according to the method for manufacturing device 110, second openings 182A and light receiving elements 102 are aligned by alignment between support body 103 and reflection body 108.

According to the method for manufacturing device 110, optical member 104 is overlaid on board 106 with support body 103 interposed therebetween by insertion of projections 143 projecting from optical member 104 toward the board 106 side into insertion holes 162A of board 106 after positioning of reflection body 108 on support body 103 (see FIGS. 20 and 21). According to the method for manufacturing device 110, projections 143 of optical member 104 are joined to lands 162 formed around insertion holes 162A by soldering. In device 110, projections 143 of optical member 104 are joined to lands 162 around insertion holes 162A by soldering (not shown).

In device 110, optical member 104 formed as a resin molded component whose outside surface 140B is coated with metal material is electrically connected to lands 162 around insertion holes 162A of board 106. On device 110, lands 162 around insertion holes 162A of board 106 are grounded. Accordingly, optical member 104 is a resin molded component whose outside surface 140B is coated with the metal portion made of metal material, and the metal material is electrically connected to the ground of board 106.

According to device 110, a potential of optical member 104 coated with the metal portion of metal material may be set to a reference potential. In device 110, noise is prevented from occurring in electronic part 171 or the like provided on board 106 covered by optical member 104. The noise may occur resulting from entrance of electromagnetic waves from the outside of device 110. Similarly, according to device 110, a potential of reflection body 108 contacting optical member 104 is allowed to be set to the reference potential in accordance with setting of the potential of optical member 104 coated with the metal portion of metal material to the reference potential. By setting the potential of reflection body 108 to the reference potential, noise is further prevented from occurring in electronic part 171 or the like provided on board 106 covered by reflection body 108. The noise may occur resulting from entrance of electromagnetic waves from the outside of device 110.

According to device 110 in this exemplary embodiment, metal terminals 165 are inserted into through holes 161A of board 106. According to device 110, conductor wiring 161 formed around through holes 161A of board 106 is electrically connectable with metal terminals 165 via soldering (not shown), for example. Device 110 is electrically connectable with an external apparatus via metal terminals 165. According to device 110, patterns of conductor wiring 161 formed on board 106 can be changed relatively easily in comparison with a device in which terminals for outputting signals received from light receiving elements 102 to the outside are formed in a resin component by insert molding.

In device 110 according to this exemplary embodiment, optical member 104 is optically coupled with support body 103 on which light emitting element 101 and light receiving elements 102 are mounted as elements requiring relatively high alignment accuracy. In addition, in device 110, optical member 104 is fixed to board 106 which does not require relatively high alignment accuracy with support body 103 and optical member 104 in comparison with the optical coupling. According to device 110, conductor wiring 161 for outputting signals from the light receiving elements 102 side to the outside is provided on board 106 which does not require relatively high alignment accuracy, and therefore a degree of freedom for electric connection to the outside further increases. In other words, in device 110 according to this exemplary embodiment, support body 103 which holds light emitting element 101 and light receiving elements 102 with a predetermined distance therebetween is functionally separated from board 106 which includes conductor wiring 161 for outputting signals to the outside.

Accordingly, device 110 of different mount configuration can be manufactured only by replacing board 106 containing conductor wiring 161 with board 106 having a different configuration. This structure standardizes components constituting device 110, and can increase a degree of freedom for electric connection between device 110 and an external apparatus provided outside device 110 for each type of apparatus on which device 110 of this exemplary embodiment is mounted.

According to device 110 in this exemplary embodiment, reflection body 108 includes first opening 181A through which infrared light emitted from light emitting element 101 passes. Reflection body 108 includes second openings 182A through which infrared light to be received by light receiving elements 102 passes. In device 110, translucent cover member 109 closes first opening 181A. In device 110, optical filters 105 close second openings 182A. Translucent cover member 109 and optical filters 105 prevent a gas from flowing toward the light receiving elements 102 side from space 140A surrounded by reflection body 108, cover member 109, optical filters 105, and optical member 104. Optical filters 105 are considered to have translucency. Accordingly, cover member 109 is considered as a first translucent cover member, while optical filters 105 are considered as second translucent cover members.

While a configuration of each of light receiving elements 102 of device 110 according to this exemplary embodiment is not shown in the figure, each of light receiving elements 102 may have a configuration of a pyroelectric infrared sensor which includes a membrane disposed on a cavity portion and formed of an insulation film, and contains a pyroelectric element which includes a pyroelectric material disposed on the insulation film and sandwiched between electrodes. This infrared sensor may be formed in an appropriate manner by using MEMS (Micro Electro Mechanical Systems) technology, for example.

According to an example of a device which does not include cover member 109 presented in comparison with device 110 according to this exemplary embodiment, a detection target gas may flow from the space 140A side toward the light receiving elements 102 side via first opening 181A. When the detection target gas flows from the space 140A side toward the light receiving elements 102 side in the device of the comparison example, the membrane of the infrared sensor may be deformed by pressure of the gas. When the membrane of the infrared sensor is deformed in the device of the comparison example, detection errors of the infrared sensor or damage to the infrared sensor may be caused.

According to device 110 in this exemplary embodiment, however, detection errors of the infrared sensor and damage to the infrared sensor caused by pressure of the detection target gas are suppressed even when each of light receiving elements 102 includes the infrared sensor containing a membrane.

Device 110 according to this exemplary embodiment is applicable to a gas sensor equipped on an air conditioner, a gas detection alarm, a vehicle exhaust gas measuring device, and alcohol detector, for example.

The respective components included in device 110 according to this exemplary embodiment are hereinafter described in more detail.

Light emitting element 101 is capable of emitting infrared light. Light emitting element 101 may be constituted by a semiconductor bare chip. Light emitting element 101 is not limited to a semiconductor bare chip, but may be constituted by a chip size package. Light emitting element 101 may be constituted by a light emitting diode chip, or a resistance element or a laser diode provided on a semiconductor substrate, for example. Light emitting element 101 is capable of emitting infrared light having a wavelength easily absorbable by a detection target gas. Light emitting element 101 can be electrically connected with wiring on board 106 by an appropriate method such as wire bonding. The entire size of device 110 can be smaller when light emitting element 101 is constituted by a semiconductor bare chip, in comparison with a device which uses a package type light emitting diode.

Light receiving elements 102 are capable of receiving infrared light and converting the infrared light into electric signals. Light receiving elements 102 may be constituted by semiconductor bare chips. Light receiving elements 102 are not limited to semiconductor bare chips, but may be constituted by chip size packages. Light receiving elements 102 may be constituted by pyroelectric elements or photodiode chips, for example. Light receiving elements 102 can be electrically connected with wiring provided on board 106 by an appropriate method such as wire bonding. The entire size of device 110 can be smaller when light receiving elements 102 are constituted by semiconductor bare chips, in comparison with a device which uses package type photodiodes.

Support body 103 is capable of supporting light emitting element 101 and light receiving elements 102 at one end side on the one surface 130A side of support body 103. Support body 103 may have a frame-shaped external appearance. Frame-shaped support body 103 is capable of receiving electronic part 171 mounted on board 106 and accommodating electronic part 171 within opening 131A thereof. Support body 103 may be constituted by a resin molded component formed of a synthetic resin molded body. Support body 103 may be made of polyphthalamide resin, for example. On support body 103, cover member 109 may be disposed on first steps 132A so as to cover light emitting element 101. On support body 103, optical filters 105 may be positioned on second steps 132B so as to cover light receiving elements 102. Reflection body 108 may be positioned so as to cover opening 131A of frame-shaped support body 103. In reflection body 108, a fifth optical path changing portion can be provided so as to reflect and guide infrared light from the first reflection mirror 141AA side to the third reflection mirrors 141BA and 141BB side via reflection mirror 141AB. Reflection body 108 may close a part of opening 131A of frame-shaped support body 103. Supporting reflection body 108 covering opening 131A of frame-shaped support body 103 and reflecting infrared light toward space 140A by support body 103 can increase light utilization efficiency.

Optical member 104 is so configured that infrared light from light emitting element 101 can be guided toward the light receiving elements 102 side. Optical member 104 is capable of covering the one surface 130A side of support body 103 via space 140A into which the detection target gas is introducible. Optical member 104 may be constituted by a resin molded component formed of a synthetic resin molded body. Optical member 104 may be made of polyphthalamide resin, for example. Optical member 104 is not limited to a resin molded component, but may be made of metal material. Optical member 104 constituted by a resin molded component has a more accurate external appearance than a component made of metal material. It is preferable that outside surface 140B of optical member 104 is coated with metal material when optical member 104 is formed as a resin molded component. Optical member 104 may have a parallelepiped shape having an external size equivalent to that of support body 103 in the plan view. Optical member 104 is allowed to be fixed to board 106 in a manner that a recess of optical member 104 faces board 106 via support body 103. Optical member 104 may be provided with air hole 142 penetrating optical member 104 in the direction of the thickness of optical member 104. According to optical member 104, the detection target gas can be introduced into space 140A through air hole 142. According to optical member 104, the detection target gas can be discharged out of space 140A through air hole 142. It is preferable that air hole 142 of optical member 104 is covered by dust filter 111 to prevent foreign material other than the outside air, such as dust, from entering into air hole 142. Air hole 142 may have a rectangular shape in the plan view, for example. The shape of air hole 142 is not limited to a rectangular shape, but may have other shapes such as a circular shape in the plan view. The number of air hole 42 is not limited to one, but may be two or more.

Optical member 104 may include first reflection mirror 141AA, reflection mirror 141AB constituting the second reflection mirror, third reflection mirrors 141BA and 141BB, and fourth reflection mirror 141C, for example. Optical member 104 may include metal material such as gold and aluminum formed on the inner surface of the recess of optical member 104 by deposition or plating.

The reflection surface of first reflection mirror 141AA is not limited to a parabolic surface. First reflection mirror 141AA may have a reflection surface having a flat shape, a spherical shape, or a polygonal shape. The reflection surface of reflection mirror 141AB is not limited to a smooth flat surface. Reflection mirror 141AB may have a reflection surface having a parabolic shape, a spherical shape, or a polygonal shape. Each of the reflection surfaces of third reflection mirrors 141BA and 141BB is not limited to a parabolic surface. Each of third reflection mirrors 141BA and 141BB may have a reflection surface having a flat shape, a spherical shape, or a polygonal shape. When the reflection surface of each of third reflection mirrors 141BA and 141BB of device 110 is made to be a concave surface, light reflected on the reflection surfaces of third reflection mirrors 141BA and 141BB is allowed to converge. Accordingly, infrared light can be efficiently received by light receiving elements 102.

Each of optical filters 105 is capable of transmitting infrared light having a predetermined wavelength band. Each of optical filters 105 constitutes a band pass filter which has a transmission band containing a wavelength band of a wavelength of infrared light emitted from light emitting element 101. Each of optical filters 105 may be formed of an interference filter having a multilayered structure of dielectric films, for example. Examples of a base material of each of optical filters 105 include Ge, Si and other semiconductor materials, and methacrylic resin. Optical filters 105 may be disposed on second steps 132B of support body 103. Optical filters 105 may be fixed to second steps 132B of support body 103 via bonding material (not shown). Optical filters 105 may be fixed to reflection body 108 via bonding material. Optical filters 105 may be fixed to light receiving elements 102 via bonding material. The bonding material employed herein may be made of glass having a low melting point, alloy having a low melting point, or resin material, for example.

Board 106 can be attached to optical member 104 via support body 103. Board 106 may have a rectangular flat-plate external shape, for example. Board 106 is not limited to have a rectangular flat-plate shape, but may have various shapes such as a circular flat-plate shape and a polygonal flat-plate shape. Board 106 may be constituted by a glass epoxy resin substrate, or a ceramic multi-layered substrate, for example. Electronic part 171 constituting signal processing circuit unit 107 may be mounted on board 106, for example. Board 106 includes wiring. Board 106 includes conductor wiring 161 capable of electrically connecting with the wiring. Conductor wiring 161 is capable of electrically connecting light receiving elements 102 and electronic part 171 constituting signal processing circuit unit 107 together via wiring so that signals from light receiving elements 102 can be output.

Board 106 is provided with through holes 161A penetrating board 106. According to board 106, conductor wiring 161 around through holes 161A and can be electrically connected to terminals 165 inserted into through holes 161A via soldering (not shown) or the like. Device 110 is allowed to be mounted on a wiring board (not shown) of an external apparatus by use of metal terminals 165. Similarly, device 110 is allowed to include receptacle 166 which contains contact pins 168 within connector body 167 formed by insulation material (see FIG. 26), instead of use of metal terminals 165. Device 110 electrically connects contact pins 168 of receptacle 166 to conductor wiring 161. According to Device 110, conductor wiring 161 can be electrically connected, via receptacle 166, to a plug electrically connected with a wiring board on the apparatus side. Alternatively, according to device 110, surface mounting type receptacle 169 may be surface-mounted on conductor wiring 161 of board 106 illustrated in FIG. 27 via soldering or the like (see FIG. 28), instead of use of metal terminals 165. Device 110 can be electrically connected with the wiring board on the apparatus side by using metal terminals 165, receptacle 166, or receptacle 169. Device 110 is preferably provided with screw holes 160C for receiving screws or the like and fixing device 110 to the wiring board (not shown) of the external apparatus.

Signal processing circuit unit 107 is configured to control light emitting element 101 to allow emission of infrared light from light emitting element 101. Signal processing circuit unit 107 is configured to process signals output from light receiving elements 102 upon receiving infrared light. Signal processing circuit unit 107 may perform signal processing such as amplification, waveform shaping, signal sampling, and signal analog/digital conversion of the signals output from light receiving elements 102. Signal processing circuit unit 107 may further perform signal processing such as signal calculation, signal correction, and determination that the detection target gas has an abnormal concentration, for example. Signal processing circuit unit 107 may be formed of electronic part 171 such as an integrated circuit.

Reflection body 108 is capable of reflecting infrared light toward space 140A. Reflection body 108 may be a flat-shaped component formed of metal plate material. Examples of material of reflection body 108 include metal material such as aluminum. Reflection body 108 is made of metal, and electrically connectable with the metal portion made of metal material of optical member 104. Reflection body 108 may include the fifth optical path changing portion capable of reflecting infrared light, and having a smooth surface on the side facing optical member 104. Reflection body 108 is not required to be made of metal material, but may be a resin molded component. Reflection body 108 may be a flat-plate-shaped member formed as a resin molded component on which gold, aluminum or other metal material is formed by deposition or plating.

Fifth Exemplary Embodiment

Device 110 according to this exemplary embodiment is different from device 110 in the fourth exemplary embodiment illustrated in FIGS. 19A and 19B chiefly in that the shape of optical member 104 and the positions of optical filters 105 are different. Constituent elements similar to corresponding constituent elements in the fourth exemplary embodiment are given similar reference numbers, and the same explanation is not repeated when omission of the explanation is appropriate.

Figure 29:
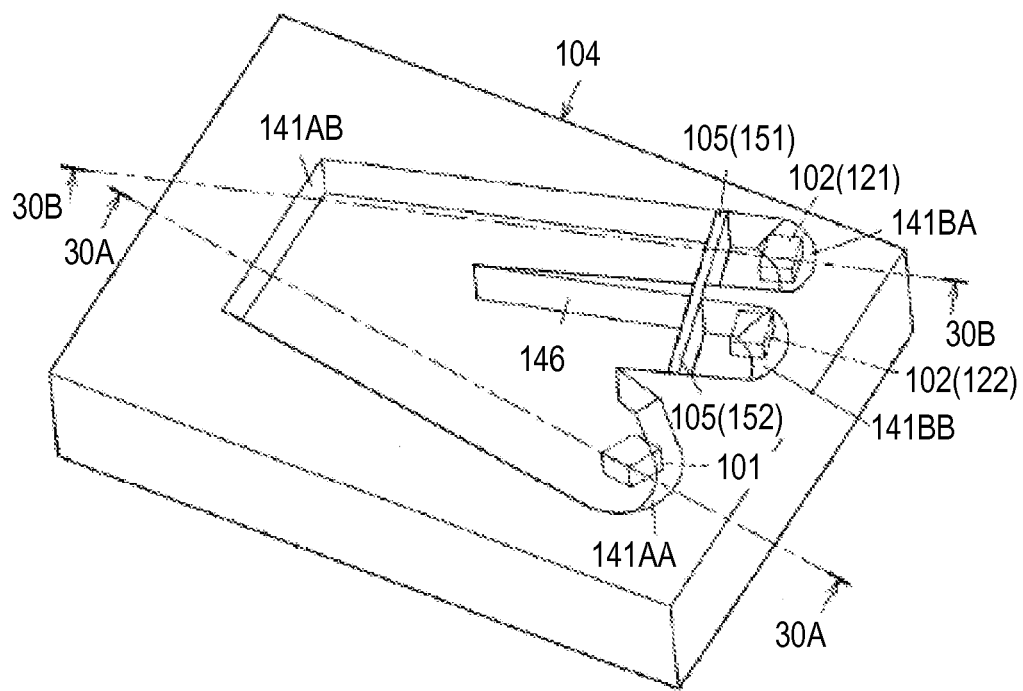
FIG. 29 is an explanatory perspective view illustrating an essential part of a device according to a fifth exemplary embodiment.
Figure 30A:
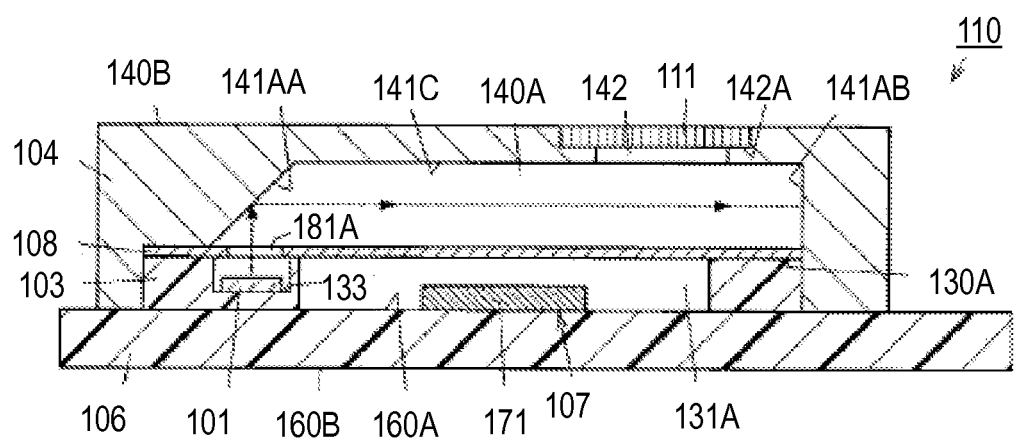
FIG. 30A is a cross-sectional view schematically illustrating the device according to the fifth exemplary embodiment.
Figure 30B:
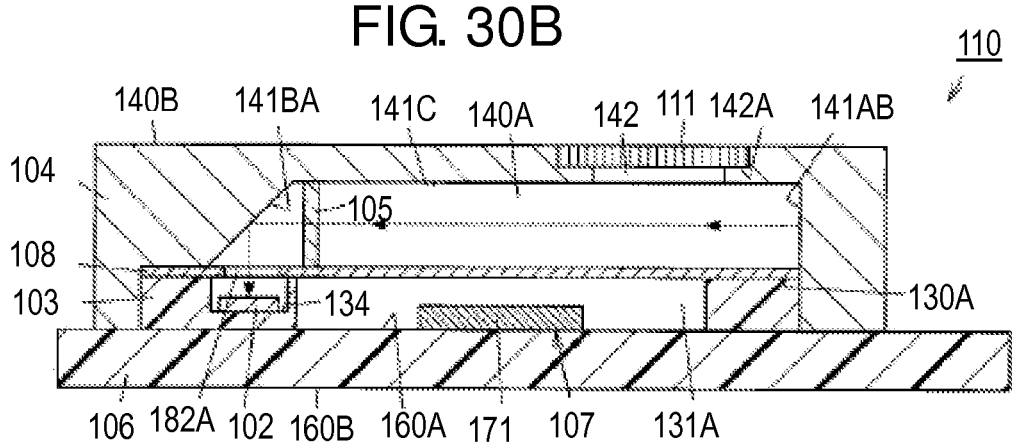
FIG. 30B is a cross-sectional view schematically illustrating the device taken along another cutting plane according to the fifth exemplary embodiment.

In device 110 in this exemplary embodiment, first optical filter 151 is disposed on optical member 104 between reflection mirror 141AB and third reflection mirror 141BA as illustrated in FIG. 29, for example. Similarly, in device 110 in this exemplary embodiment, second optical filter 152 is disposed on optical member 104 between reflection mirror 141AB and third reflection mirror 141BB. In other words, optical filters 105 are only required to be positioned on optical paths (see arrows in FIGS. 30A and 30B) for guiding infrared light from light emitting element 101 toward light receiving elements 102 as illustrated in FIGS. 30A and 30B. FIG. 30A is a cross-sectional view illustrating a cross section of device 110 taken along a line 30A-30A in FIG. 29. On the other hand, FIG. 30B is a cross-sectional view illustrating a cross section of device 110 taken along a line 30B-30B in FIG. 29.

Device 110 according to this exemplary embodiment includes separation wall 146 which separates optical paths of infrared lights to be received by first light receiving element 121 and second light receiving element 122 on optical member 104. Separation wall 146 reduces mutual effect on infrared lights received by first light receiving element 121 and second light receiving element 122 in optical member 104 as a result of scattering of the infrared lights or others. According to device 110 in this exemplary embodiment, separation wall 146 of optical member 104 holds first optical filter 151 and second optical filter 152.

Sixth Exemplary Embodiment

Device 110 according to this exemplary embodiment is different from device 110 in the fourth exemplary embodiment in that three or more sets of optical filter 105 and light receiving element 102 are provided for one light emitting element 101 instead of two sets of optical filter 105 and light receiving element 102 for one light emitting element 101 as in the fourth exemplary embodiment illustrated in FIGS. 19A and 19B. Constituent elements similar to corresponding constituent elements in the fourth exemplary embodiment have been given similar reference numbers, and the same explanation is not repeated when omission of the explanation is appropriate.

Figure 31:
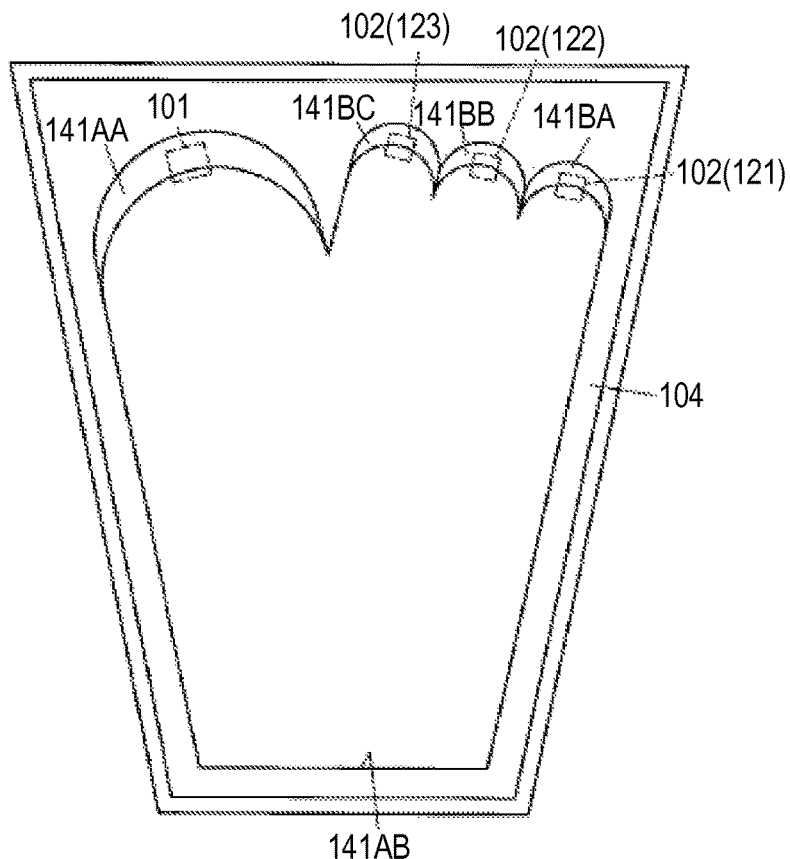
FIG. 31 is a bottom view illustrating an essential part of a device according to a sixth exemplary embodiment.
Figure 32:
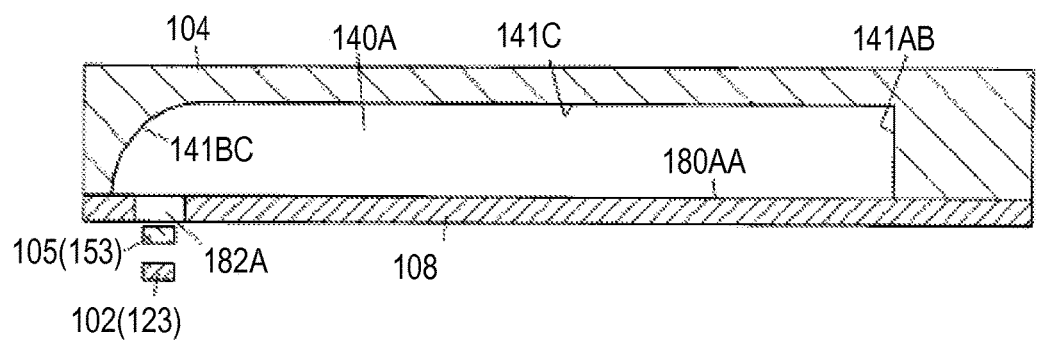
FIG. 32 is an explanatory cross-sectional view illustrating the essential part of the device according to the sixth exemplary embodiment.

According to device 110 in this exemplary embodiment, as in the fourth exemplary embodiment, optical filters 105 include first optical filter 151 which has a transmission band containing infrared light in a wavelength band absorbable by a detection target gas, and second optical filter 152 which has a transmission band different from that of first optical filter 151. Light receiving elements 102 include first light receiving element 121 which photoelectrically converts infrared light transmitted through first optical filter 151, and second light receiving element 122 which photoelectrically converts infrared light transmitted through second optical filter 152. According to device 110 in this exemplary embodiment, optical filters 105 further include third optical filter 153 which has a transmission band different from those of first optical filter 151 and second optical filter 152 as illustrated in FIGS. 31 and 32. Light receiving elements 102 include third light receiving element 123 which photoelectrically converts infrared light transmitted through third optical filter 153. Optical member 104 includes third reflection mirrors 141BA and 141BB. According to the device in this exemplary embodiment, optical member 104 further includes third reflection mirror 141BC as illustrated in FIG. 31.

This structure allows device 110 according to this exemplary embodiment to detect various types of gases. While device 110 according to the fourth exemplary embodiment is an example of a gas sensor for detecting a concentration of one type of gas contained in the outside air, device 110 including a plurality of sets of light receiving element 102 and optical filter 105 becomes a gas sensor capable of detecting concentrations of gases of different types for each set of light receiving element 102 and optical filter 105. Device 110 according to this exemplary embodiment includes three or more sets of light receiving element 102 and optical filter 105, and is thus capable of detecting concentrations of gases of different types based on outputs from respective light receiving elements 102.

Device 110 according to this exemplary embodiment includes first light receiving element 121 as one of light receiving elements 102 for gas detection. Device 110 further includes second light receiving element 122 as the other one of light receiving elements 102 for gas detection. According to device 110 in this exemplary embodiment, each of optical filters 105 constitutes a band pass filter which has a transmission band containing a predetermined wavelength. Device 110 in this exemplary embodiment which includes a plurality of sets of receiving element 102 for gas detection and optical filter 105 is capable of detecting a plurality of gases. Device 110 according to this exemplary embodiment is capable of independently detecting concentrations of two different types of gases among a plurality of types of gases contained in the outside air. Device 110 according to this exemplary embodiment is capable of simultaneously detecting both of a first gas (such as carbon monoxide) and a second gas (such as nitrogen oxide) of two types of gases. Moreover, device 110 according to this exemplary embodiment includes third optical filter 153 which transmits a band not absorbed by either the first gas or the second gas. Third light receiving element 123 receives infrared light transmitted through third optical filter 153, photoelectrically converts the infrared light into a signal, and outputs the signal to signal processing circuit unit 107. Signal processing circuit unit 107 measures a change ratio from initial output from light emitting element 101 based on the signal output from third light receiving element 123. According to device 110, signal processing circuit unit 107 corrects output from first light receiving element 121 and output from second light receiving element 122 after measuring the change ratio from the initial output from light emitting element 101. Device 110 is capable of eliminating deterioration of light emitting element 101 with time or other effects, and improving measurement accuracy by correcting outputs from first light emitting element 121 and second light emitting element 122.

Seventh Exemplary Embodiment

Device 210 according to this exemplary embodiment is hereinafter described with reference to FIGS. 33 through 35.

Figure 33:
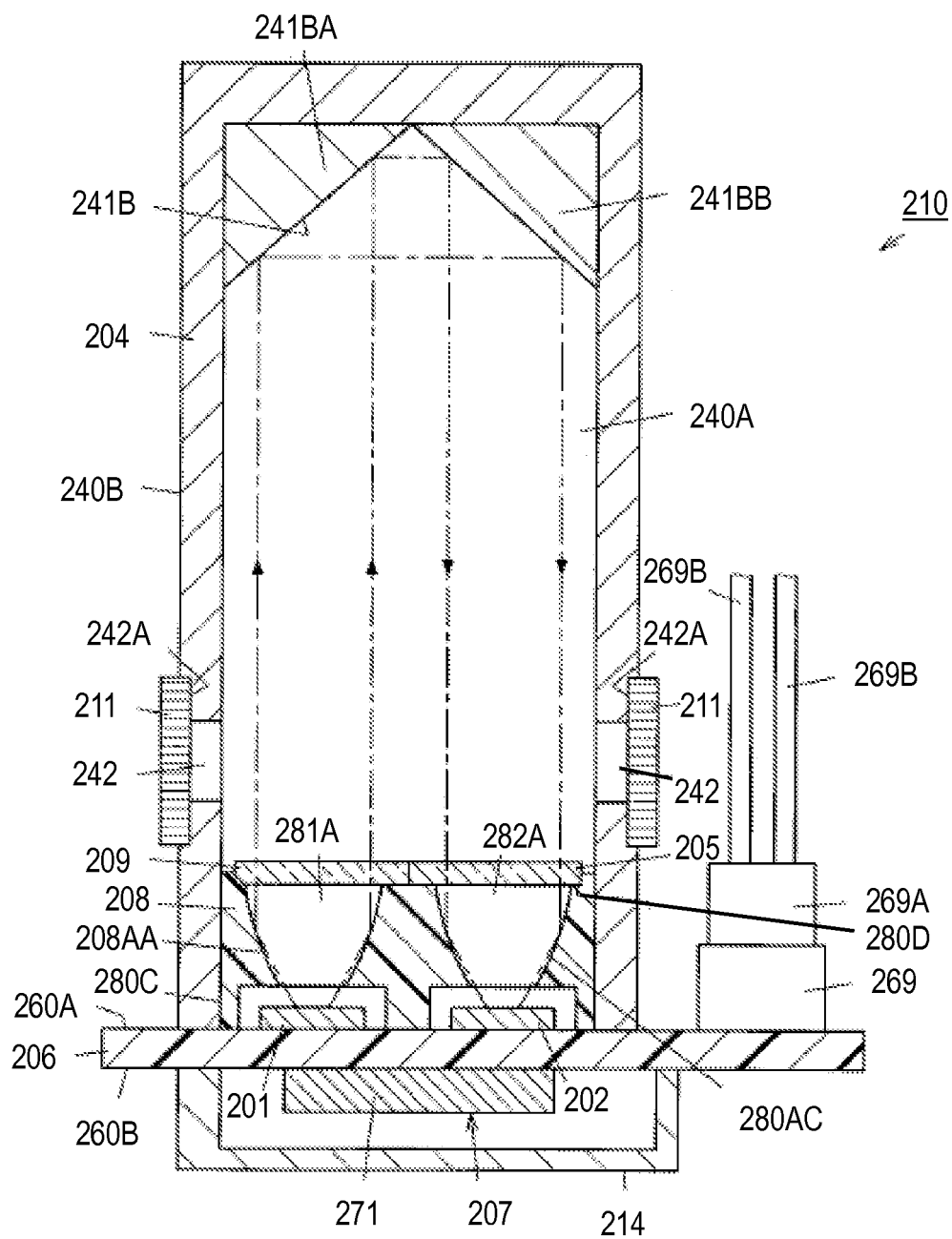
FIG. 33 is an explanatory cross-sectional view illustrating a device according to a seventh exemplary embodiment.
Figure 34:
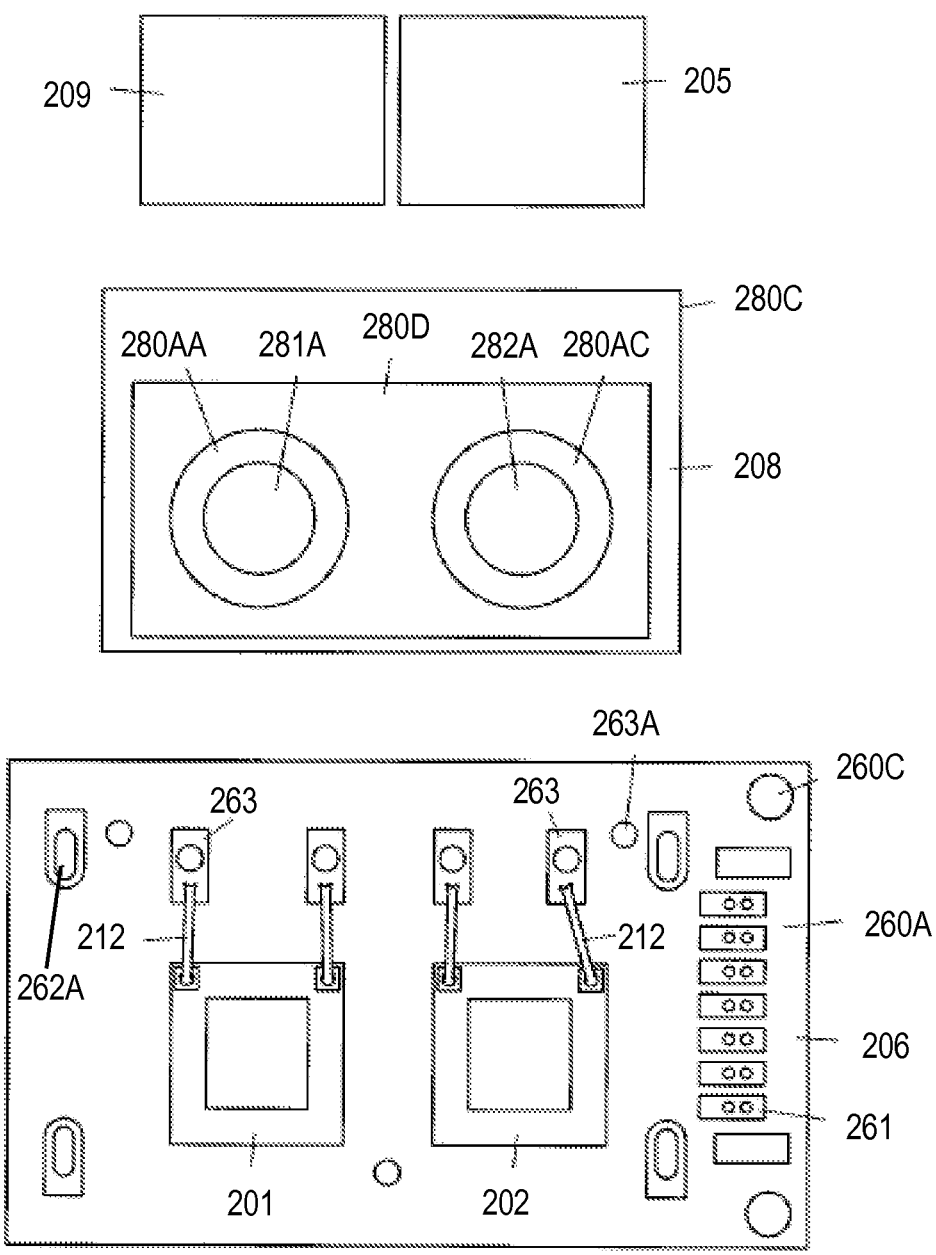
FIG. 34 is a plan view illustrating an essential part of the device according to the seventh exemplary embodiment.
Figure 35:
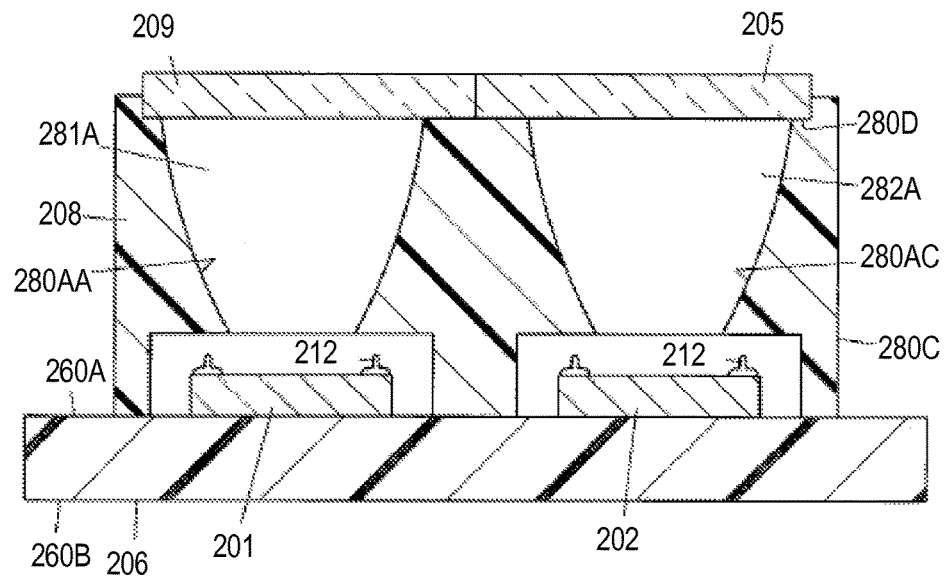
FIG. 35 is a cross-sectional view schematically illustrating another essential part of the device according to the seventh exemplary embodiment.

FIGS. 33 and 34 are a cross-sectional explanatory view illustrating device 210 according to a seventh exemplary embodiment, and a plan view illustrating an essential part of device 210, respectively. Device 210 according to this exemplary embodiment is a gas detecting device. Device 210 includes light emitting element 201, light receiving element 202, signal processing circuit unit 207, optical member 204, and board 206. Signal processing circuit unit 207 processes a signal output from light receiving element 202. Optical member 204 covers light emitting element 201 and light receiving element 202. Light emitting element 201, light receiving element 202, signal processing circuit unit 207, and optical member 204 are mounted on board 206. Board 206 includes conductor wiring 261 electrically connected with light receiving element 2.

This structure increases a degree of freedom for electric connection between device 210 according to this exemplary embodiment and the outside.

Device 210 according to this exemplary embodiment includes light emitting element 201 capable of emitting infrared light, and light receiving element 202 capable of photoelectrically converting infrared light. Device 210 includes optical member 204 capable of guiding the infrared light emitted from light emitting element 201 toward light receiving element 202. Device 210 includes optical filter 205 disposed on an optical path (see chain line arrows in FIG. 33) for guiding the infrared light emitted from light emitting element 201 toward the light receiving element 202 side.

Light emitting element 201 and light receiving element 202 are disposed on one surface 260A side of board 206. Board 206 includes conductor wiring 261 for outputting a signal from light receiving element 202 to the outside. Optical member 204 is provided on the one surface 260A side of board 206 via space 240A into which a detection target gas is introducible. Optical member 204 includes first reflection mirror 241B disposed on the side opposed to one surface 260A of board 206 and capable of reflecting the infrared light emitted from light emitting element 201 and guiding the infrared light in a direction perpendicular to one surface 260A toward light receiving element 202 disposed on the one surface 260A side of board 206. Board 206 has reflection body 208 capable of reflecting infrared light on the one surface 260A side. Reflection body 208 includes first opening 281A through which the infrared light emitted from light emitting element 201 passes. Reflection body 208 includes second reflection mirror 280AA on a circumference of first opening 281A. Second reflection mirror 280AA converges infrared light in a direction perpendicular to one surface 260A. Reflection body 208 includes second opening 282A through which the infrared light reflected on the opposed surface passes. Reflection body 208 includes third reflection mirror 280AC on a circumference of second opening 282A. Third reflection mirror 280AC converges infrared light on light receiving element 202. This structure increases gas detection accuracy of device 210 according to this exemplary embodiment.

According to device 210, an infrared light wavelength absorbable by a gas varies for each detection target gas. In addition, according to device 210, an infrared light absorptivity by a gas may vary for each detection target gas. Furthermore, according to device 210, desired detection accuracy may vary for each detection target gas in accordance with use purposes. According to device 210 in this exemplary embodiment, optical member 204 appropriate for each detection target gas is selectable. According to device 210 in this exemplary embodiment, an optical path length for guiding infrared light is allowed to change only by replacing optical member 204. Accordingly, in case of device 210 in this exemplary embodiment, an optical path length corresponding to absorbability of infrared light by a detection target gas, for example, is selectable only by replacement of optical member 204. According to device 210 in this exemplary embodiment, detection accuracy for detecting different detection target gases increases only by replacement of optical member 204 or optical filter 205. According to device 210 in this exemplary embodiment, components constituting device 210 are allowed to be standardized regardless of types of detection target gases. Device 210 which includes a plurality of standardized components constituting device 210 achieves reduction of manufacturing cost of device 210, regardless of types of detection target gases.

A more specific configuration of device 210 according to this exemplary embodiment is hereinafter described.

In device 210 in this exemplary embodiment, light emitting element 201 emitting infrared light and light receiving element 202 for photoelectrically converting infrared light are mounted on board 206. Board 206 has a rectangular flat plate shape (see FIG. 34). Board 206 is formed of a glass epoxy resin substrate. Board 206 includes wiring 263 which is conductor pattern on one surface 260A thereof. In device 210, electronic part 271 is mounted on other surface 260B of board 206 on the side opposite to one surface 260A. Electronic part 271 is electrically connected with wiring (not shown) on the other surface 260B side of board 206 via soldering (not shown). The wiring on the other surface 260B side of board 206 is electrically connected with wiring 263 on the one surface 260A side of board 206 by through hole wiring (not shown) or the like. While only one electronic part 271 is shown in the figure according to device 210 in this exemplary embodiment, a plurality of electronic parts 271 may be mounted on board 206. A plurality of electronic parts 271 may be electrically connected with each other via wiring provided on board 206. Electronic part 271 constitutes signal processing circuit unit 207. According to device 210, signal processing circuit unit 207 may be constituted by a plurality of electronic parts 271. Signal processing circuit unit 207 is configured to allow emission of infrared light from light emitting element 201 by controlling light emitting element 201. Signal processing circuit unit 207 is configured to process a signal output from light receiving element 202 upon receiving infrared light. Signal processing circuit unit 207 performs signal processing such as amplification, waveform shaping, signal sampling, and signal analog/digital conversion of the signal output from light receiving element 202. Signal processing circuit unit 207 further performs signal processing such as signal calculation, signal correction, and determination that the detection target gas has an abnormal concentration, for example. Accordingly, electronic part 271 for processing a signal output from light receiving element 202 is mounted on board 206. According to device 210 in this exemplary embodiment, electronic part 271 constituting signal processing circuit unit 207 is covered with protection cover 214. Protection cover 214 covering electronic part 271 constituting signal processing circuit unit 207 is fixed to the other surface 260B side of board 206.

In device 210, light emitting element 201 is mounted on one surface 260A of board 206 via a die bond material (not shown). According to device 210, wiring 263 formed on one surface 260A of board 206 and light emitting element 201 are electrically connected by wire bonding using metal wire 212 (see FIG. 34), for example. Light emitting element 201 is constituted by a light emitting diode capable of emitting infrared light. This light emitting diode is constituted by a semiconductor bare chip. Light emitting element 201 emits infrared light having a wavelength easily absorbed by the detection target gas. Examples of the detection target gas include carbon monoxide, carbon dioxide, methane, and nitrogen oxide. The structure of light emitting element 201 mounted on one surface 260A of board 206 is capable of reducing mutual thermal effect between light emitting element 201 and the signal processing circuit unit 207 side provided on other surface 260B of board 206.

In device 210, light receiving element 202 is mounted on one surface 260A of board 206 via a die bond material (not shown). According to device 210, wiring 263 and light receiving element 202 both formed on one surface 260A of board 206 are electrically connected to each other via wire bonding using metal wire 212. Light receiving element 202 includes an infrared sensor capable of receiving infrared light. The infrared sensor is constituted by a pyroelectric element. The infrared sensor is provided as a semiconductor bare chip. Light emitting element 201 and light receiving element 202 are disposed on the one surface 260A side of board 206 with a predetermined distance therebetween.

On the one surface 260A side of board 206, reflection body 208 is provided so as to cover light emitting element 201 and light receiving element 202. According to device 210 in this exemplary embodiment, reflection body 208 has a bottomed and square cylindrical shape. Reflection body 208 includes first opening 281A formed in an inner bottom surface of the bottomed and square cylindrical shape. Infrared light emitted from light emitting element 201 passes through first opening 281A. First opening 281A has a paraboloidal shape which flares with farness from one surface 260A in a direction perpendicular to one surface 260A of board 206. Reflection body 208 includes second reflection mirror 280AA on a circumference of first opening 281A. A focus of second reflection mirror 280AA is positioned on light emitting element 201. Second reflection mirror 280AA converges infrared light in a direction perpendicular to one surface 260A. Reflection body 208 further includes second opening 282A formed in the inner bottom surface of the bottomed and square cylindrical shape. Infrared light passes through second opening 282A. Second opening 282A has a paraboloidal shape which flares with farness from one surface 260A in a direction perpendicular to one surface 260A of board 206. Infrared light emitted from light emitting element 201 and reflected on the opposed surfaces of optical member 204 is allowed to pass along reflection body 208. Reflection body 208 includes third reflection mirror 280AC on a circumference of second opening 282A. A focus of third reflection mirror 280AC is positioned on light receiving element 202. Third reflection mirror 280AC converges infrared light on light receiving element 202. In reflection body 208, first opening 281A is closed by translucent cover member 209. Reflection body 208 includes accommodation recess 280D formed in an outer bottom surface of bottomed and square cylindrical reflection body 208. In reflection body 208, cover member 209 is accommodated within accommodation recess 280D so as to cover light emitting element 201.

In reflection body 208, second opening 282A is closed by optical filter 205. Optical filter 205 is capable of constituting a band pass filter which has a transmission band containing a predetermined wavelength band in infrared wavelengths emitted from light emitting element 201. In reflection body 208, optical filter 205 is accommodated in accommodation recess 280D of reflection body 208 so as to cover light receiving element 202. Reflection body 208 may be formed as a resin molded component.

Device 210 according to this exemplary embodiment includes optical member 204 which covers one surface 260A of board 206 on which reflection body 208 is disposed. Optical member 204 has a bottomed and square cylindrical external shape. Optical member 204 is made of metal material. Examples of metal material constituting optical member 204 include aluminum, stainless steel, and copper. Optical member 204 may be formed by pressing of a metal plate. Optical member 204 constitutes a cover for covering the one surface 260A side of board 206 on which light emitting element 201 and light receiving element 202 are mounted. Optical member 204 has a bottomed and square cylindrical shape whose internal size is slightly larger than an external size of reflection body 208 in a plan view. Optical member 204 is provided with a recess opened to the board 206 side. According to device 210, the recess of optical member 204 forms space 240A into which the detection target gas is introducible.

As illustrated in FIG. 33, optical member 204 is provided on board 206 such that an inner bottom surface of the bottomed and square cylindrical shape of optical member 204 faces one surface 260A of board 206. Optical member 204 includes first reflection mirror 241B disposed on the inner bottom surface side of the bottomed square cylindrical shape so as to reflect infrared light in a predetermined direction. First reflection mirror 241B reflects infrared light emitted from light emitting element 201 in a direction perpendicular to one surface 260A of board 206 and guides the infrared light toward light receiving element 202 on the one surface 260A side of board 206. Optical member 204 includes metal material constituting optical member 204, and first reflection mirror 241B as separate components. Optical member 204 may include metal material constituting optical member, and first reflection mirror 241B as components formed integrally with each other. According to device 210 in this exemplary embodiment, first reflection mirror 241B is formed of first reflection portion 241BA and second reflection portion 241BB. First reflection portion 241BA may be constituted by a triangular prism made of metal material, for example. Similarly, second reflection portion 241BB may be constituted by a triangular prism made of metal material, for example. First reflection portion 241BA and second reflection portion 241BB are so disposed as to face each other. First reflection portion 241BA is so disposed as to face light emitting element 201. Second reflection portion 241BB is so disposed as to face light receiving element 202. First reflection mirror 241B includes first reflection portion 241BA and second reflection portion 241BB formed separately from each other. First reflection mirror 241B may include first reflection portion 241BA and second reflection portion 241BB formed integrally with each other. Optical member 204 includes first reflection mirror 241B as a reflection mirror disposed on the opposed surface side facing one surface 260A of board 206 so as to reflect infrared light emitted from light emitting element 201 and guide the infrared light again toward one end side of board 206. First reflection mirror 241B constitutes an optical path changing portion of optical member 204. Optical member 204 is capable of reflecting infrared light to guide the light from the first reflection portion 241BA side toward the second reflection portion 241BB side on the bottom of the recess of optical member 204.

First reflection portion 241BA may include a smooth flat reflection surface. First reflection portion 241BA changes an optical path of the infrared light emitted from light emitting element 201 into a predetermined direction perpendicular to a direction of a thickness of board 206. Second reflection portion 241BB is so disposed as to face first reflection portion 241BA, and may include a smooth flat reflection surface. Second reflection portion 241BB changes the optical path of the infrared light after a change of the optical path by first reflection portion 241BA into a direction crossing a light receiving surface of light receiving element 202. According to device 210, optical member 204 changes the optical path of infrared light traveling from light emitting element 201 toward light receiving element 202 (see chain lines in FIG. 33) into a C shape as illustrated in FIG. 33.

According to device 210 in this exemplary embodiment, size reduction is achievable in comparison with a device in which optical member 204 does not include first reflection mirror 241B but includes an optical member forming an optical path for linear emission of infrared light from light emitting element 201 toward the light receiving element 202 side facing light emitting element 201. According to device 210 in this exemplary embodiment, optical member 204 includes first reflection mirror 241B, and therefore an area of the optical path of the infrared light decreases in correspondence with a portion of the optical path of the infrared light folded by first reflection mirror 241B in comparison with the foregoing device which includes the optical member having the optical path for linear emission.

Optical member 204 including first reflection mirror 241B can guide the infrared light emitted from light emitting element 201 toward the light receiving element 202 side. Optical member 204 is provided with air holes 242 which penetrate optical member 204 in the direction of the thickness of optical member 204. Air holes 242 may have a rectangular shape, for example. Optical member 204 is capable of introducing the detection target gas into space 240A through air holes 242. According to optical member 204, dust filters 211 are provided on accommodation recesses 242A of optical member 204 so as to cover air holes 242 of optical member 204, respectively. Each of dust filter 211 prevents dust or other foreign material from entering into air hole 242. Dust filter 211 is fixed to accommodation recess 242A via a not-shown adhesive.

In device 210 according to this exemplary embodiment, reflection body 208 is positioned on board 206. Device 210 allows positioning reflection body 208 with respect to board 206 by engagement between engaging projections (not shown) of reflection body 208 and holes 263A of board 206.

In Device 210, alignment between light emitting element 201 and first opening 281A is facilitated by engagement between the engaging projections (not shown) of reflection body 208 and holes 263A of board 206. In Device 210, alignment between light receiving element 202 and second opening 282A is facilitated by engagement between the engaging projections (not shown) of reflection body 208 and holes 263A.

According to device 210, infrared light emitted from light emitting element 201 is allowed to pass through first opening 281A in a state that reflection body 208 is mounted on board 206. According to device 210 in this exemplary embodiment, light receiving element 202 can receive the infrared light after passing through second opening 282A in the state that reflection body 208 is mounted on board 206.

According to device 210, reflection body 208 can be positioned with respect to optical member 204 by engagement between optical member 204 and reflection body 208 disposed on board 206. In device 210, alignment between light emitting element 201 and first reflection mirror 241B is facilitated by engagement between optical member 204 and reflection body 208. In device 210, alignment between first reflection mirror 241B and light receiving element 202 is facilitated by engagement between optical member 204 and reflection body 208.

Optical member 204 includes rectangular parallelepiped projections (not shown) projecting from optical member 204 toward the board 206 side. According to device 210, optical member 204 is positioned on board 206 while covering reflection body 208 by insertion of the projections of optical member 204 into insertion holes 262A of board 206. According to device 210, optical member 204 is fixed to board 206 in a state of insertion of the projections of optical member 204 into insertion holes 262A of board 206.

According to device 210, the outside air is introducible through air holes 242 into space 240A surrounded by optical member 204, optical filter 205, reflection body 208, and cover member 209. According to device 210, an amount of infrared light transmitted through optical filter 205 and received by light receiving element 202 decreases with respect to that of infrared light emitted from light emitting element 201 in accordance with a concentration of the detection target gas. When the concentration of the detection target gas is low, an amount of infrared light received by light receiving element 202 becomes close to that of infrared light emitted from light emitting element 201 according to device 210. When the concentration of the detection target gas is high, the amount of infrared light received by light receiving element 202 decreases.

According to device 210, signal processing circuit unit 207 processes a signal corresponding to an amount of received infrared light and output from light receiving element 202. Device 210 is capable of detecting a concentration of the detection target gas contained in space 240A of optical member 204. According to device 210 in this exemplary embodiment, signal processing circuit unit 207 calculates the concentration of the detection target gas based on a signal level of a signal output from light receiving element 202.

According to device 210 in this exemplary embodiment, wiring 263, and conductor wiring 261 for outputting a signal received from light receiving element 202 to the outside are provided on the one surface 260A side of board 206. Conductor wiring 261 is electrically connected with wiring 263. Surface mounting type receptacle 269 is surface-mounted on conductor wiring 261 of board 206 via soldering or the like. Device 210 is capable of being electrically connected to a wiring board (not shown) on the external apparatus side via output lines 269B extended from plug 269A connected with receptacle 269. Device 210 may be provided with screw holes 260C in board 206 for receiving screws or the like fixing device 210 to the wiring board of the apparatus.

A method for manufacturing device 210 according to this exemplary embodiment is now described.

According to the method for manufacturing device 210, at the beginning, electronic part 271 is mounted on other surface 260B of board 206. According to the method for manufacturing device 210, electronic part 271 constituting signal processing circuit unit 207 is soldered to wiring on the other surface 260B side of board 206 by reflow soldering, for example. Protection cover 214 covers an area of board 206 where electronic part 271 is mounted so as to surround this area.

According to the method for manufacturing device 210, light emitting element 201 is mounted on one surface 260A of board 206 by a die bond material such as epoxy resin. Similarly, according to the method for manufacturing device 210, light receiving element 202 is mounted on one surface 260A of board 206 by a die bond material such as epoxy resin. According to the method for manufacturing device 210, wiring 263 formed on one surface 260A of board 206 is electrically connected to light emitting element 201 by wire bonding using metal wire 212. According to the method for manufacturing device 210, wiring 263 formed on one surface 260A of board 206 is electrically connected to light receiving element 202 by wire bonding using metal wire 212.

According to the method for manufacturing device 210, reflection body 208 is aligned with respect to board 206 by insertion of engaging projections (not shown) projecting from reflection body 208 toward the board 206 side into holes 263A of board 206 (see FIG. 34). According to the method for manufacturing device 210, alignment between first opening 281A and light emitting element 201 is achievable by alignment between reflection body 208 and board 206. According to the method for manufacturing device 210, alignment between second opening 282A and light receiving element 202 is achievable by alignment between reflection body 208 and board 206. According to the method for manufacturing device 210, cover member 209 is positioned in accommodation recess 280D of reflection body 208 so as to cover light emitting element 201. Similarly, according to the method for manufacturing device 210, optical filter 205 is positioned in accommodation recess 280D of reflection body 208 so as to cover light receiving element 202.

Thereafter, according to the method for manufacturing device 210, optical member 204 is positioned so as to cover reflection body 208 where optical filter 205 and cover member 209 are disposed. According to the method for manufacturing device 210, optical member 204 is overlaid on board 206 by insertion of the projections projecting from optical member 204 toward the board 206 side into insertion holes 262A of board 206 after positioning of reflection body 208 on board 206 (see FIGS. 34 and 35). According to the method for manufacturing device 210, the projections of optical member 204 are fixedly attached to portions of board 206 around insertion holes 262A by adhesives or the like.

According to device 210 in this exemplary embodiment, reflection body 208 includes first opening 281A through which infrared light emitted from light emitting element 201 passes. Reflection body 208 includes second opening 282A through which infrared light to be received by light receiving element 202 passes. In device 210, translucent cover member 209 closes first opening 281A and optical filter 205 closes second opening 282A. According to device 210, optical filter 205 prevents a gas from flowing from the space 240A side of optical member 204 toward the light receiving element 202 side. Similarly, cover member 209 prevents a gas from flowing from the space 240A side of optical member 204 toward the light receiving element 202 side. Optical filter 205 is considered to have translucency. Accordingly, cover member 209 is considered as a first translucent cover member, while optical filter 205 is considered as a second translucent cover member.

While a configuration of light receiving element 202 is not shown according to device 210 in this exemplary embodiment, light receiving element 202 may have a configuration of a pyroelectric infrared sensor including a membrane formed of an insulation film on a cavity portion, and containing a pyroelectric element which includes a pyroelectric material sandwiched between electrodes on the insulation film, for example. This infrared sensor may be formed in an appropriate manner by using MEMS (Micro Electro Mechanical Systems) technology, for example.

In case of a device which does not include cover member 209 presented in comparison with device 210 in this exemplary embodiment, the detection target gas may flow from the space 240A side toward the light receiving element 202 side via first opening 281A. Similarly, in case of a device which does not include optical filter 205 on second opening 282A presented in comparison with device 210 in this exemplary embodiment, the detection target gas may flow from the space 240A side toward the light receiving element 202 side via second opening 282A. According to the device presented as a comparison, a membrane of an infrared sensor may be deformed by pressure of the target detection gas when the gas flows from the space 240A side toward the light receiving element 202 side. When the membrane of the infrared sensor is deformed in the device of the comparison example, detection errors of the infrared sensor or damage to the infrared sensor may be caused.

According to device 210 in this exemplary embodiment, however, detection errors of the infrared sensor and damage to the infrared sensor caused by pressure of the detection target gas are suppressed even when light receiving element 202 includes an infrared sensor provided with a membrane.

Device 210 according to this exemplary embodiment is applicable to a gas sensor equipped on an air conditioner, a gas detection alarm, a vehicle exhaust gas measuring device, and alcohol detector, for example.

The respective components included in device 210 according to this exemplary embodiment are hereinafter described in more detail.

Light emitting element 201 is capable of emitting infrared light. As light emitting element 201, a semiconductor bare chip may be used. Light emitting element 201 is not limited to a semiconductor bare chip, but may be constituted by a chip size package. Light emitting element 201 may be constituted by a light emitting diode chip, or a resistance element or a laser diode provided on a semiconductor substrate, for example. Light emitting element 201 is capable of emitting infrared light having a wavelength easily absorbable by a detection target gas. Light emitting element 201 is allowed to be electrically connected to wiring 263 on board 206 by an appropriate method such as wire bonding. The entire size of device 210 can be reduced when light emitting element 201 is constituted by a semiconductor bare chip, in comparison with a device which uses a package type light emitting diode.

Light receiving element 202 is capable of receiving infrared light and converting the infrared light into an electric signal. As light receiving element 202, a semiconductor bare chip may be used. Light receiving element 202 is not limited to a semiconductor bare chip, but may be constituted by a chip size package. Light receiving element 202 may be constituted by a pyroelectric element or a photodiode chip, for example. Light receiving element 202 is allowed to be electrically connected to wiring 263 provided on board 206 by an appropriate method such as wire bonding. The entire size of device 210 can be reduced when light receiving element 202 is constituted by a semiconductor bare chip, in comparison with a device which uses a package type photodiode.

Optical member 204 is capable of guiding the infrared light from light emitting element 201 toward light receiving element 202. Optical member 204 is capable of covering the one surface 260A side of board 206 via space 240A into which the detection target gas is introducible. Optical member 204 may be formed as a resin molded component formed of a synthetic resin molded body. Optical member 204 may be made of polyphthalamide resin, for example. Optical member 204 is not limited to a resin molded component, but may be made of metal material. Optical member 204 formed as a resin molded component has a more accurate external appearance than a component made of metal material. It is preferable that outside surface 240B of optical member 204 is coated with metal material when optical member 204 is formed as a resin molded component. Optical member 204 may have a rectangular shape having an external size equivalent to an external size of reflection body 208 in a plan view. Optical member 204 is allowed to be fixed to board 206 in such a condition that a recess of optical member 204 faces one surface 260A of board 206 via reflection body 208. Optical member 204 may be provided with air holes 242 penetrating optical member 204 in a direction of a thickness of optical member 204. The detection target gas can be introduced into space 240A through air holes 242 of optical member 204. The detection target gas can be discharged from space 240A through air holes 242 of optical member 204. It is preferable that air holes 242 of optical member 204 are covered with dust filters 211 to prevent entrance of foreign material other than the outside air, such as dust, into air holes 242. Each of air holes 242 may have a rectangular shape in a plan view, for example. Each shape of air holes 242 is not limited to a rectangular shape, but may have other shapes such as a circular shape in a plan view. The number of air holes 242 is not limited to two, but may be one. Alternatively, three or more air holes 242 may be formed.

Optical member 204 includes first reflection mirror 241B which reflects the infrared light emitted from light emitting element 201 in a direction perpendicular to one surface 260A on the side opposed to one surface 260A and guides the infrared light toward light receiving element 202 disposed on the one surface 260A side of board 206. In optical member 204, first reflection mirror 241B is allowed to be formed in an appropriate shape of a recess of optical member 204. Optical member 204 may be formed as a resin molded component whose outside surface 240B is coated with metal material. First reflection mirror 241B may be formed integrally with optical member 204 by determining a shape of the resin molded component in an appropriate manner. For forming first reflection mirror 241B, metal material such as gold and aluminum may be formed on an inner surface of the recess of optical member 204 by deposition or plating. The reflection surface of first reflection mirror 241B is not limited to a smooth and flat-shaped surface. For example, first reflection mirror 241B may have a reflection surface having a parabolic shape, a spherical shape, or a polygonal shape. Alternatively, first reflection mirror 241B may have a reflection surface in a shape produced by combining a flat shape, a parabolic shape, a spherical shape, or a polygonal shape in an appropriate manner.

Optical filter 205 is capable of transmitting infrared light in a predetermined wavelength band. Optical filter 205 constitutes a band pass filter which has a transmission band containing a wavelength band of a wavelength of infrared light emitted from light emitting element 201. As optical filter 205, an interference filter having a multilayered structure of dielectric films may be used, for example. Examples of a base material of optical filter 205 include Ge, Si and other semiconductor materials, and methacrylic resin. Optical filter 205 is allowed to be accommodated within accommodation recess 280D of reflection body 208. Optical filter 205 may be fixed to accommodation recess 280D of reflection body 208 via a bonding material (not shown). Optical filter 205 may be fixed to light receiving element 202 via a bonding material. Examples of the bonding material may include glass having a low melting point, alloy having a low melting point, and resin material. Optical filter 205 is capable of preventing the detection target gas from flowing from the space 240A side of optical member 204 toward the light receiving element 202 side via second opening 282A. Similarly, optical filter 205 is capable of preventing optical characteristics of light emitting element 201 and light receiving element 202 from being deteriorated by dust or moisture entering from the space 240A side of optical member 204 via second opening 282A.

Board 206 is capable of outputting a signal received from the light receiving element 202 side to the outside. Light emitting element 201 and light receiving element 202 are provided on the one surface side 260A side of board 206. Optical member 204 is connectable to board 206. Board 206 may have a rectangular flat-plate-shaped external appearance. Board 206 is not limited to a rectangular flat-plate-shaped component, but may have various shapes such as a circular flat-plate shape and a polygonal flat-plate shape. As board 206, a glass epoxy resin substrate or a ceramic multilayered substrate may be used, for example. Electronic part 271 constituting signal processing circuit unit 207 may be mounted on board 206, for example. Board 206 includes wiring 263. According to board 206, light emitting element 202 can be electrically connected to electronic part 271 constituting signal processing circuit 207 via wiring 263.

Figure 36:
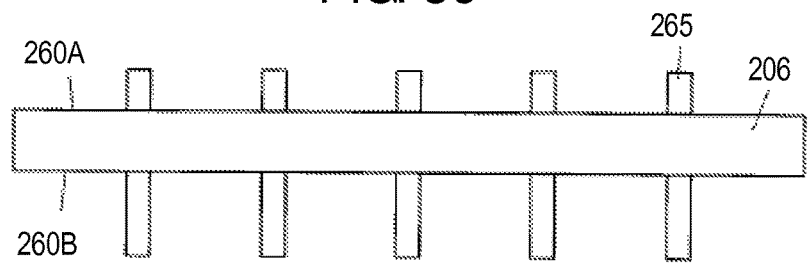
FIG. 36 is an explanatory side view illustrating an essential part of another device according to the seventh exemplary embodiment.

Board 206 includes conductor wiring 261 for outputting a signal from light receiving element 202 to the outside. According to board 206, the light receiving element 202 side is electrically connected to conductor wiring 261 via wiring 263. In device 210, surface mounting type receptacle 269 is allowed to be surface-mounted on conductor wiring 261 of board 206 via soldering or the like. Device 210 is electrically connectable with a wiring board (not shown) of an external apparatus by using receptacle 269. According to device 210, conductor wiring 261 may be electrically connected to the wiring board of the apparatus side via metal terminals 265 as illustrated in FIG. 36, instead of use of receptacle 269. According to device 210 provided with metal terminals 265, metal terminals 265 may be fixed to through holes (not shown) penetrating board 206. According to board 206, conductor wiring 261 around the through holes may be electrically connected with metal terminals 265 via soldering (not shown) or the like after insertion of metal terminals 265 into the through holes.

Figure 37:
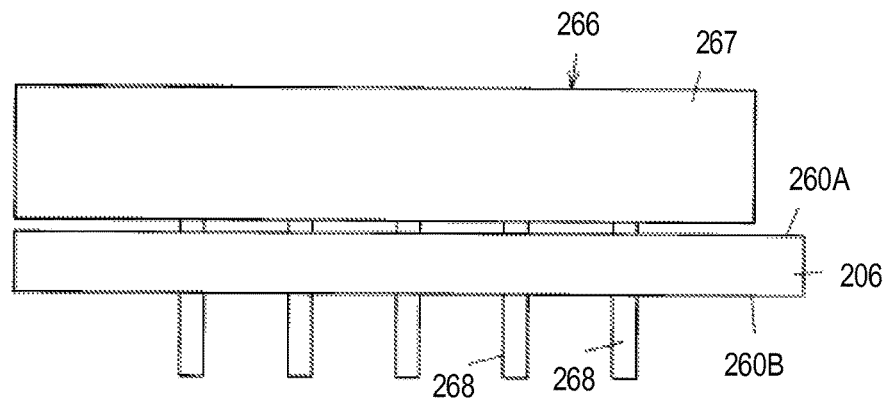
FIG. 37 is an explanatory side view illustrating an essential part of a still other device according to the seventh exemplary embodiment.

Similarly, device 210 may include receptacle 266 which contains contact pins 268 within connector body 267 formed by insulation material as illustrated in FIG. 37, instead of receptacle 269. According to device 210, contact pins 268 of receptacle 266 are electrically connected to conductor wiring 261. According to device 210, conductor wiring 261 is electrically connected to a plug electrically connected with the wiring board on the apparatus side via receptacle 266. Device 210 is capable of being electrically connected to the wiring board on the apparatus side by using of metal terminals 265, receptacle 266, or receptacle 269. Device 210 is preferably provided with screw holes 260C for receiving screws or the like fixing device 210 to the wiring board (not shown) of the external apparatus.

Device 210 in a mode different from this exemplary embodiment is manufacturable only by replacing board 206 containing conductor wiring 261 with board 206 containing conductor wiring 261 of a different wiring pattern. This structure can standardize components constituting device 210 and increase a degree of freedom for electric connection between device 210 and an external apparatus provided outside device 210 for each type of apparatus on which device 210 of this exemplary embodiment is mounted.

Signal processing circuit unit 207 is configured to allow emission of infrared light from light emitting element 201 by controlling light emitting element 201. Signal processing circuit unit 207 is configured to process a signal output from light receiving element 202 upon receiving infrared light. Signal processing circuit unit 207 may perform signal processing such as amplification, waveform shaping, signal sampling, and signal analog/digital conversion of the signal output from light receiving element 202. Signal processing circuit unit 207 may further perform signal processing such as signal calculation, signal correction, and determination that the detection target gas has an abnormal concentration, for example. Signal processing circuit unit 207 may be constituted of electronic part 271 such as an integrated circuit.

Reflection body 208 is capable of reflecting infrared light. Reflection body 208 may be constituted by a resin molded component formed of a synthetic resin molded body. Reflection body 208 may be made of polyphthalamide resin, for example. Reflection body 208 may include outside surface 280C coated with metal material. Reflection body 208 may be formed as a resin molded component on which metal material such as gold and aluminum is formed by deposition or plating. Reflection body 208 may be formed as a resin molded component whose outside surface 280C is coated with metal material. Reflection body 208 is not limited to a resin molded component, but may be made of metal material. For example, reflection body 208 may be made of metal material such as aluminum. Reflection body 208 whose outside surface 280C is made of metal is electrically connectable with outside surface 240B of metal material constituting optical member 204.

Reflection body 208 includes first opening 281A through which infrared light emitted from light emitting element 201 passes. Reflection body 208 includes second reflection mirror 280AA on a circumference of first opening 281A. Second reflection mirror 280AA converges infrared light in a direction perpendicular to one surface 260A. Reflection body 208 includes second opening 282A through which infrared light reflected on the opposed surface passes. Reflection body 208 includes third reflection mirror 280AC on a circumference of second opening 282A. Third reflection mirror 280AC converges infrared light on light receiving element 202. The structure of reflection body 208 which includes second reflection mirror 280AA and third reflection mirror 280AC for reflecting infrared light is capable of increasing light utilization efficiency of infrared light.

Figure 38:
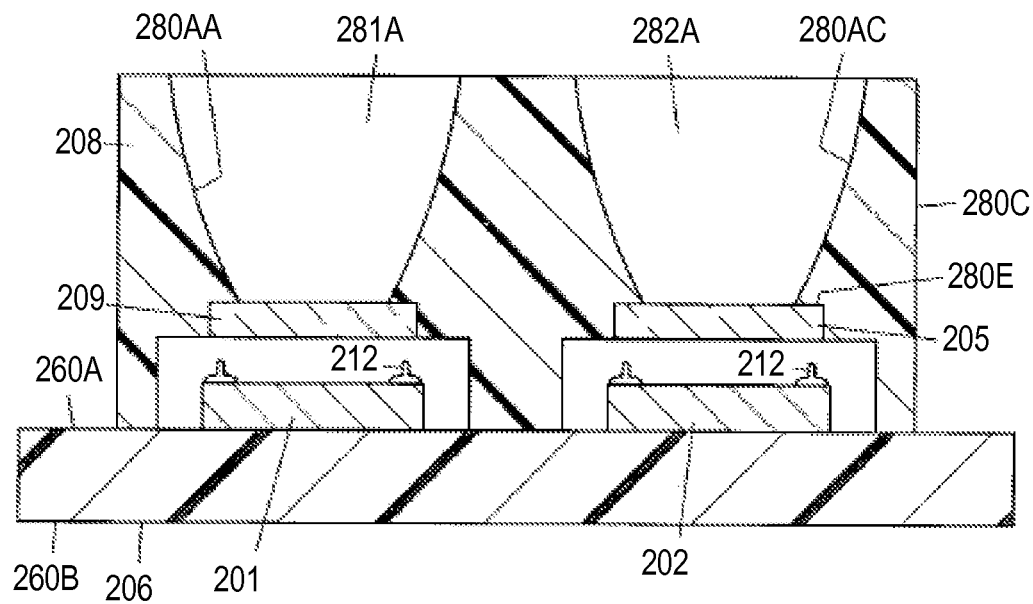
FIG. 38 is a cross-sectional view schematically illustrating an essential part of a further other device according to the seventh exemplary embodiment.

In case of reflection body 208 formed as a resin molded component, shapes of first opening 281A and second opening 282A are relatively easily formed into paraboloidal surfaces in comparison with reflection body 208 made of metal material. According to device 210 in this exemplary embodiment, cover member 209 is provided on the optical member 204 side of reflection body 208. Optical member 204 covers light emitting element 201. On the other hand, optical filter 205 is provided on the optical member 204 side of reflection body 208. Optical filter 205 covers light receiving element 202. According to device 210, cover member 209 may be provided on reflection body 208 which covers light emitting element 201 in such a position that cover member 209 faces light emitting element 201 as illustrated in FIG. 38. Similarly, optical member 205 may be provided on reflection body 208 which covers light receiving element 202 in such a position that optical member 205 faces light receiving element 202. In this case, reflection body 208 is provided with accommodation recesses 280E where cover member 209 and optical filter 205 are accommodated.

Cover member 209 is capable of closing first opening 281A. Cover member 209 is capable of preventing a gas from flowing from the space 240A side of optical member 204 toward the light receiving element 202 side via first opening 281A. Similarly, cover member 209 is capable of preventing optical characteristics of light emitting element 201 and light receiving element 202 from being deteriorated by dust or moisture entering from the space 240A side of optical member 204 via first opening 281A. Cover member 209 may have a flat plate shape, for example. It is preferable that cover member 209 is made of material having excellent translucency capable of transmitting infrared light emitted from light emitting element 201. Examples of material of cover member 209 include Ge, Si and other semiconductor materials, and methacrylic resin.

Eighth Exemplary Embodiment

Figure 39:
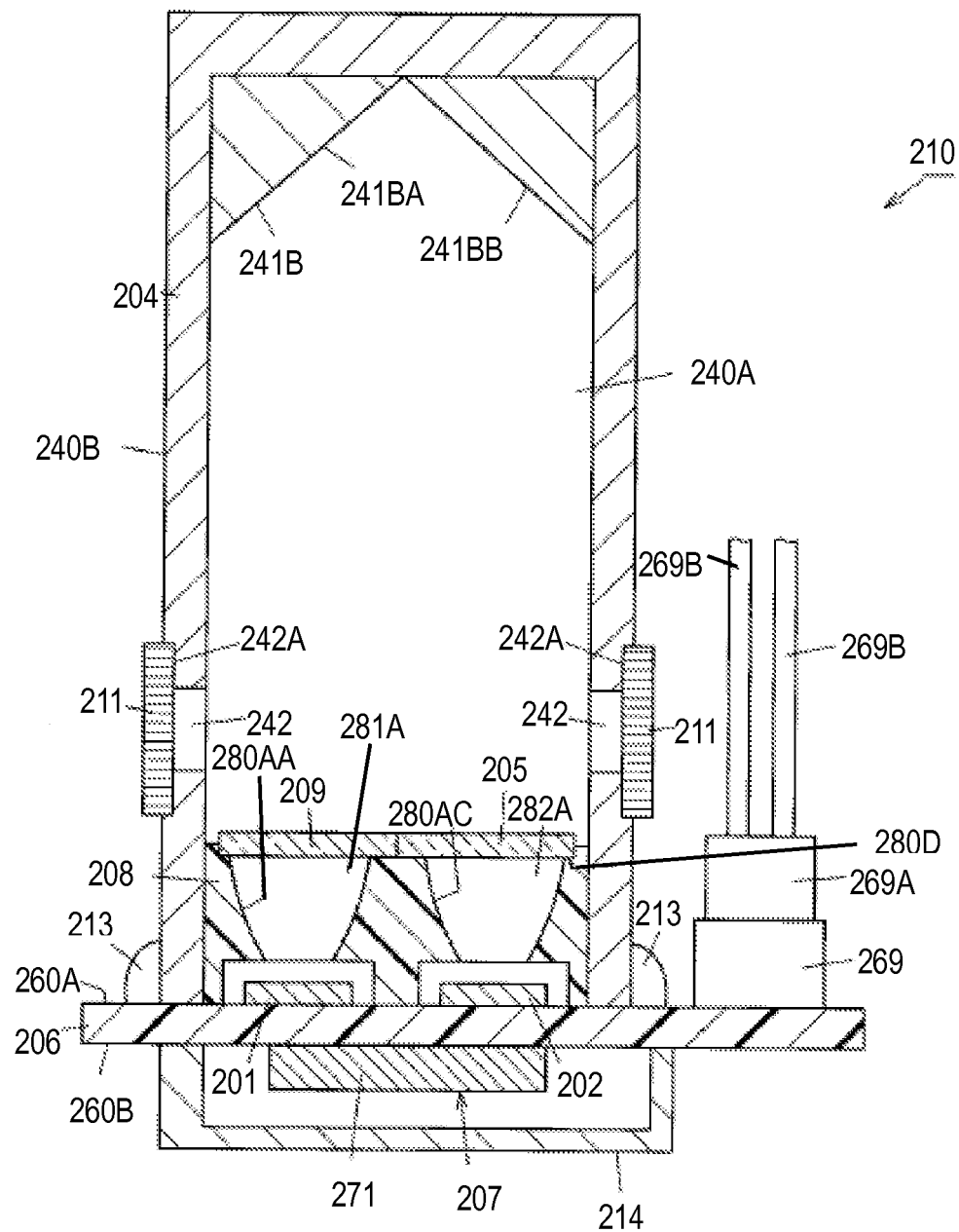
FIG. 39 is a cross-sectional view schematically illustrating a device according to an eighth exemplary embodiment.
Figure 40:
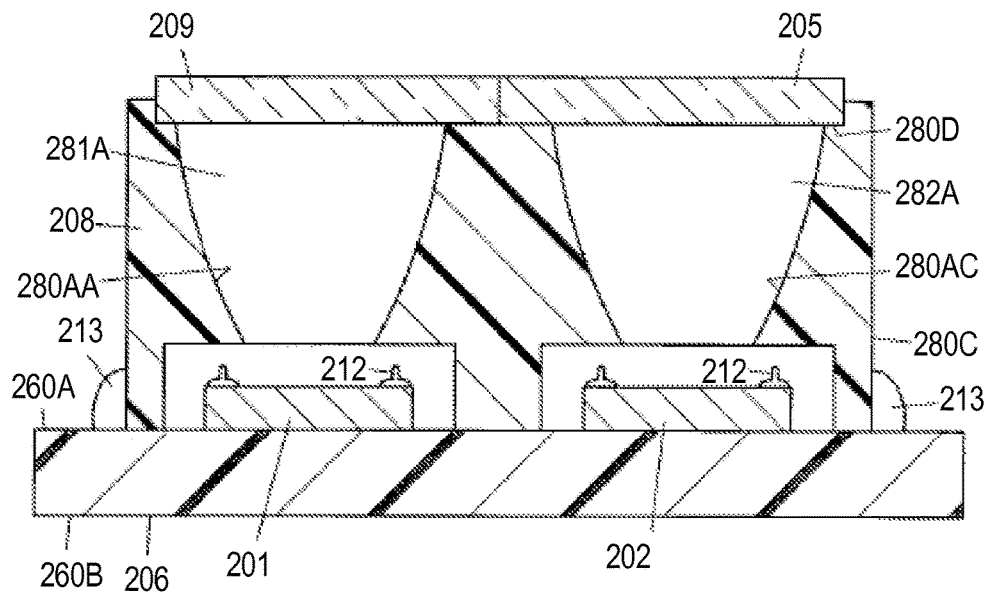
FIG. 40 is a cross-sectional view schematically illustrating an essential part of another device according to the eighth exemplary embodiment.

Device 210 according to this exemplary embodiment illustrated in FIGS. 39 and 40 is different from device 210 according to the seventh exemplary embodiment illustrated in FIG. 33 chiefly in that optical member 204 and reflection body 208 are electrically connected with the board 206 side. Constituent elements similar to corresponding constituent elements in the seventh exemplary embodiment have been given similar reference numbers, and the same explanation is not repeated when omission of the explanation is appropriate.

In device 210 in this exemplary embodiment, optical member 204 is formed as a resin molded component whose outside surface 240B is coated with metal material, or a metal body made of metal material. For example, the metal material of optical member 204 is electrically connected with ground of board 206 as illustrated in FIG. 39. According to device 210, optical member 204 may be joined to board 206 via soldering 213, thereby electrically connecting the metal material of optical member 204 and the ground of board 206. According to device 210, projections of optical member 204 are joined to lands around insertion holes 262A by soldering 213, for example. In device 210, only the lands around insertion holes 262A of board 206 need to be grounded.

Optical member 204 is a resin molded component formed of a synthetic resin molded body. Optical member 204 is gold-plated to form a metal portion (not shown) throughout outside surface 240B of optical member 204. According to device 210, optical member 204 formed as a resin molded component whose outside surface 240B is coated with metal material is electrically connected with the lands around insertion holes 262A of board 206 by soldering 213. In device 210, the lands around insertion holes 262A of board 206 are grounded. In other words, optical member 204 is a resin molded component whose outside surface 240B is coated with the metal portion of metal material, and the metal material is electrically connected with the ground of board 206.

In device 210, a potential of optical member 204 coated with the metal portion of metal material may be set to a reference potential. In this case, device 210 prevents noise from occurring in light emitting element 201, light receiving element 202, electronic part 271 or the like as a result of entrance of electromagnetic waves from the outside of device 210. Similarly, in device 210, a potential of reflection body 208 contacting optical member 204 is allowed to be set to the reference potential in accordance with setting of the potential of optical member 204 coated with the metal portion of metal material to the reference potential. By setting the potential of reflection body 208 to the reference potential, device 210 further prevents noise from occurring in light emitting element 201 and light receiving element 202 provided on board 206 and covered by reflection body 208, as a result of entrance of electromagnetic waves from the outside of device 210.

According to device 210 in this exemplary embodiment, for example, the metal material of reflection body 208 may be electrically connected with the ground of board 206 as illustrated in FIG. 40. According to device 210, the metal material of reflection body 208 may be electrically connected with the ground of board 206 by joining reflection body 208 and board 206 using soldering 213. In device 210, the metal portion made of metal material and formed on reflection body 208 only need to be joined with the lands of board 206 by soldering 213, for example. According to device 210, a potential of reflection body 208 coated with the metal material may be set to a reference potential. In this case, device 210 prevents noise from occurring in light emitting element 201, light receiving element 202, electronic part 271 or the like as a result of entrance of electromagnetic waves from the outside of device 210. Similarly, according to device 210, a potential of optical member 204 contacting reflection body 208 is allowed to be set to the reference potential in accordance with setting of the potential of reflection body 208 coated with metal material to the reference potential. By setting the potentials of optical member 204 and reflection body 208 to the reference potential, device 210 further prevents noise from occurring in light emitting element 201, light receiving element 202 or the like covered by reflection body 208 as a result of entrance of electromagnetic waves from the outside of device 210.

Ninth Exemplary Embodiment

Figure 41:
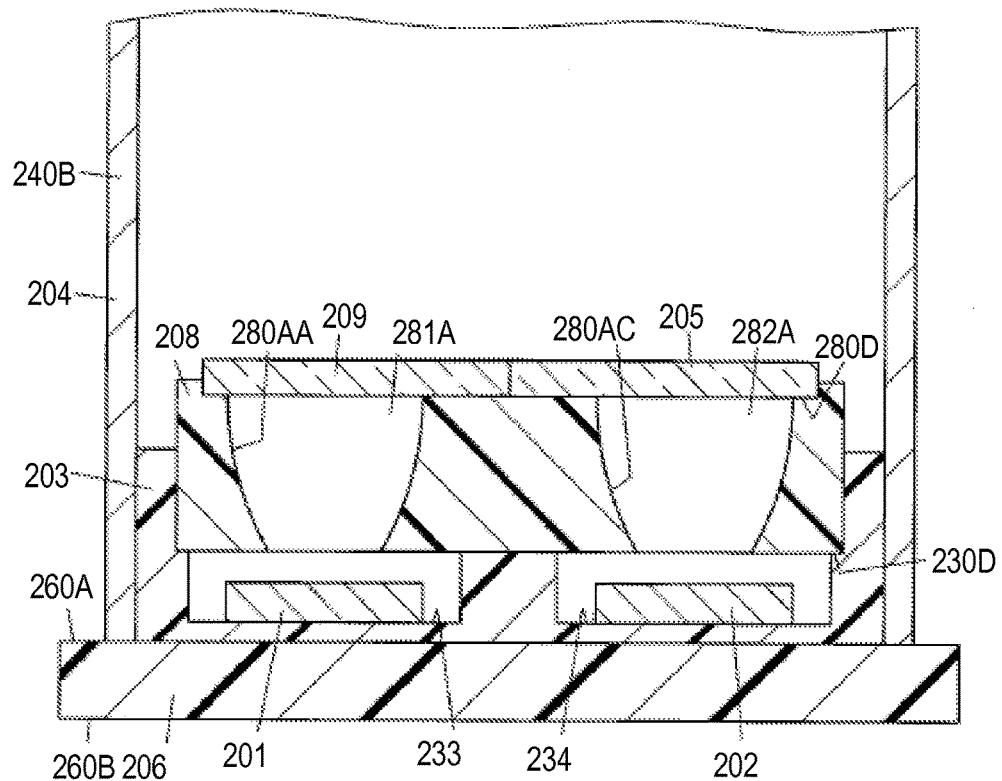
FIG. 41 is an explanatory cross-sectional view illustrating an essential part of a device according to a ninth exemplary embodiment.
Figure 42:
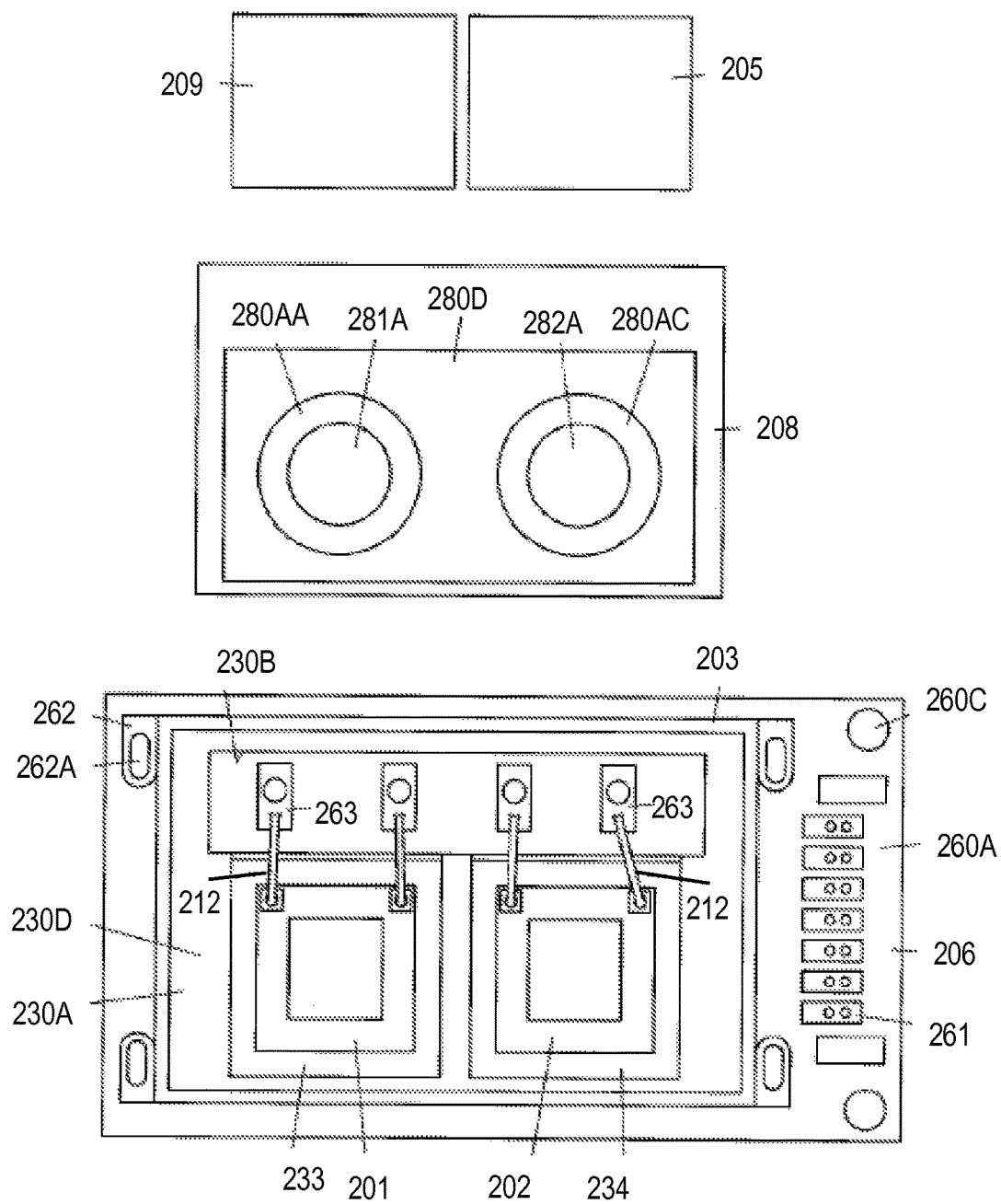
FIG. 42 is a plan view illustrating the essential part of the device according to the ninth exemplary embodiment.

Device 210 according to this exemplary embodiment illustrated in FIGS. 41 and 42 is different from device 210 according to the seventh exemplary embodiment illustrated in FIG. 33 chiefly in that light emitting element 201 and light receiving element 202 are mounted on the one surface 260A side of board 206 via support body 203, rather than mounted directly on one surface 260A of board 206. Constituent elements similar to corresponding constituent elements in the seventh exemplary embodiment have been given similar reference numbers, and the same explanation is not repeated when omission of the explanation is appropriate.

In device 210 in this exemplary embodiment, light emitting element 201 and light receiving element 202 are provided on support body 203 which supports light emitting element 201 and light receiving element 202 with a predetermined distance therebetween as illustrated in FIGS. 41 and 42. Support body 203 is provided on the one surface 260A side of board 206.

Support body 203 is capable of supporting light emitting element 201 and light receiving element 202 on the one surface 230A side. Support body 203 may have a bottomed and square cylindrical external shape. Support body 203 may be constituted by a resin molded component formed of a synthetic resin molded body. Support body 203 may be made of polyphthalamide resin, for example. One surface 260A of board 206 is exposed through cylindrical opening 230B of support body 203.

Support body 203 is provided with first recess 233 on the one surface 230A side of support body 203. Light emitting element 201 is mounted on an inner bottom surface of first recess 233 of support body 203. According to device 210, light emitting element 201 is mounted on the inner bottom surface of first recess 233 via a die bond material (not shown). In device 210, light emitting element 201 is electrically connected to wiring 263 provided on one surface 260A of board 206 and by wire bonding using metal wire 212, for example. Light emitting element 201 is constituted by a light emitting diode capable of emitting infrared light. This light emitting diode is constituted by a semiconductor bare chip.

Support body 203 is provided with second recess 234 on the one surface 230A side of support body 203. Light receiving element 202 is mounted on an inner bottom surface of second recess 234 of support body 203. According to device 210, light receiving element 202 is mounted on the inner bottom surface of second recess 234 via a die bond material (not shown). In device 210, light receiving element 202 is electrically connected to wiring 263 formed on one surface 260A of board 206 by wire bonding using metal wire 212. Light receiving element 202 is constituted by an infrared sensor capable of receiving infrared light. The infrared sensor is constituted by a pyroelectric element. The infrared sensor is provided as a semiconductor bare chip. Support body 203 supports light emitting element 201 and light receiving element 202 on the one surface 230A side. In case of support body 203, reflection body 208 is provided on the one surface 230A side of support body 203 so as to cover light emitting element 201 and light receiving element 202.

Support body 203 is provided with accommodation recess 230D formed in one surface 230A of support body 203. Support body 203 accommodates reflection body 208 within accommodation recess 230D of support body 203 in a manner that reflection body 208 covers opening 230B. According to device 210, reflection body 208 can be positioned with respect to support body 203 by accommodation of reflection body 208 within accommodation recess 230D. According to device 210, alignment between light emitting element 201 and second reflection mirror 280AA is facilitated by accommodation of reflection body 208 within accommodation recess 230D. According to device 210, alignment between light receiving element 202 and third reflection mirror 280AC is facilitated by accommodation of reflection body 208 within accommodation recess 230D. According to device 210, light emitting element 201 can be positioned at a focus of a parabolic reflection surface of second reflection mirror 280AA by accommodation of reflection body 208 within accommodation recess 230D. According to device 210 of this exemplary embodiment, light receiving element 202 can be positioned at a focus of a parabolic reflection surface of third reflection mirror 280AC by accommodation of reflection body 208 within accommodation recess 230D.

In device 210, optical member 204 is overlaid on board 206 via support body 203 and reflection body 208*by* insertion of projections of optical member 204 into insertion holes 262A of board 206. According to device 210, optical member 204 is fixed to board 206 via support body 203 in a state of insertion of the projections of optical member 204 into insertion holes 262A of board 206. In device 210, the projections of optical member 204 can be joined and fixed to lands 262 around insertion holes 262A of board 206 by soldering 213, for example. In device 210, support body 203 is fixed with reflection body 208 by using a not-shown adhesive. According to device 210, infrared light emitted from light emitting element 201 is allowed to pass through first opening 281A by mounting of reflection body 208 on support body 203. According to device 210 in this exemplary embodiment, light receiving element 202 is allowed to receive infrared light after passing through second opening 282A by mounting of reflection body 208 on support body 203.

In device 210 according to this exemplary embodiment, reflection body 208, optical member 204, and support body 203 on which light emitting element 201 and light receiving element 202 are mounted are optically coupled. In addition, in device 210, support body 203 and optical member 204 are fixed to board 206 which does not require relatively high alignment accuracy in comparison with the optical coupling which requires relatively high alignment accuracy. According to device 210, conductor wiring 261 for outputting a signal received from the light receiving element 202 side to the outside is provided on board 206 which does not require relatively high alignment accuracy, and therefore a degree of freedom for electric connection to the outside is further increased. In other words, in device 210 according to this exemplary embodiment, support body 203 which holds light emitting element 201 and light receiving element 202 with a predetermined distance therebetween is functionally separated from board 206 which includes conductor wiring 261 for outputting signals to the outside in accordance with accuracy of alignment.

Accordingly, device 210 in a mode different from this exemplary embodiment is manufacturable only by replacing board 206 containing conductor wiring 261 with board 206 containing conductor wiring 261 of a different wiring pattern. This structure can standardize components constituting device 210 and increase a degree of freedom for electric connection between device 210 and an external apparatus provided outside device 210 for each type of apparatus on which device 210 of this exemplary embodiment is mounted.

Tenth Exemplary Embodiment

Device 210 according to this exemplary embodiment is different from device 210 according to the seventh exemplary embodiment illustrated in FIG. 33 in that two or more sets of optical filter 205 and light receiving element 202 are provided for one light emitting element 201, instead of one set of optical filter 205 and light receiving element 202 for one light emitting element 201. Constituent elements similar to corresponding constituent elements in the seventh exemplary embodiment have been given similar reference numbers, and the same explanation is not repeated when omission of the explanation is appropriate.

Figure 43:
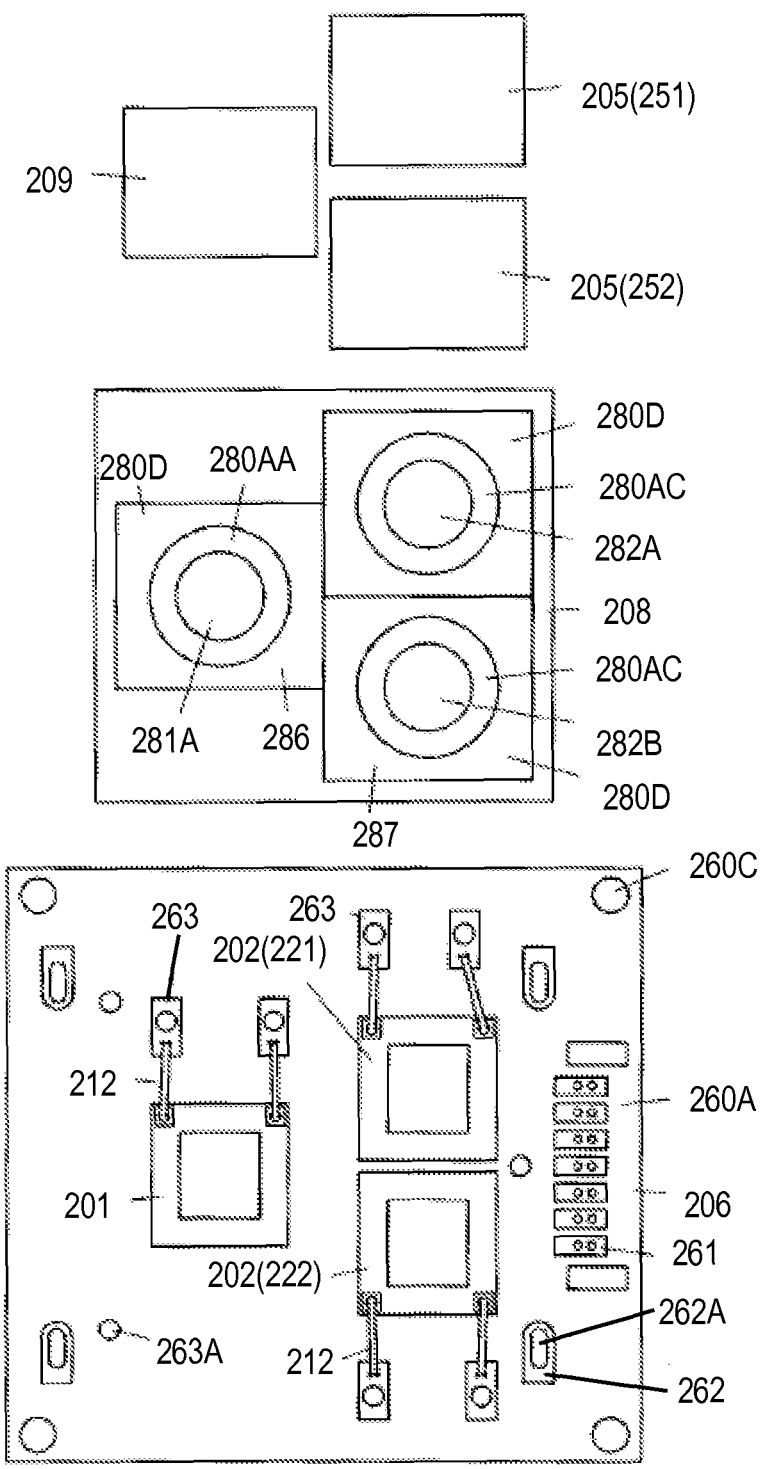
FIG. 43 is a plan view illustrating a main part of a device according to a tenth exemplary embodiment.
Figure 44:
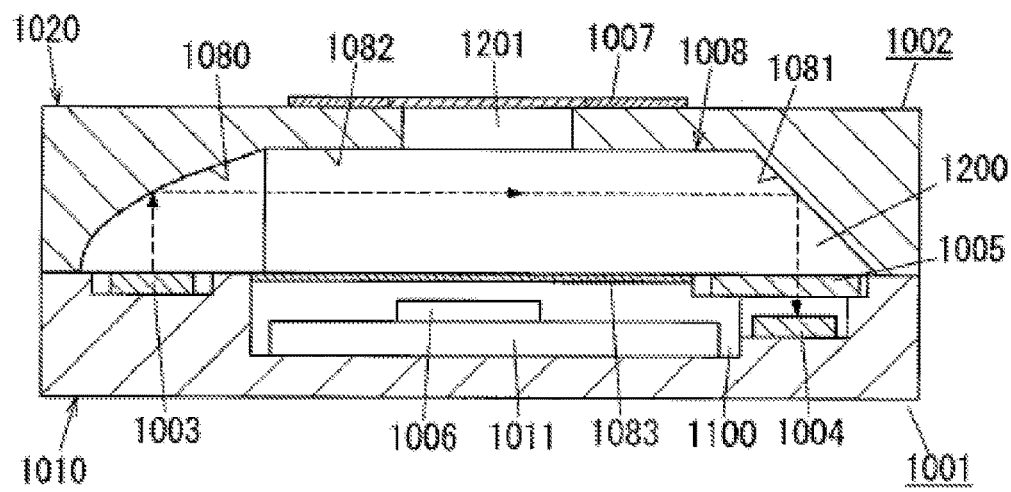
FIG. 44 is a cross-sectional view of a conventional gas component detecting device.
Figure 45:
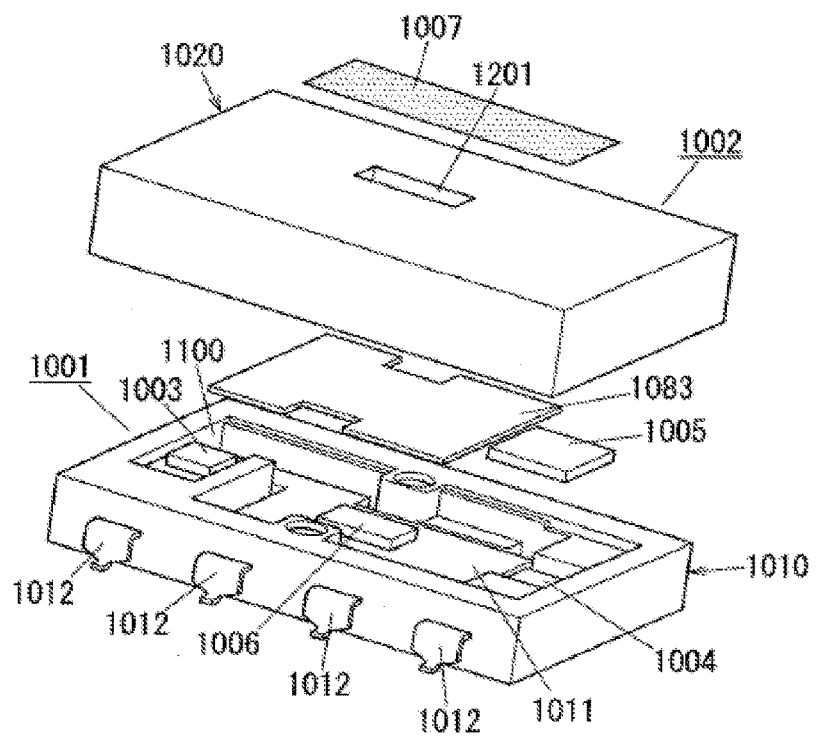
FIG. 45 is an exploded perspective view of the conventional gas component detecting device.
Figure 46:
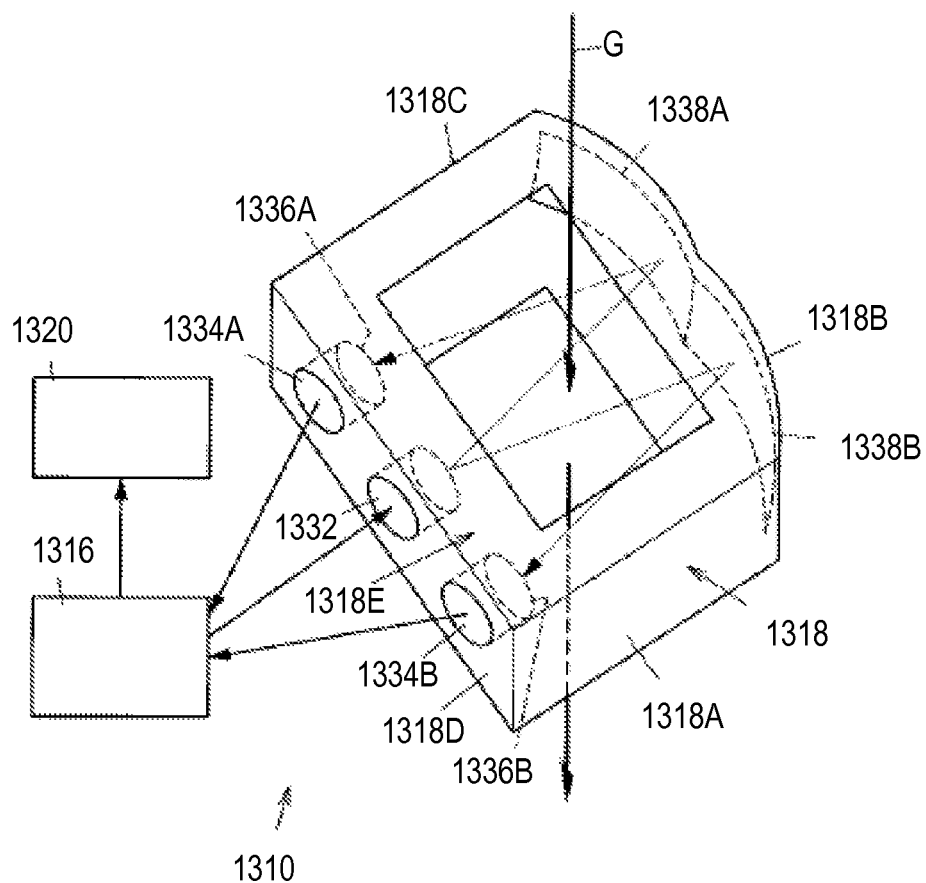
FIG. 46 is a perspective view of another conventional gas detector.

According to device 210 in this exemplary embodiment, optical filters 205 are provided for light receiving elements 202, respectively, so as to cover a pair of light receiving elements 202 as illustrated in FIG. 43. The pair of light receiving elements 202 are hereinafter referred to as first light receiving element 221 and second light receiving element 222 as well. In device 210 according to this exemplary embodiment, one of optical filters 205 provided for the pair of light receiving elements 202, respectively, constitutes first optical filter 251 which has a transmission band containing an infrared light wavelength band absorbed by a detection target gas. On the other hand, according to device 210, the other of optical filters 205 provided for the pair of light receiving elements 202, respectively, constitutes second optical filter 252 which does not have a transmission band containing the wavelength band of the infrared light absorbed by the detection target gas, but has a transmission band containing wavelengths around the wavelength band of the infrared light absorbed by the detection target gas.

According to device 210 in this exemplary embodiment, therefore, optical filters 205 include first optical filter 251 which has a transmission band containing an infrared light wavelength band absorbed by the detection target gas, and second optical filter 252 which has a transmission band different from the transmission band of first optical filter 251. Light receiving elements 202 includes first light receiving element 221 which photoelectrically converts infrared light transmitted through first optical filter 251, and second light receiving element 222 which photoelectrically converts infrared light transmitted through second optical filter 252.

According to device 210, reflection body 208 includes first optical filter 251 and second optical filter 252. Reflection body 208 includes second opening 282A through which infrared light reflected on the opposed surface passes. Reflection body 208 further includes third opening 282B through which the infrared light reflected on the opposed surface passes. According to device 210, reflection body 208 may include first reflection body 286 containing first opening 281A, and second reflection body 287 containing second opening 282A and third opening 282B. First through third openings 281A through 282B may be provided either as separate bodies or as an integrated body.

Device 210 is capable of introducing the outside air into space 240A of optical member 204 via air hole 242. According to device 210, an amount of infrared light transmitted through first optical filter 251 and received by first light receiving element 221 decreases with respect to that of infrared light emitted from light emitting element 201 in accordance with a concentration of the detection target gas. According to device 210, when the concentration of the detection target gas is low, an amount of infrared light received by first light receiving element 221 becomes close to the amount of infrared light emitted from light emitting element 201. When the concentration of the detection target gas is high, the amount of infrared light received by first light receiving element 221 decreases. According to device 210, an amount of infrared light transmitted through second optical filter 252 and received by second light receiving element 222 does not vary in accordance with the concentration of the detection target gas.

In device 210, signal processing circuit unit 207 processes a signal indicating an amount of received infrared light and output from light receiving element 202. Device 210 is capable of detecting a concentration of the detection target gas contained in space 240A of optical member 204.

According to device 210 in this exemplary embodiment, signal processing circuit unit 207 calculates the concentration of the detection target gas based on a difference between signal levels output from the pair of light receiving elements 202. Signal processing circuit unit 207 obtains the difference between the signal levels output from first light receiving element 221 and second light receiving element 222, and calculates the concentration of the detection target gas based on this difference.

When signal processing circuit unit 207 of device 210 calculates a concentration of a gas based on only the signal level output from one of light receiving elements 202, detection accuracy at the time of detection of the concentration of the gas may lower due to a variation of the signal level output from light receiving element 202 caused by some disturbance factor.

However, signal processing circuit unit 207 of device 210 according to this exemplary embodiment calculates a concentration of the detection target gas based on a difference between signal levels output from first light receiving element 221 and second light receiving element 222. Accordingly, lowering of detection accuracy at the time of detection of the concentration of the gas is suppressed according to device 210 by canceling variations caused by some disturbance factor based on the difference between the signal levels output from first light receiving element 221 and second light receiving element 222.

While not shown in the figure, optical filters 205 of device 210 may include a third optical filter which has a transmission band different from the respective transmission bands of first optical filter 251 and second optical filter 252. Light receiving element 202 may include a third light receiving element which photoelectrically converts infrared light after passing through the third optical filter.

Thanks to the structure, device 210 according to this exemplary embodiment is capable of detecting a plurality of types of gases. Device 210 discussed in the seventh exemplary embodiment is a gas sensor for detecting one type of gas contained in the outside air. However, a gas sensor capable of detecting different types of gases for each set of light receiving element 202 and optical filter 205 is realizable when a plurality of sets of light receiving element 202 and optical filter 205 are equipped. Device 210 according to this exemplary embodiment includes two or more sets of light receiving element 202 and optical filter 205. Accordingly, concentrations of different types of gases are detectable based on outputs from respective light receiving elements 202.

More specifically, device 210 includes first light receiving element 221 as light receiving element 202 for gas detection. Device 210 includes second light receiving element 222 as light receiving element 202 for gas detection. In device 210 in this exemplary embodiment, each of optical filters 205 constitutes a band pass filter which has a transmission band containing a predetermined wavelength. Device 210 which includes a plurality of sets of optical filter 205 and receiving element 202 for gas detection is capable of detecting a plurality of types of gases. Device 210 is thus capable of independently detecting concentrations of two different types of gases from a plurality of types of gases contained in the outside air. Device 210 according to this exemplary embodiment is capable of simultaneously detecting both of a first gas (such as carbon monoxide) and a second gas (such as nitrogen oxide) among two types of gases. Moreover, device 210 according to this exemplary embodiment may include a third optical filter which transmits a band not absorbed by either the first gas or the second gas. The third light receiving element receives infrared light transmitted through the third optical filter, and outputs a signal generated by photoelectric conversion to signal processing circuit unit 207. Signal processing circuit unit 207 measures a signal change ratio from initial output from light emitting element 201 based on the signal output from the third light receiving element. According to device 210, signal processing circuit unit 207 after measuring the signal change ratio from the initial output from light emitting element 201 corrects output from first light receiving element 221 and output from second light receiving element 222. Device 210 is capable of eliminating effects of deterioration of light emitting element 201 with time or the like, and improving measurement accuracy by correcting the signals output from first light receiving element 221 and second light emitting element 222.

A device according to the present disclosure is capable of increasing a degree of freedom for electric connection with an outside, and applicable to a gas detecting device for detecting a particular substance, for example.

What is claimed is:

1. A device comprising:
   a light emitting element;
   a light receiving element;
   an electronic part for processing a signal output from the light receiving element;
   an optical member covering the light emitting element and the light receiving element; and
   a board having a main surface on which the electronic part is disposed; and
   a support body disposed on the main surface of the board and surrounding the electronic part,
   wherein the light emitting element and the light receiving element are disposed on the support body along a normal direction of the main surface of the board, the normal direction being perpendicular to the main surface of the board, such that the support body is disposed between the board and both the light emitting element and light receiving element, and
   the board includes a terminal electrically connected to the light receiving element, the terminal is disposed on the main surface outside the support body and is not covered by the support body, while the electronic part are disposed on the main surface inside the support body, when the device is viewed from the normal direction of the main surface.

2. The device according to claim 1, further comprising a reflection body disposed above the light emitting element and the light receiving element, and provided with a first opening immediately above the light emitting element and a second opening immediately above the light receiving element.

3. The device according to claim 2, wherein the support body further comprises an accommodation recess, and the reflection body is disposed in the accommodation recess.

4. The device according to claim 1, wherein the support body includes a recess having stepped side surfaces, and the device further comprises an optical filter disposed on the stepped side surfaces of the recess and laid on an optical path for guiding infrared light from the light emitting element toward the light receiving element side, and for transmitting infrared light in a predetermined wavelength band.

5. The device according to claim 4, wherein
   the optical filter includes a first optical filter having a transmission band containing a wavelength band of infrared light absorbed by gas that is a detection target, and a second optical filter having a transmission band different from the transmission band of the first optical filter, and
   the light receiving element includes a first light receiving element for photoelectrically converting infrared light transmitted through the first optical filter, and a second light receiving element for photoelectrically converting infrared light transmitted through the second optical filter.

6. The device according to claim 1, wherein the optical member has a larger length in a vertical direction than in a planar direction.

7. The device according to claim 4, wherein the stepped side surfaces have a depth in a direction of a thickness of the support body equal to the thickness of each of the optical filters.

* * * * *